(12) United States Patent
Ito et al.

(10) Patent No.: US 11,045,069 B2
(45) Date of Patent: Jun. 29, 2021

(54) WAVEGUIDE, IMAGE TRANSMISSION APPARATUS INCLUDING WAVEGUIDE, ENDOSCOPE INCLUDING WAVEGUIDE, AND ENDOSCOPE SYSTEM

(71) Applicant: OLYMPUS CORPORATION, Hachioji (JP)

(72) Inventors: Keigo Ito, Nagano (JP); Tadashi Watanabe, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 25 days.

(21) Appl. No.: 16/672,396

(22) Filed: Nov. 1, 2019

(65) Prior Publication Data
US 2020/0060513 A1    Feb. 27, 2020

Related U.S. Application Data

(63) Continuation of application No. PCT/JP2018/011729, filed on Mar. 23, 2018.

(30) Foreign Application Priority Data

May 2, 2017    (JP) .............................. JP2017-091971

(51) Int. Cl.
    *A61B 1/00*    (2006.01)
    *A61B 1/07*    (2006.01)
    (Continued)

(52) U.S. Cl.
    CPC ...... *A61B 1/00009* (2013.01); *A61B 1/00013* (2013.01); *A61B 1/07* (2013.01); *H01P 3/122* (2013.01); *H01P 3/14* (2013.01)

(58) Field of Classification Search
    CPC ... H01P 3/122; H01P 3/14; H01P 3/12; A61B 1/00009; A61B 1/00013; A61B 1/07; A61B 1/051
    See application file for complete search history.

(56) References Cited

U.S. PATENT DOCUMENTS

| 5,528,208 A | 6/1996 | Kobayashi |
| 2010/0001809 A1* | 1/2010 | Yanagisawa ............ H01P 5/103 333/26 |

(Continued)

FOREIGN PATENT DOCUMENTS

| JP | 2800636 B2 | 5/1993 |
| JP | H06326505 A | 11/1994 |

(Continued)

OTHER PUBLICATIONS

International Search Report (ISR) dated Jun. 26, 2018 (and English translation thereof), issued in International Application No. PCT/JP2018/011729.

(Continued)

*Primary Examiner* — Leslie C Pascal
(74) *Attorney, Agent, or Firm* — Holtz, Holtz & Volek PC

(57) ABSTRACT

A flexible waveguide includes an inner dielectric, and a flexible external conductor disposed in a position covering an outer periphery of the dielectric, the flexible waveguide conducting a radio wave in a frequency band equal to or longer than a millimeter wave or a submillimeter wave near 60 GHz or more. The external conductor includes a metal layer, the metal layer has a shape displacement structure, a shape of an inner periphery side section of which faces the inner dielectric and is cyclic in the waveguide longitudinal direction, the shape displacement structure being a cyclic structure satisfying λmr<λch, where λmr represents a center wavelength of a main reflection band due to the cyclic structure and λch represents a cutoff wavelength in a high-order mode of the waveguide.

11 Claims, 37 Drawing Sheets

(51) Int. Cl.
    *H01P 3/14*     (2006.01)
    *H01P 3/12*     (2006.01)

(56)     References Cited

U.S. PATENT DOCUMENTS

2016/0056860 A1*   2/2016   Okada ................ H04B 3/52
                                                        375/257
2018/0136456 A1    5/2018   Watanabe et al.
2019/0081376 A1*   3/2019   Takeda ................ H01P 3/165

FOREIGN PATENT DOCUMENTS

| JP | H08195605 A | 7/1996 | |
|---|---|---|---|
| JP | 4724849 B2 | 4/2011 | |
| JP | 2015131913 A | 7/2015 | |
| JP | 2015185858 A | 10/2015 | |
| JP | 2018099310 A | 6/2018 | |
| WO | 2017002585 A1 | 1/2017 | |
| WO | WO-2017179444 A1 * | 10/2017 | .............. H01P 5/087 |

OTHER PUBLICATIONS

Written Opinion of the International Searching Authority dated Jun. 26, 2018 issued in International Application No. PCT/JP2018/011729.

* cited by examiner

A : 0.33~1.0mm
B : 0.33~1.0mm
D : 0.1mm
L : 0.66~2.0mm

|      | m | n |
|------|---|---|
| TE10 | 1 | 0 |
| TE20 | 2 | 0 |
| TE01 | 0 | 1 |
| TE11 | 1 | 1 |
| TE02 | 0 | 2 |

|              |      | CUTOFF WAVELENGTH $\lambda c$ [mm] | CUTOFF FREQUENCY $fc$ [GHz] |
|--------------|------|---|-----|
| (BASIC)      | TE10 | $\lambda c[10]=$ 7.5 | 40 |
| (HIGH ORDER) | TE20 | $\lambda c[20]=$ 3.8 | 80 |
| ↓            | TE01 | $\lambda c[01]=$ 3.8 | 80 |
| ↓            | TE11 | $\lambda c[11]=$ 3.4 | 89 |
| ↓            | TE02 | $\lambda c[02]=$ 1.9 | 160 |

A : 0.33~1.0mm
B : 0.33~1.0mm
D : 0.02~0.2mm
L : 0.66~2.0mm

| NUMBER OF BRAIDED STRINGS(m) | THREAD WIDTH(s) | HOLE DIAMETER(p) |
|---|---|---|
| 8 | 0.75 | 0.66 |
| 16 | 0.36 | 0.35 |
| 32 | 0.18 | 0.18 |

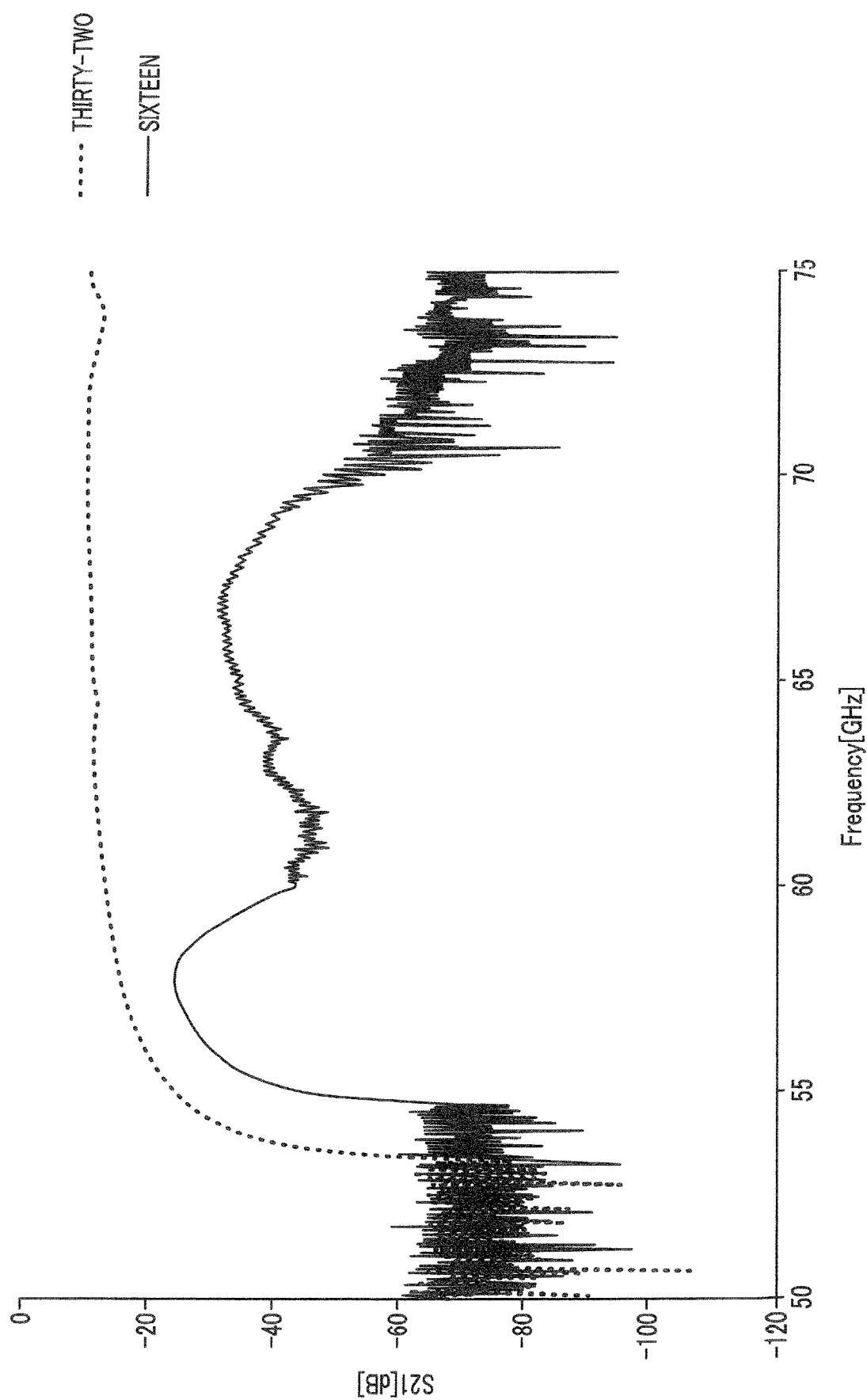

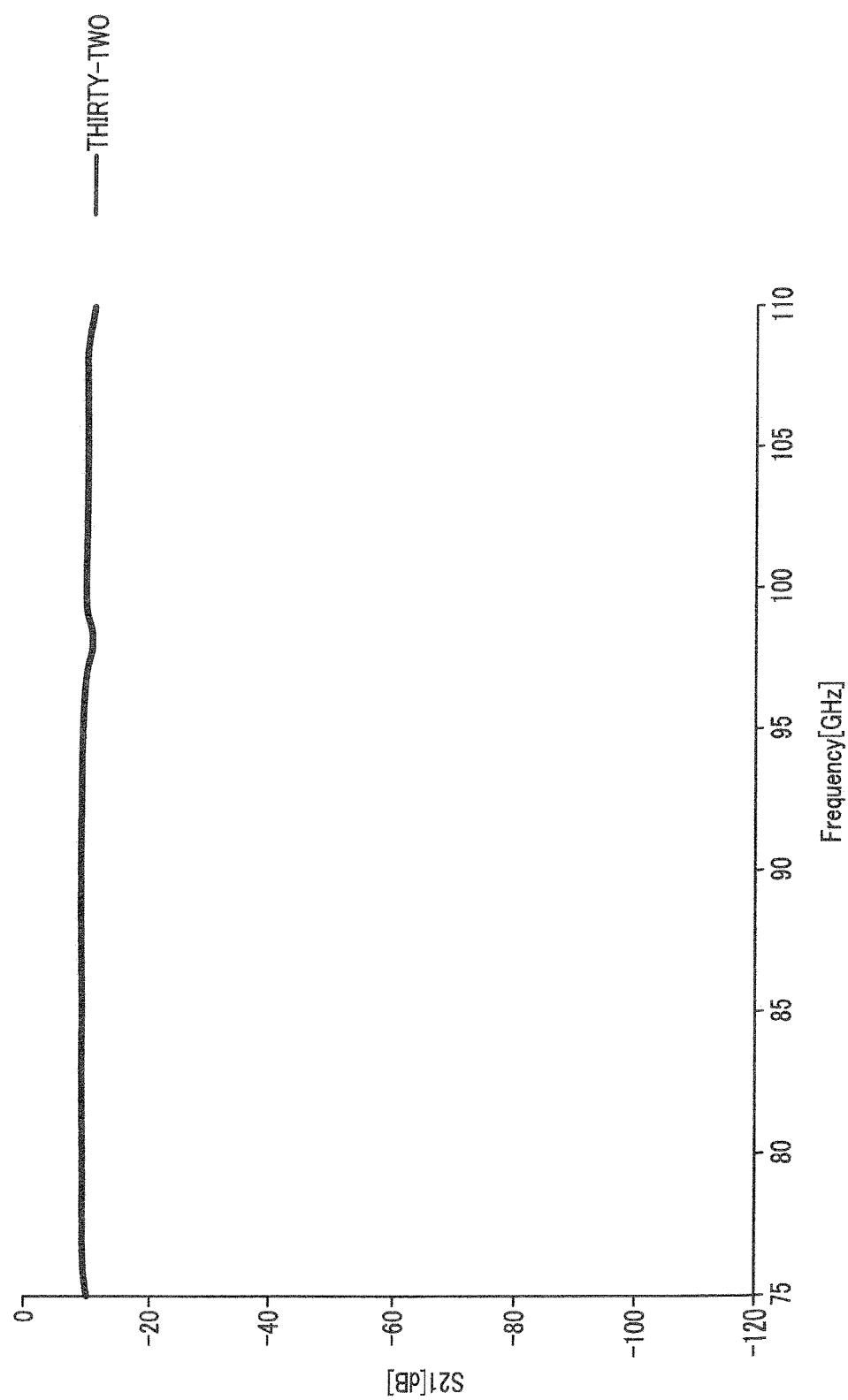

WAVEGUIDE, IMAGE TRANSMISSION APPARATUS INCLUDING WAVEGUIDE, ENDOSCOPE INCLUDING WAVEGUIDE, AND ENDOSCOPE SYSTEM

CROSS REFERENCE TO RELATED APPLICATION

This application is a continuation application of PCT/JP2018/011729 filed on Mar. 23, 2018 and claims benefit of Japanese Application No. 2017-091971 filed in Japan on May 2, 2017, the entire contents of which are incorporated herein by this reference.

BACKGROUND OF INVENTION

1. Field of the Invention

The present invention relates to a waveguide used for high-frequency radio wave signal transmission and, more particularly, to a waveguide suitable for radio wave transmission in a band equal to or higher than a millimeter wave or submillimeter wave band, an image transmission apparatus including the waveguide, an endoscope including the waveguide, and an endoscope system.

2. Description of the Related Art

In recent years, a communication environment having communication speed exceeding 1 Gbps has been prevailing even in general homes by means of a technique such as so-called FTTH (Fiber To The Home). Terminals having high processing abilities such as a smartphone have been widely adopted. A usable communication technique and speed of information processing, that is, "hard performance" has been markedly improved.

Quality and quantity of information usable by individuals or companies, that is, "soft use" has also been remarkably expanded by means of use of high precision/large capacity videos represented by 4K/8K images exceeding so-called FHD (full high definition), expansion of information access via the Internet, and the like.

These also greatly contribute to birth of new methods and added values such as development of artificial intelligence (AI) by big data analysis and deep learning that particularly attract attention in recent years.

In this way, the improvement of the "hard performance" and the expansion of the "soft use" act like both wheels of a cart and the techniques in these years have been markedly developed and new added values are born. As a result, performance required to an information communication technique at a present point in time is incomparably higher than the performance in the past. Focusing on a signal transmission line among technical elements necessary for information communication, it turns out that performance required in this field is extremely high.

At present, it can be said that "electric interconnection (connection by a metal wire) is mainly used in a region where a transmission distance is short and transmission speed is low" and, on the other hand, optical interconnection (connection by optical communication, that is, connection by an optical fiber) is mainly used in a region where a transmission distance is long and transmission speed is high".

In other words, it can be said that, for example, a limit in which the electric interconnection at approximately several meters can be used is transmission speed of approximately 2.5 Gbps and, if the transmission speed exceeds 2.5 Gbps, the optical interconnection (optical communication) is effective means.

In this way, the optical communication is regarded as the effective means in the region where the transmission distance is long and the transmission speed is high. However, it is known that the optical communication has a problem concerning reliability of signal transmission. In other words, since, in general, an optical fiber for communication is configured by one wire containing quartz glass as a main component, there is a risk that the optical fiber, which is a signal transmission line, is unexpectedly cut by influence of unintended shock or the like.

Similarly, it is also known that the optical communication has a problem concerning connectivity. In other words, since, in an optical fiber for communication usually in use, a diameter of a core wire called core for transmitting an optical signal is only approximately 50 μm or less, extremely high positioning accuracy in μm order is necessary for connection of the optical fiber for communication. Moreover, there is a risk that the optical fiber for communication cannot be connected because of influence of dust.

Incidentally, in the electric interconnection (the connection by the metal wire), in general, a line is configured by binding a plurality of thin wires. When the line is cut, the thin wires are gradually cut. Therefore, communication performance of the electric interconnect is gradually deteriorated. It is possible to take measures beforehand by learning the deterioration in the communication performance. Usually, connection of the line only has to have accuracy in 0.1 mm order and influence of dust is easily eliminated. Therefore, the connection of the line does not particularly involve difficulty.

In other words, because of the presence of the problems, in particular, in a use in which high reliability is requested for communication or a use in which connection of lines is requested in use, the optical communication is considered to be not an alternative of the electric interconnection.

In view of the circumstances described above, as a method that can realize communication speed of 5 Gbps or more at length of approximately several centimeters to five meters or less, the inventor proposes, in Japanese Patent Application No. 2015-131913, a technique for using a radio wave and a waveguide as a new signal transmission scheme for overcoming a problem of a signal transmission scheme by an optical fiber while overcoming a limit of transmission speed, which is a problem of a signal transmission scheme by a lead wire.

In other words, with a flexible waveguide that can be applied to communication in approximately a size of an electric board to approximately length of a general wire and transmits a radio wave having a frequency equal to or higher than a frequency of a millimeter wave (including a submillimeter wave), it is possible to realize a communication line capable of performing high-speed communication in several ten Gbps order, realization of which is difficult in the electric interconnection, while overcoming the problems (the problem of reliability and the problem concerning connection) described above.

Incidentally, in general, it is considered difficult to realize flexibility in a waveguide for transmitting a radio wave having a frequency equal to or higher than a frequency of a millimeter wave (including a submillimeter wave). On the other hand, a technique for realizing such a waveguide having flexibility is also known.

For example, in a method described in Japanese Patent No. 4724849, it is intended to improve flexibility of a waveguide by using an insulative yarn in an inner dielectric and generate a distribution in a dielectric constant and stabilize a transmission characteristic by changing a type of the yarn of the inner dielectric.

In a technique described in Japanese Patent Application Laid-Open Publication No. 8-195605, an external conductor is formed by sticking thin conductors without a gap to achieve both of flexibility and a reduction in a transmission loss.

Further, Japanese Patent Application Laid-Open Publication No. 2015-185858 describes a technique for winding a required number of flat foil yarns, which have a flat sectional shape, around a dielectric in a so-called braid shape to form a flexible waveguide with less transmission loss.

Further, Japanese Patent No. 2800636 describes a technique for forming a flexible waveguide including an external conductor including a bellows section and bendable in the bellows section.

SUMMARY OF THE INVENTION

A waveguide according to an aspect of the present invention includes: a linear dielectric, a dielectric constant of which is uniform in a longitudinal direction and a cross section of which assumes the same shape in the longitudinal direction; and an external conductor disposed in a position covering an outer periphery of the dielectric and formed by a tube having flexibility, the waveguide conducting a radio wave in a frequency band equal to or higher than a frequency band of a millimeter wave or a submillimeter wave near 60 GHz or higher. The external conductor includes a metal layer, the metal layer has a cyclic structure, a shape of an inner periphery side section of which is opposed to the dielectric and forms a cyclic shape displacement member in a waveguide longitudinal direction, and the cyclic structure is a structure satisfying $\lambda mr < \lambda ch$, where $\lambda mr$ represents a center wavelength of a main reflection band due to the cyclic structure and $\lambda ch$ represents a cutoff wavelength in a high-order mode of the waveguide.

An image transmission apparatus according to an aspect of the present invention is an image transmission apparatus including the waveguide, and the waveguide transmits a predetermined image signal.

An endoscope according to an aspect of the present invention is an endoscope including the waveguide, and the waveguide transmits a predetermined image signal.

An endoscope system according to an aspect of the present invention includes: the endoscope; and an image-signal processing circuit configured to apply predetermined image processing to a predetermined image signal transmitted by the waveguide.

BRIEF DESCRIPTION OF THE DRAWINGS

FIG. 51 is a diagram showing a measurement result of a transmission characteristic in a 50 to 75 GHz band in cases of the number of braided strings=16 and 32 in the flexible waveguide in the third embodiment; and FIG. 52 is a diagram showing a measurement result of a transmission characteristic in a 75 to 110 GHz band in the case of the number of braided strings=32 in the flexible waveguide in the third embodiment.

DETAILED DESCRIPTION OF THE PREFERRED EMBODIMENTS

Figure 1:
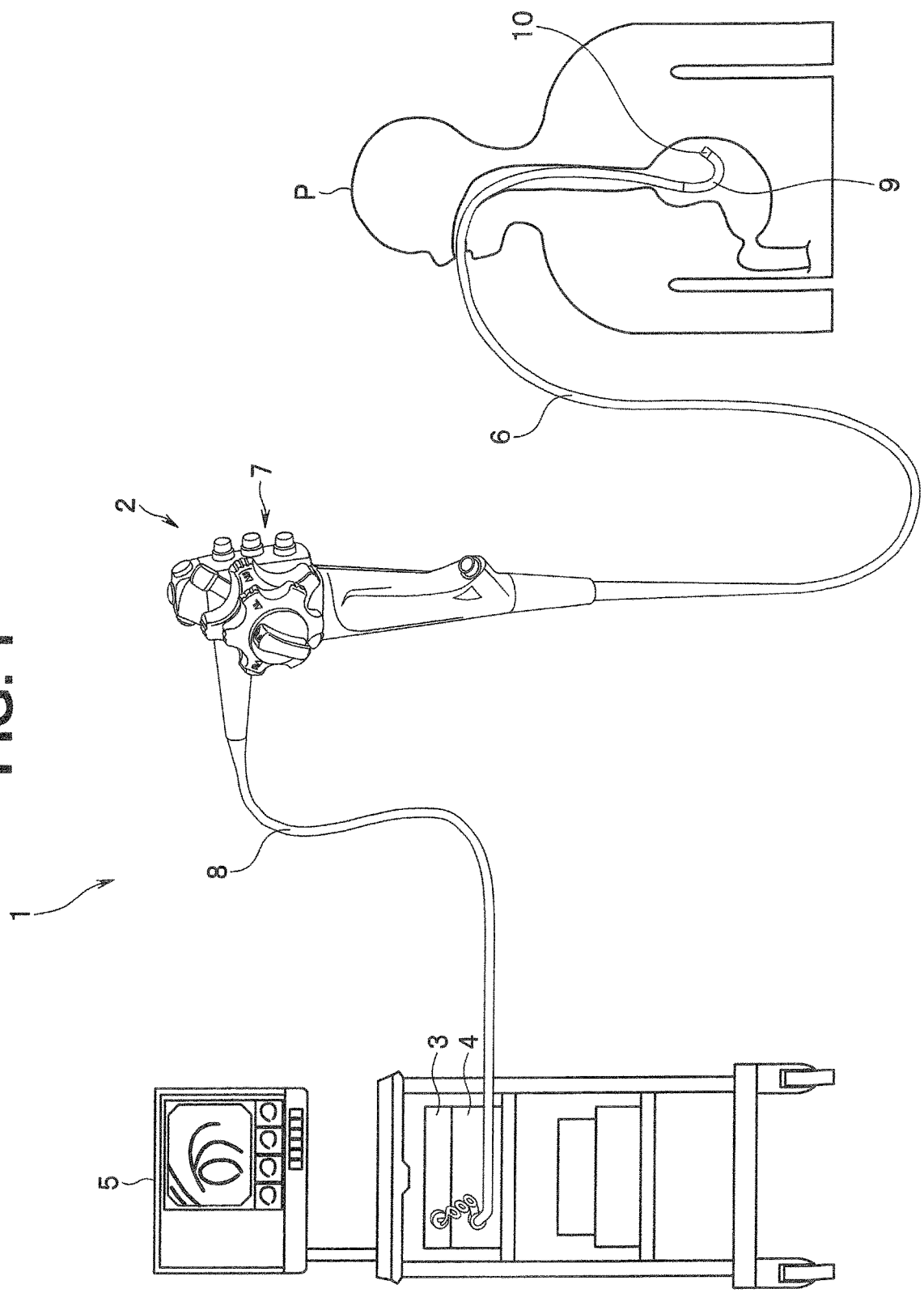
FIG. 1 is a perspective view showing a schematic configuration of an endoscope system including a flexible waveguide in a first embodiment of the present invention.

Embodiments of the present invention are explained below with reference to the drawings.

Note that the respective embodiments explained below are explained using, as examples, endoscope systems including flexible waveguides in the respective embodiments.

The present invention is not limited by the embodiments. Further, in the description of the drawings, the same portions are denoted by the same reference numerals and signs. Furthermore, it needs to be noted that the drawings are schematic and relations between thicknesses and widths of respective members, ratios of the respective members, and the like are different from actual relations, ratios, and the like. Portions having dimensions and ratios different from one another are included among the drawings.

First Embodiment

Figure 2:
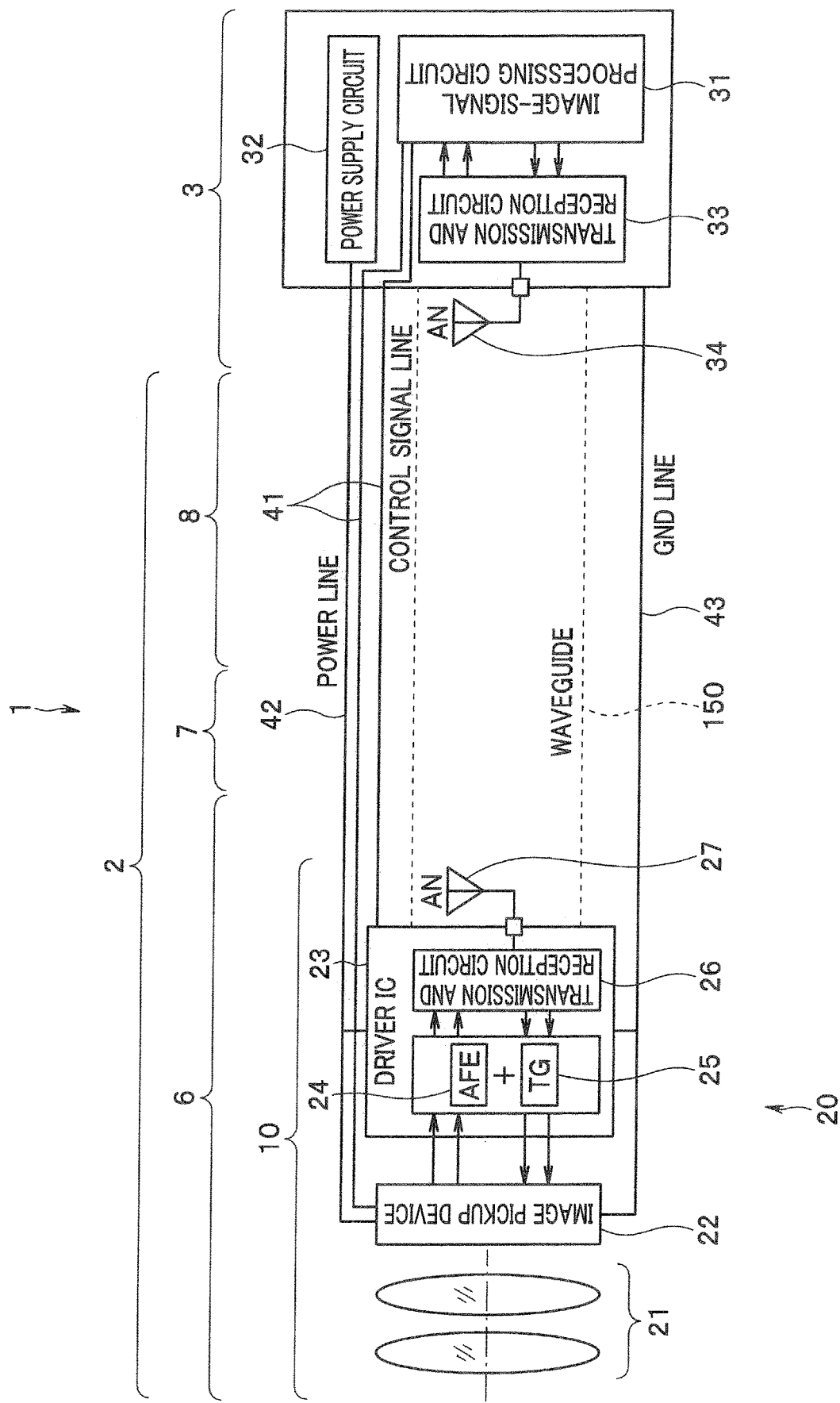
FIG. 2 is a block diagram showing a functional configuration of a main part of the endoscope system according to the first embodiment.

FIG. 1 is a perspective view showing a schematic configuration of an endoscope system including a flexible waveguide in a first embodiment of the present invention. FIG. 2 is a block diagram showing a functional configuration of a main part of the endoscope system according to the first embodiment.

As shown in FIG. 1, an endoscope system 1 is a so-called upper digestive tract endoscope system and mainly includes an endoscope 2 including an image pickup section configured to pick up an intra-body image of a subject P by inserting a distal end portion into a body cavity of the subject P and output an image signal of the subject image, a video processor 3 including an image processing section that applies predetermined image processing to the image signal outputted from the image pickup section in the endoscope 2 and configured to comprehensively control an operation of the entire endoscope system 1, a light source apparatus 4 configured to generate illumination light to be emitted from a distal end of the endoscope 2, and a display apparatus 5 configured to display an image applied with the image processing in the video processor 3.

The endoscope 2 includes an insertion section 6 including the image pickup section at a distal end portion and configured mainly by an elongated shape portion having flexibility, an operation section 7 connected to a proximal end side of the insertion section 6 and configured to receive inputs of various operation signals, and a universal cord 8 extended toward the proximal end side from the operation section 7 and connected to the video processor 3 and the light source apparatus 4.

The endoscope 2 includes a signal transmission line extended, between the image pickup section disposed at the distal end portion of the insertion section 6 and the image processing section in the video processor 3, from the image pickup section in the insertion section 6 to the image processing section of the video processor 3 through respective insides of the insertion section 6, the operation section 7, and the universal cord 8 and for transmitting the image signals and the like outputted from the image pickup section.

In the endoscope system according to this embodiment, the signal transmission line is configured by a waveguide that allows a millimeter wave or submillimeter wave (hereinafter representatively described as millimeter wave depending on a case) to pass (the "waveguide" is explained in detail below).

Referring back to FIG. 1, the insertion section 6 includes a distal end rigid portion 10 disposed at a most distal end portion and incorporating an image pickup device 22 and the like configuring the image pickup section, a bendable bending section 9 disposed on a proximal end side of the distal end rigid portion 10 and configured by a plurality of bending pieces, and a long-shaped flexible tube section connected to a proximal end side of the bending section 9 and having flexibility.

As shown in FIG. 2, at the distal end rigid portion 10 disposed at the most distal end of the insertion section 6 in this embodiment, an image pickup optical system 21 on which a subject image is made incident and an image pickup unit 20 disposed behind the image pickup optical system 21 and including the image pickup device 22 configured to pick up a subject image and output a predetermined image signal through photoelectric conversion are disposed.

The image pickup unit 20 includes the image pickup device 22 provided in a focusing position of the image pickup optical system 21 and configured to receive light condensed by the image pickup optical system 21 and photoelectrically convert the light into an electric signal, a driver IC 23 disposed on a near proximal end side of the image pickup device 22 and configured to drive the image pickup device 22 and apply predetermined processing to an image pickup signal outputted from the image pickup device 22, and a transmission and reception antenna 27 (explained below in detail) provided on the proximal end side of the driver IC 23 and for transmitting and receiving a signal via a waveguide (a flexible waveguide) 150 (explained in detail below).

In this embodiment, as the image pickup device 22, a complementary metal oxide semiconductor (CMOS) image sensor is adopted, the CMOS image sensor being an image sensor having the number of pixels equal to or more than 2 million pixels, which is the number of pixels equivalent to or more than the number of pixels of so-called full high vision.

The driver IC 23 includes an analog frontend (AFE) 24 configured to perform noise reduction and A/D conversion for an electric signal outputted by the image pickup device 22, a timing generator (TG) 25 configured to generate driving timing of the image pickup device 22 and pulses of various kinds of signal processing in the analog frontend (AFE) 24 and the like, a transmission and reception circuit 26 to which the transmission and reception antenna 27 is connected, the transmission and reception circuit 26 being for transmitting and receiving, to and from the image processing section in the video processor 3, a digital signal outputted by the analog frontend (AFE) 24 via the flexible waveguide 150, and a not-shown control section configured to control an operation of the image pickup device 22.

The transmission and reception circuit 26 is a millimeter wave/submillimeter wave communication circuit formed by a so-called monolithic microwave integrated circuit (MMIC).

In the driver IC 23, in this embodiment, all of respective circuits such as the analog frontend (AFE) 24, the timing generator (TG) 25, and the transmission and reception circuit 26 are formed by a silicon CMOS process. The driver IC 23 is sufficiently miniaturized.

The image pickup device 22 and the driver IC 23 are connected via a ceramic substrate 28. A plurality of passive components such as a capacitor 29 are mounted on the ceramic substrate 28 (see FIG. 3 and the like).

On the other hand, the video processor 3 includes an image-signal processing circuit 31 functioning as the image processing section configured to apply predetermined image processing to an image signal outputted from the image pickup unit 20 in the endoscope 2, a power supply circuit 32 configured to generate electric power to be supplied to the image pickup device 22 and the like in the endoscope 2, a transmission and reception circuit 33 for performing transmission and reception of predetermined signals to and from the image pickup unit 20 in the endoscope 2 via the flexible waveguide 150, and a transmission and reception antenna 34 connected to the transmission and reception circuit 33.

Note that the image-signal processing circuit 31 generates control signals (for example, a clock signal and a synchronization signal) for controlling the image pickup device 22 and the driver IC 23 and sends the control signals to the image pickup device 22 and the driver IC 23.

Note that, like the transmission and reception circuit 26, the transmission and reception circuit 33 in the video processor 3 is also formed by a so-called MMIC (monolithic microwave integrated circuit).

As shown in FIG. 2, as explained above, the flexible waveguide 150 functioning as the signal transmission line is internally provided in the insertion section 6, the operation section 7, and the universal cord 8 in the endoscope 2. Various signal lines are disposed on insides of the universal cord 8 and the like in parallel to the flexible waveguide 150.

In other words, in the universal cord 8, as shown in FIG. 2, a control signal line 41 for transmitting various control signals supplied from the image-signal processing circuit 31 in the video processor 3 and a power line 42 and a ground line (GND line) 43 for transmitting electric power supplied from the power supply circuit 32 are respectively disposed.

Predetermined control signals (for example, a clock signal and a synchronization signal) are supplied to the respective circuits in the image pickup device 22 and the driver IC 23 in the endoscope 2 via the control signal line 41.

Similarly, electric power is supplied to the respective circuits in the image pickup device 22 and the driver IC 23 in the endoscope 2 from the power supply circuit 32 of the video processor 3 via the power line 42 and the ground line (GND line) 43.

<Flexible Waveguide, Transmission and Reception Circuit, and Image Pickup Unit>

The waveguide (the flexible waveguide), the transmission and reception circuit, and peripheral circuits (the image pickup unit and the like) of the waveguide and the transmission and reception circuit in the endoscope system according to this embodiment are explained.

The present invention provides a flexible waveguide used in a millimeter wave region (including a submillimeter wave) including a dielectric mixed material appropriately satisfying three conditions of highness of a dielectric constant, smallness of dielectric loss tangent, and appropriate flexibility, an image transmission apparatus including the flexible waveguide, an endoscope including the flexible waveguide, and an endoscope system.

The present invention proposes anew a signal transmission scheme by a waveguide (a flexible waveguide) that allows a millimeter wave or a submillimeter wave (a radio wave having a frequency of approximately 30 to 600 GHz) to pass instead of a signal transmission scheme by a lead wire and a signal transmission scheme by an optical fiber conventionally used as a signal transmission scheme for connecting an image pickup section in the endoscope and an image processing section in a video processor.

Note that, in this embodiment, the millimeter wave and the submillimeter wave indicate a radio wave having a wavelength in a millimeter to submillimeter order (approximately 0.5 to 10 mm).

As shown in FIG. 2, the image pickup unit 20 is disposed behind the image pickup optical system 21 on which a subject image is made incident at the distal end rigid portion 10 disposed at the most distal end of the insertion section 6. As explained above, the image pickup unit 20 includes the image pickup device 22 configured to pick up a subject image and output a predetermined image signal through photoelectric conversion. The waveguide (the flexible waveguide) 150 is extended from the image pickup unit 20 toward an insertion section proximal end side.

As explained above, the image pickup unit 20 includes the image pickup device 22 configured to receive light condensed by the image pickup optical system 21 and photoelectrically convert the light into an electric signal, the driver IC 23 disposed on the near proximal end side of the image pickup device 22 and configured to drive the image pickup device 22 and apply predetermined processing to an image pickup signal outputted from the image pickup device 22, and the transmission and reception antenna 27 provided on the proximal end side of the driver IC 23 and for transmitting and receiving signals via the flexible waveguide 150.

As explained above, the driver IC 23 includes the analog frontend (AFE) 24, the timing generator (TG) 25, the transmission and reception circuit 26, and the not-shown control section. The driver IC 23 is connected to the image pickup device 22 via the ceramic substrate 28.

<Configuration of Flexible Waveguide>

Figure 3:
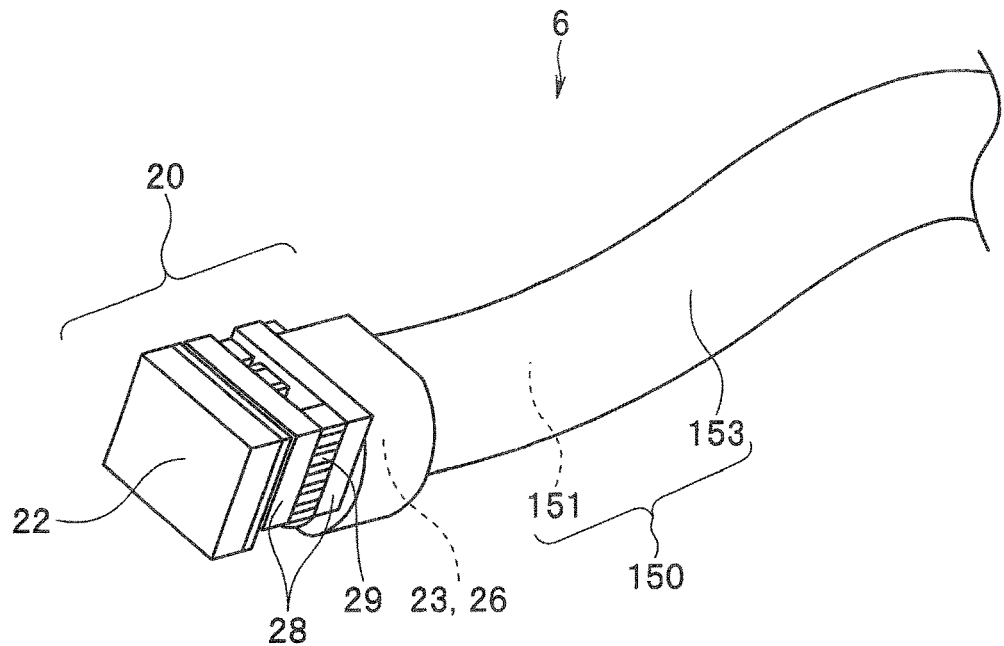
FIG. 3 is a main part enlarged perspective view showing structures of the flexible waveguide and an image pickup unit in the first embodiment.
Figure 4:
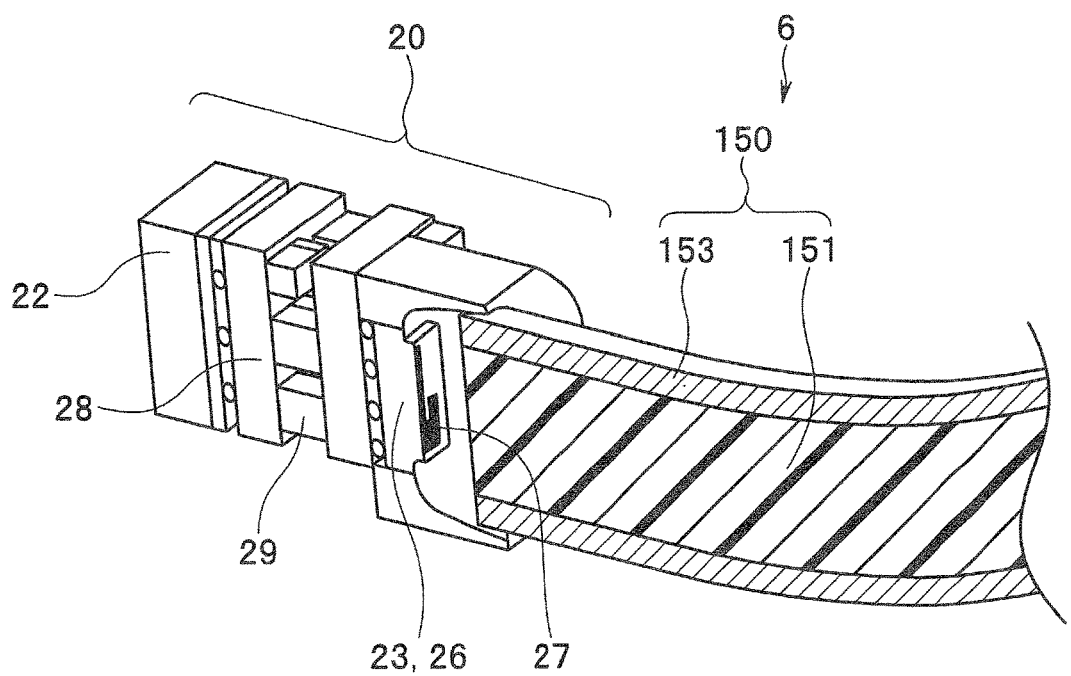
FIG. 4 is a main part enlarged perspective view showing, in a partial cross section, the structures of the flexible waveguide and the image pickup unit in the first embodiment.
Figure 5:
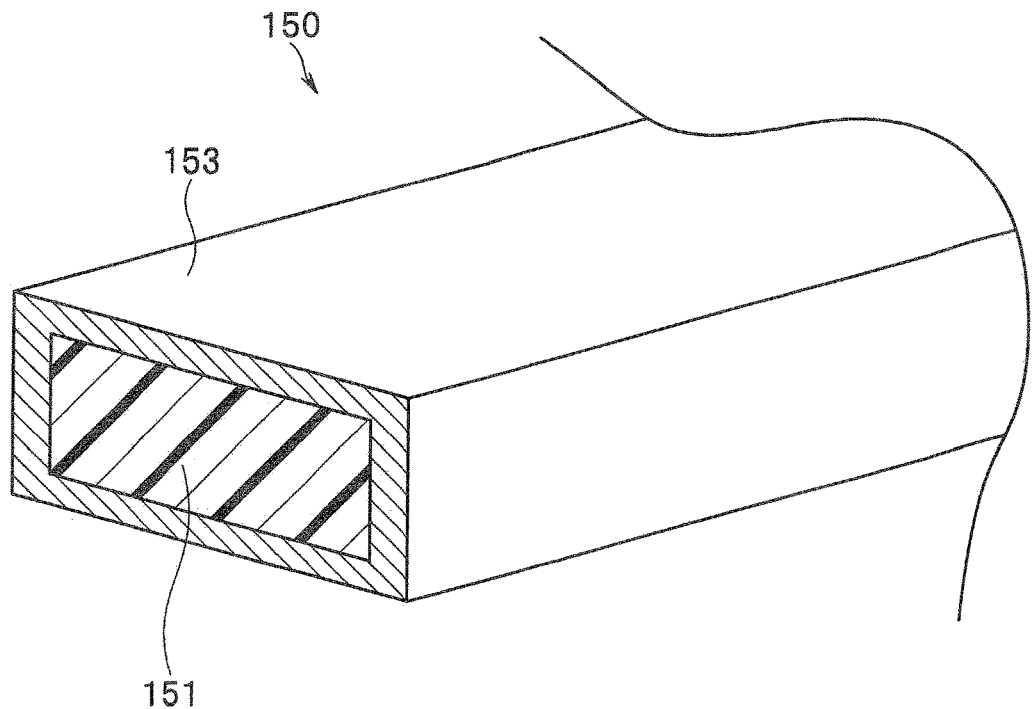
FIG. 5 is a main part enlarged perspective view showing configurations of an external conductor and an inner dielectric relating to the flexible waveguide in the first embodiment.
Figure 6:
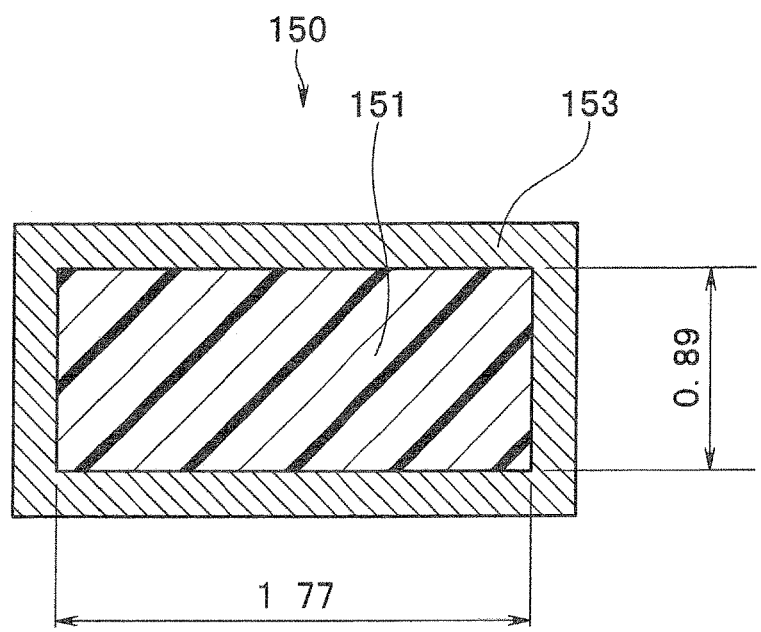
FIG. 6 is a main part enlarged sectional view showing a cross section in a direction perpendicular to a longitudinal axis in the flexible waveguide in the first embodiment.

FIG. 3 is a main part enlarged perspective view showing structures of the flexible waveguide and the image pickup unit in the first embodiment. FIG. 4 is a main part enlarged perspective view showing, in a partial cross section, the structures of the flexible waveguide and the image pickup unit in the first embodiment. FIG. 5 is a main part enlarged perspective view showing configurations of the external conductor and the inner dielectric relating to the flexible waveguide in the first embodiment. FIG. 6 is a main part enlarged sectional view showing a cross section in a direction perpendicular to a longitudinal axis in the flexible waveguide in the first embodiment.

Note that, in FIG. 3 to FIG. 6, an external conductor 153 of the flexible waveguide 150 is represented as having a predetermined thickness. However, the drawings are schematic and a shape of the external conductor 153, relations between thicknesses and widths of the respective members, ratios of the respective members, and the like are different from actual shape, relations, ratios, and the like. In other words, in this embodiment, the external conductor 153 forms a cyclic shape displacement section (shape displacement member) (for example, assumes a bellows shape) in a so-called longitudinal direction. Details are explained below.

As shown in FIG. 3 and FIG. 4, a distal end portion of the flexible waveguide 150 that allows a millimeter wave or a submillimeter wave to pass is connected to the proximal end side of the driver IC 23 across the transmission and reception antenna 27 integrated with a package of the driver IC 23.

The flexible waveguide 150 (hereinafter described as waveguide 150 as well) has flexibility. After a distal end side of the flexible waveguide 150 is connected to the driver IC 23 disposed at the distal end rigid portion 10, the flexible waveguide 150 is extended toward the proximal end side of the insertion section 6.

More in detail, after being inserted through an inside of the insertion section 6 including the bending section 9 and the flexible tube section further on the proximal end side such as the further proximal end side relative to the driver IC 23 in the insertion section 6, that is, a further proximal end side portion relative to a disposition part of the driver IC 23 at the distal end rigid portion 10, the flexible waveguide 150 is inserted through the inside of the operation section 7 and the inside of the universal cord 8 and disposed in a position leading to the video processor 3.

Note that the proximal end side of the flexible waveguide 150 may be connected to the video processor 3 through conversion in a connector provided at one end of the universal cord 8.

The flexible waveguide 150 is a signal transmission line connecting the image pickup unit 20 and the image processing section (the image processing circuit 31) in the video processor 3. At least a part of the flexible waveguide 150 is a waveguide for propagating a millimeter wave or a submillimeter wave.

<Inner Dielectric and External Conductor in Flexible Waveguide>

In this embodiment, the flexible waveguide 150 includes a linear inner dielectric 151, a dielectric constant of which is uniform in the longitudinal direction and a cross section of which assumes the same shape in the longitudinal direction, and the external conductor 153, which is a metal layer, disposed in a position covering an outer periphery of the inner dielectric 151 and formed by a tube having flexibility.

The inner dielectric 151 has a sectional shape, a ratio of a long side and a short side of which is constant in the longitudinal direction. More specifically, as shown in FIG. 6, the inner dielectric 151 assumes a rectangular shape having a long side and a short side, and a long side $a_1$ is set to 1.77 mm and a short side $b_1$ is set to 0.89 mm. In this embodiment, a specific dielectric constant $\varepsilon_r$ of the inner dielectric 151 is set to 4.5.

Incidentally, in this embodiment, "a dielectric constant is uniform" means that the dielectric constant is uniform in terms of a dimension in a wavelength order of a radio wave (a millimeter wave or a submillimeter wave) propagating inside the waveguide. In other words, a dielectric constant distribution by a structure having a dimension different from the wavelength order by one to two or more digits does not affect the radio wave propagating inside the waveguide. Therefore, in this embodiment, this is included in the representation "a dielectric constant is uniform".

Note that, in this embodiment, for the inner dielectric 151, use of a dielectric mixed material obtained by mixing a resin material (nonpolar resin such as PTFE) serving as a base material and a crystal material (a powdered crystal material having a small dielectric loss such as α-alumina) is assumed. In this case, a dielectric material to be mixed is far smaller than the wavelength. Consequently, a difference between dielectric constants of the resin material and the crystal material or a fine structure does not affect a radio wave inside the waveguide. Only an averaged dielectric constant affects a transmission characteristic.

On the other hand, the external conductor 153 includes a predetermined metal layer section disposed to cover an outer peripheral portion of the inner dielectric 151. Electric conductivity of the metal layer section is set to $59 \times 10^6$ S/m equivalent to electric conductivity of pure copper. Note that although the electric conductivity is uniquely determined here, in the present invention, the electric conductivity of the metal layer section is not limited to this. In the embodiment, it is desirable to use a metal layer having high electric conductivity. In this embodiment, the external conductor 153 has a characteristic configuration forming a cyclic shape displacement section. The configuration is explained in detail below.

Note that, in this embodiment, as explained above, the inner dielectric 151 is configured by the dielectric having the specific dielectric constant $\varepsilon_r$=4.5. However, the inner dielectric in the flexible waveguide 150 may include, for example, as shown in FIG. 7 and FIG. 8, a first dielectric 151A located relatively on an inner side in a cross section perpendicular to the longitudinal axis and a second dielectric 152A located further on an outer side relative to the first dielectric 151A in the cross section perpendicular to the longitudinal axis (and disposed to cover an entire periphery of an outer peripheral portion of the first dielectric 151A) and having a dielectric constant lower than a dielectric constant of the first dielectric 151A.

Figure 7:
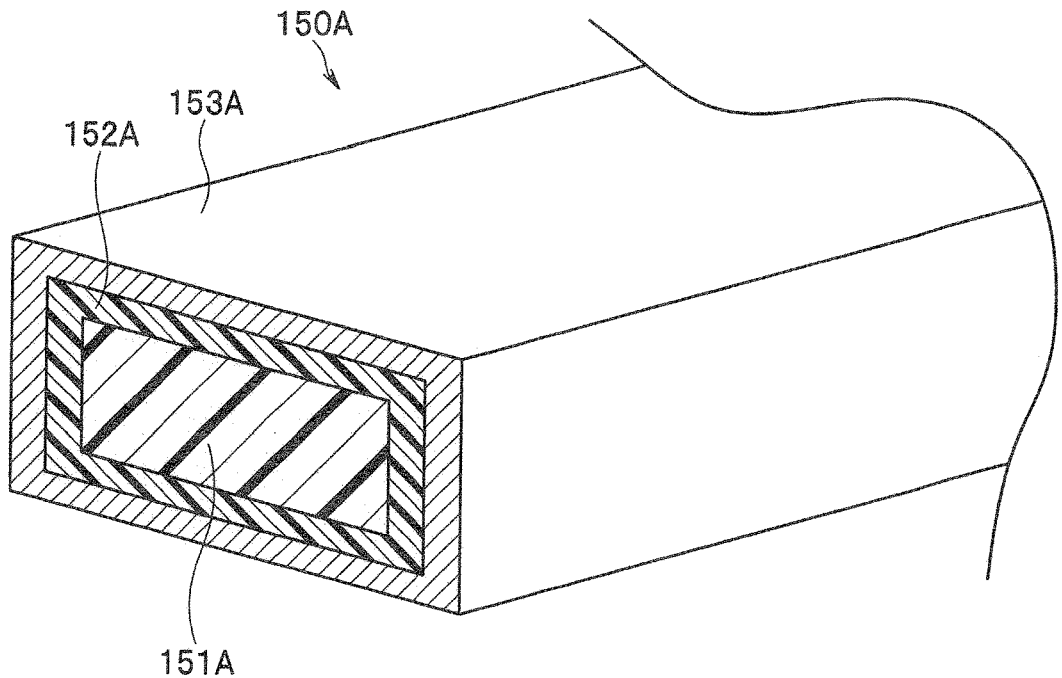
FIG. 7 is a main part enlarged perspective view showing configurations of an external conductor and an inner dielectric relating to a flexible waveguide according to a first modification of the first embodiment.

FIG. 7 is a main part enlarged perspective view showing configurations of an external conductor and an inner dielectric relating to a flexible waveguide according to a first modification of the first embodiment. FIG. 8 is a main part enlarged sectional view showing a cross section in a direction perpendicular to the longitudinal axis in the flexible waveguide according to the first modification of the first embodiment.

Note that, in this modification, an external conductor 153A is disposed in a position covering an outer periphery of the dielectric (the first dielectric 151A and the second dielectric 152A). In this modification, the first dielectric 151A has a sectional shape, a ratio of a long side and a short side of which is constant in the longitudinal direction. The second dielectric 152A is disposed in a region sandwiched between the first dielectric 151A and the external conductor 153A, which is the metal layer.

Figure 8:
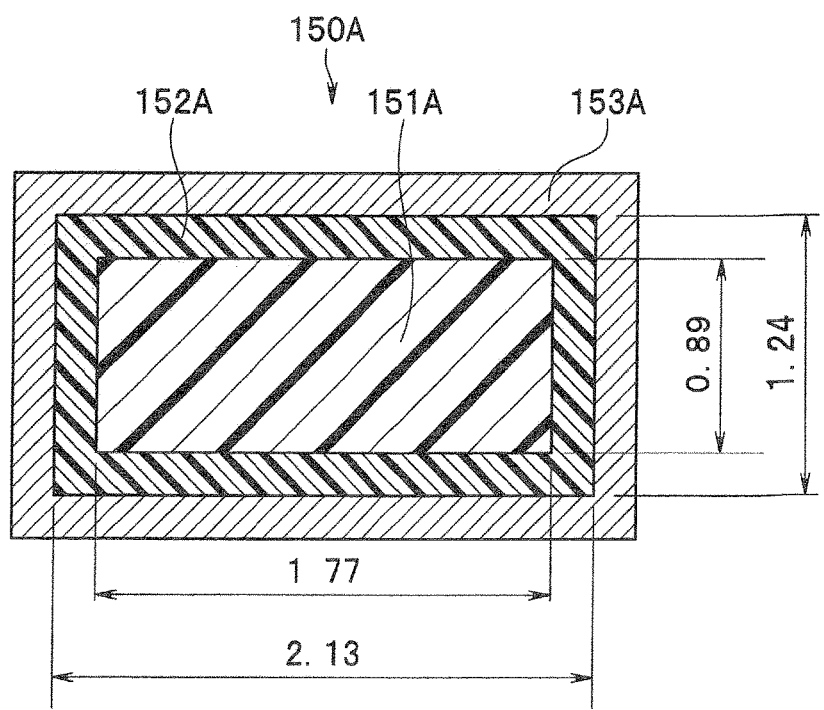
FIG. 8 is a main part enlarged sectional view showing a cross section in a direction perpendicular to a longitudinal axis in the flexible waveguide according to the first modification of the first embodiment.

As shown in FIG. 7 and FIG. 8, in a flexible waveguide 150A in this modification, specific dielectric constants of the first dielectric 151A and the second dielectric 152A are respectively set to concerning the first dielectric 151A, a specific dielectric constant $\varepsilon_{r1}$=4.5 and concerning the second dielectric 152A, a specific dielectric constant $\varepsilon_{r2}$=1.4.

In this way, in this modification, the specific dielectric constant $\varepsilon_{r1}$ of the first dielectric 151A is set to 3 or more and the specific dielectric constant $\varepsilon_{r2}$ of the second dielectric 152A is set to 2 or less.

Sectional shapes perpendicular to the longitudinal axis in the first dielectric 151A and the second dielectric 152A are respectively as follows. First, the first dielectric 151A assumes a rectangular shape having a long side and a short side and are respectively set to a long side $a_1$=1.77 mm and a short side $b_1$=0.89 mm.

The second dielectric 152A is a tube covering the outer peripheral portion of the first dielectric 151A. A center of the first dielectric 151A is arranged on an inner side of the second dielectric 152A.

An inner peripheral portion of the second dielectric 152A is set to a long side $a_1$=1.77 mm and a short side $b_1$=0.89 mm.

An outer peripheral portion of the second dielectric 152A is set to a long side $a_2$=2.13 mm and a short side $b_2$=1.24 mm.

<Characteristics of Inner Dielectric>

Characteristics (effects) of the inner dielectric 151 (and the first dielectric 151A and the second dielectric 152A in the flexible waveguide 150A in the modification) disposed on an inside of the flexible waveguide 150 in this embodiment are explained.

In the flexible waveguide 150 in this embodiment, as explained above, the inner dielectric 151 has the sectional shape, a ratio of the long side and the short side of which is constant in the longitudinal direction. In other words, the sectional shape, the ratio of the long side and the short side of which is constant, is stably extended in the longitudinal direction. A transmission mode of a radio wave transmitted inside the dielectric stabilizes.

Further, in the flexible waveguide 150, since the sectional shape, the ratio of the long side and the short side of which is constant, is stably extended in the longitudinal direction in the inner dielectric 151 as explained above, there is an effect that, even if the waveguide itself is bent by an external force applied from an outside, an increase in a transmission loss due to the bend is suppressed and, as a result, a transmission loss amount stabilizes.

In the flexible waveguide 150A in the modification explained above, the second dielectric 152A has the dielectric constant lower than the dielectric constant of the first dielectric 151A. In other words, since the dielectric constant of the first dielectric 151A is higher than the dielectric constant of the second dielectric 152A and since the second dielectric 152A is disposed to cover the entire periphery of the outer peripheral portion of the first dielectric 151A, it is possible to confine, in the first dielectric 151A, energy of an electromagnetic wave transmitted in the flexible waveguide 150A.

As a result, in the flexible waveguide 150A in this modification, it is possible to suppress occurrence of a transmission loss due to the external conductor 153A, which is the metal layer.

Note that other configurations and action effects concerning the first dielectric 151A and the second dielectric 152A in the flexible waveguide 150A in the modification are the same as configurations and action effects of a first dielectric and a second dielectric described in Japanese Patent Application No. 2016-247031 filed earlier by the inventor. Therefore, detailed explanation of the other configurations and action effects is omitted here.

<Occurrence Principle of Reflection Band in Waveguide in which Cyclic Unevenness is Formed>

Concerning the present invention, a principle of occurrence of a reflection band in the waveguide in which the cyclic unevenness is formed is explained with reference to FIG. 9 to FIG. 18.

<Theory of Multilayer Film Interference Relating to Optical Multilayer Film>

Figure 9:
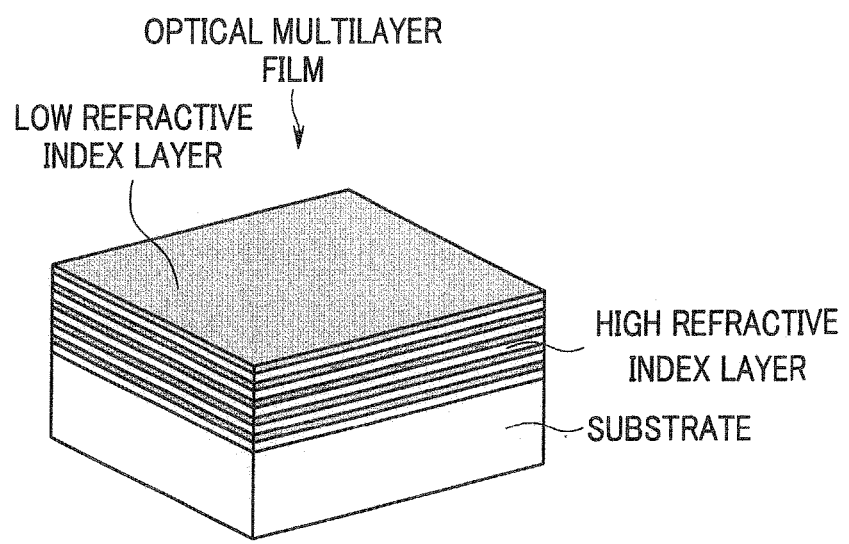
FIG. 9 is an explanatory diagram for explaining, concerning the present invention, a principle of occurrence of a reflection band in a waveguide in which cyclic unevenness is formed and is a main part sectional perspective view showing a configuration example of an optical multilayer film concerning multilayer film interference.
Figure 10:
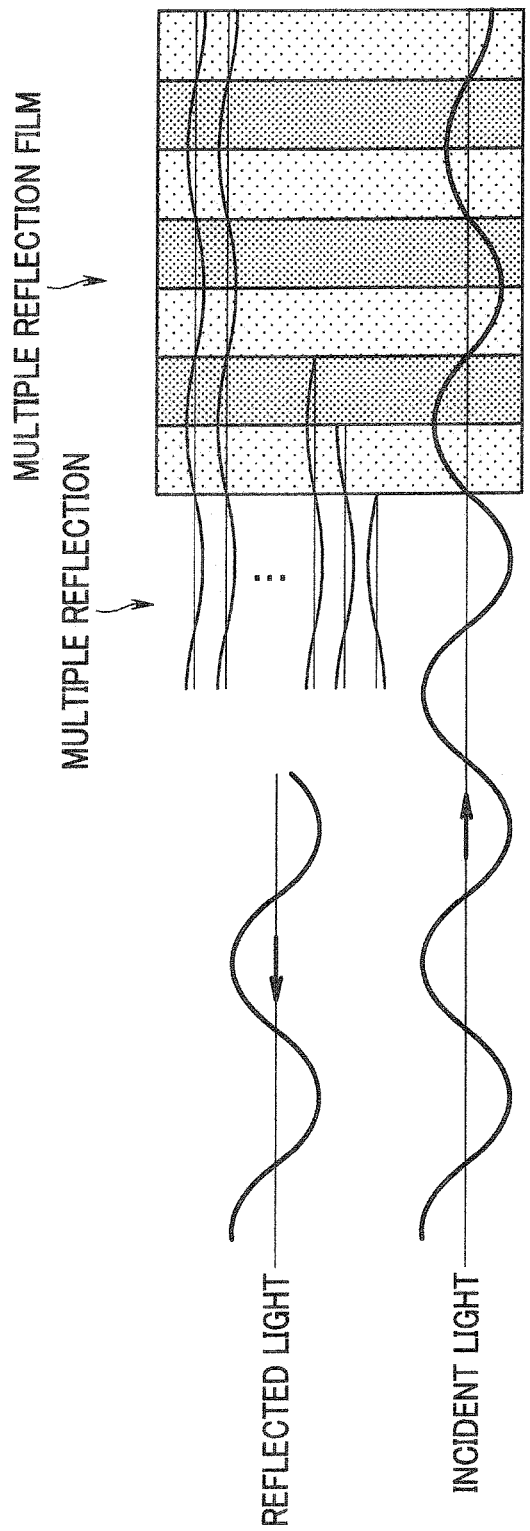
FIG. 10 is an explanatory diagram for explaining, concerning the present invention, the principle of occurrence of the reflection band in the waveguide in which the cyclic unevenness is formed and is a diagram showing multiple reflection at the time when predetermined incident light is made incident on a multilayer reflection film.

First, FIG. 9 is an explanatory diagram for explaining, concerning the present invention, a principle of occurrence of a reflection band in the waveguide in which the cyclic unevenness is formed and is a main part sectional perspective view showing a configuration example of an optical multilayer film concerning multilayer film interference. FIG. 10 is an explanatory diagram for explaining, concerning the present invention, the principle of occurrence of the reflection band in the waveguide in which the cyclic unevenness is formed and is a diagram showing multiple reflection at the time when predetermined incident light is made incident on a multilayer reflection film.

As explained above, "cyclic unevenness or creases that occur on an inner surface of a metal layer or cyclic gaps (braiding holes) markedly increase a transmission loss" is a matter found by the inventor and pointed out for the first time in Japanese Patent Application No. 2016-247031. First, this point is supplementarily explained.

In the first place, in those skilled in the art, although a waveguide in a microwave to millimeter wave band is a well-known transmission line, the waveguide was recognized as a line difficult to be used and was used only for a use for which there is no other alternative. In particular, in a millimeter wave band or a higher frequency band, a transmission loss increases only due to unevenness including scratches on an inside of the waveguide. Therefore, measures such as polishing of the inside of the waveguide are adopted. As a result, it is generally recognized that the "waveguide" is an "expensive transmission line".

Under such circumstances, the inventor repeated researches in view of a point "low-loss transmission is possible by a technique described in Japanese Patent Application Laid-Open Publication No. 2015-185858 in a microwave band". As a result, the inventor reached an inference "reflection of a very small wave occurs in cyclic unevenness or creases that occur on an inner surface of the metal layer or cyclic gaps (braiding holes) and multiple reflection of the very small wave might be a cause of transmission characteristic deterioration" and "this phenomenon suddenly increases an effect of the phenomenon in a millimeter wave band and hinders waveguide use in the millimeter wave band".

In the inference, an analogy with a phenomenon "multilayer film interference" in multiple interference of a wave is considered. Incidentally, the multilayer film interference is, as indicated by the name, a phenomenon observed in an optical multilayer film obtained by multiply laminating thin films having different refractive indexes shown in FIG. 9 (an optical multilayer film obtained by laminating a high refractive index layer and a low refractive index layer on a predetermined base material as shown in FIG. 9) and is a phenomenon known in an optical field.

When light having a wavelength approximately equivalent to thickness of such an optical multilayer film is made incident on the optical multilayer film (as an example, a film obtained by superimposing, with cyclicity, dielectric films having different refractive indexes as shown in FIG. 10), the light is reflected and transmitted respectively on respective interfaces of the thin films having the different refractive indexes, and the reflected and transmitted light (as a wave) generates an interference effect, whereby the multilayer film interference can occur (see FIG. 10). In other words, multiple reflection occurs when a film thickness (an optical path length) is $\lambda/4$.

According to teaching of this theory of the multilayer film interference, the light (the wave) reflected and transmitted respectively on the respective interfaces of the thin films generates a large reflection band (a main reflection band) at a wavelength $\lambda r$ given by the following Equation (1) because $\lambda/4 = L1/2$, where "L1" represents a lamination cycle of the thin films to be laminated.

$$\lambda r = 2 \times L1 \qquad \text{Equation (1)}$$

where $L1 = n_L \times d_L + n_H \times d_H$, $n_L$: a refractive index of a low refractive index layer thin film, $n_H$: a refractive index of a high refractive index layer thin film, $d_L$: thickness of the low refractive index layer thin film, and $d_H$: thickness of the high refractive index layer thin film.

In Equation (1), "the refractive index and the thickness are multiplied together" because conversion is performed considering that a wavelength of the light (the wave) decreases inside a substance. Note that a detailed theory is omitted and will be described in a published book.

Note that it is also well-known in the optical field that a fine reflection band also occurs around a frequency band of the "reflection band" or the "reflection band" has a reflection band, which is a harmonic component thereof, (a reflection band that occurs at an integer-times frequency, that is, a wavelength divided by an integer; hereinafter referred to as a "high-order reflection band").

In a narrower technical field (an optical thin film field) in the optical field, it is known that, when an optical multilayer film has a more complicated laminated structure, a reflection band can be formed in a wavelength band an integer times as large as the main reflection band and the high-order reflection band (this "reflection band" is hereinafter referred to as a "low-order reflection band" as opposed to the high-order reflection band). Note that the formation of the "low-order reflection band" is explained in detail in Japanese Patent Application Laid-Open Publication No. 2011-242237 proposed earlier by the inventor. Detailed explanation of the formation of the "low-order reflection band" is omitted here but is explained below in this specification.

<Effectiveness of Avoiding Influence of Reflection Band in Waveguide in which Cyclic Unevenness is Formed>

"The theory of the multilayer film interference relating to the optical multilayer film" is explained above. "Effectiveness of avoiding influence of the reflection band in the waveguide in which the cyclic unevenness is formed" characterizing the present invention is explained with reference to the theory of the multilayer film interference.

Figure 11:
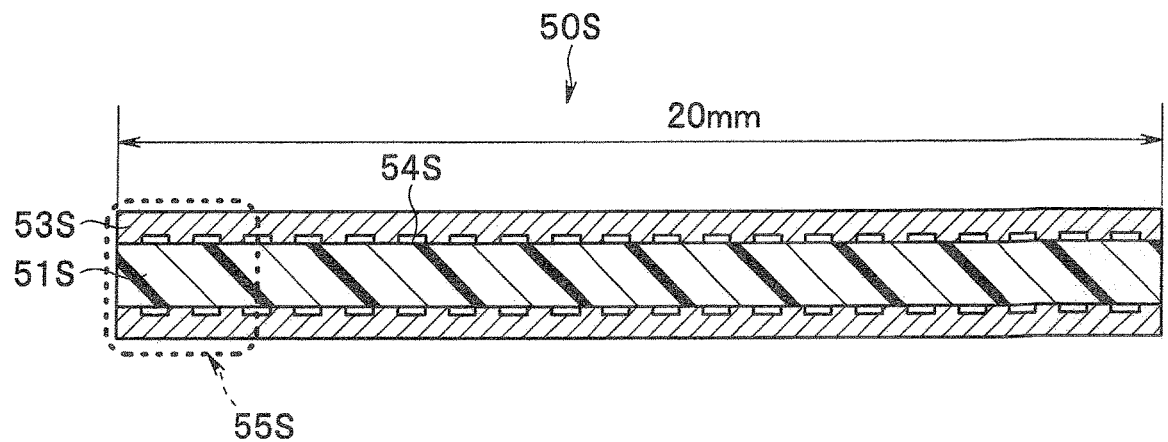
FIG. 11 is an explanatory diagram for explaining, concerning the present invention, a phenomenon of occurrence of a reflection band in a waveguide in which cyclic unevenness is formed and a main part enlarged sectional view showing a longitudinal cross section in a longitudinal direction of a simulation model of the waveguide.
Figure 12:
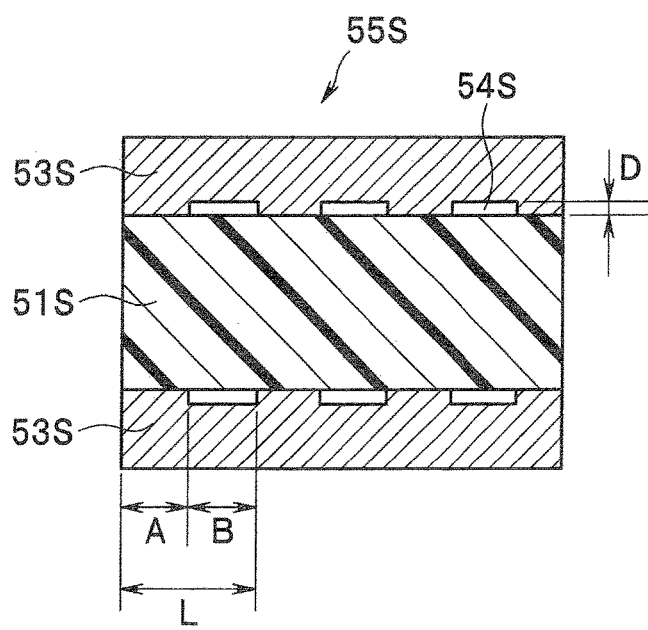
FIG. 12 is an explanatory diagram for explaining, concerning the present invention, the phenomenon of occurrence of the reflection band in the waveguide in which the cyclic unevenness is formed and is a main part enlarged sectional view enlarging and showing a position of the longitudinal cross section in the longitudinal direction of the simulation model of the waveguide.

FIG. 11 is an explanatory diagram for explaining, concerning the present invention, a phenomenon of occurrence of the reflection band in the waveguide in which the cyclic unevenness is formed and is a main part enlarged sectional view showing a longitudinal cross section in the longitudinal direction of a simulation model of the waveguide. FIG. 12 is an explanatory diagram for explaining, concerning the present invention, the phenomenon of occurrence of the reflection band in the waveguide in which the cyclic unevenness is formed and is a main part enlarged sectional view enlarging and showing a position of the longitudinal cross section in the longitudinal direction of the simulation model of the waveguide. Further, FIG. 13 is an explanatory diagram for explaining, concerning the present invention, the phenomenon of occurrence of the reflection band in the waveguide in which the cyclic unevenness is formed and is a diagram showing multiple reflection at the time when predetermined incident light is made incident on the waveguide.

For example, as shown in FIG. 11, a simulation model in which simple unevenness is formed on an inside of a waveguide is assumed. In FIG. 11, a waveguide 50S includes a linear inner dielectric 51S, a dielectric constant of which is uniform in the longitudinal direction and a cross section of which assumes the same shape in the longitudinal direction, and an external conductor 53S, which is a metal layer, disposed in a position covering an outer periphery of the inner dielectric 51S and formed by a substantial tube having flexibility. In the model, it is assumed that cyclic unevenness 54S is formed on an inner peripheral surface of the external conductor 53S.

On the other hand, FIG. 12 is a main part enlarged sectional view enlarging and showing a predetermined part 55S in the simulation model of the waveguide 50S. Note that, as shown in FIG. 12, the unevenness 54S in the simulation model of the waveguide 50S is formed to have cyclicity with acyclic length L=0.66 mm to 2.0 mm A specific dielectric constant εr of the inner dielectric 51S is set to 2.0.

Figure 13:
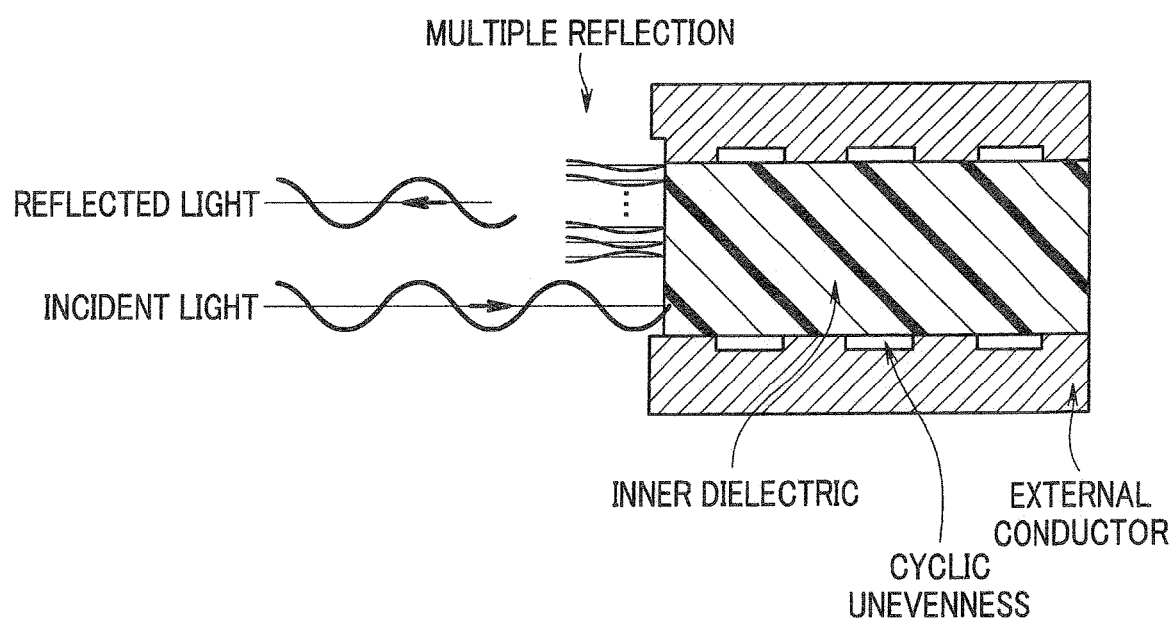
FIG. 13 is an explanatory diagram for explaining, concerning the present invention, the phenomenon of occurrence of the reflection band in the waveguide in which the cyclic unevenness is formed and a diagram showing multiple reflection at the time when predetermined incident light is made incident on the waveguide.

When predetermined incident light is made incident on the waveguide in which the cyclic unevenness is formed shown in FIG. 11 and FIG. 12, multiple reflection is considered to occur as shown in FIG. 13 according to the example of the multilayer film interference explained above (see FIG. 10). A cyclic length equivalent to "L1" in Equation (1) known in the multilayer film interference can be defined as the cyclic length L of the unevenness as shown in FIG. 12.

For example, when the cyclic length L of the cyclic unevenness MS is set to 0.98 in this model and a wavelength $\lambda r$ at which a reflection band is formed is calculated according to Equation (1) as follows:

$$\lambda r = 2 \times L1 = 2 \times 0.98 \times \sqrt{(2.0)} = 2.77 \text{ mm}$$

where L1=unevenness cyclic length L×√(a dielectric constant of the inner dielectric).

The unevenness cyclic length L and √(dielectric constant of the inner dielectric) in the definition of "L1" described above are defined according to the definition of "L1" of Equation (1) from an analogy with the multilayer film interference theory. The unevenness cyclic length L is equivalent to thickness of a thin film in the multilayer film model. √(a dielectric constant of the inner dielectric) is equivalent to a refractive index in the multilayer film model. Note that a relation between the refractive index and the dielectric constant conforms to a relation taught by an electromagnetic theory. The wavelength $\lambda r = 2.77$ mm, which is a calculation result by the above equation, is equivalent to 108 GHz in terms of a frequency.

The inventor carried out a transmission characteristic simulation, in which an electromagnetic field simulator is used, using the simulation model shown in FIG. 11 and FIG.

Figure 14:
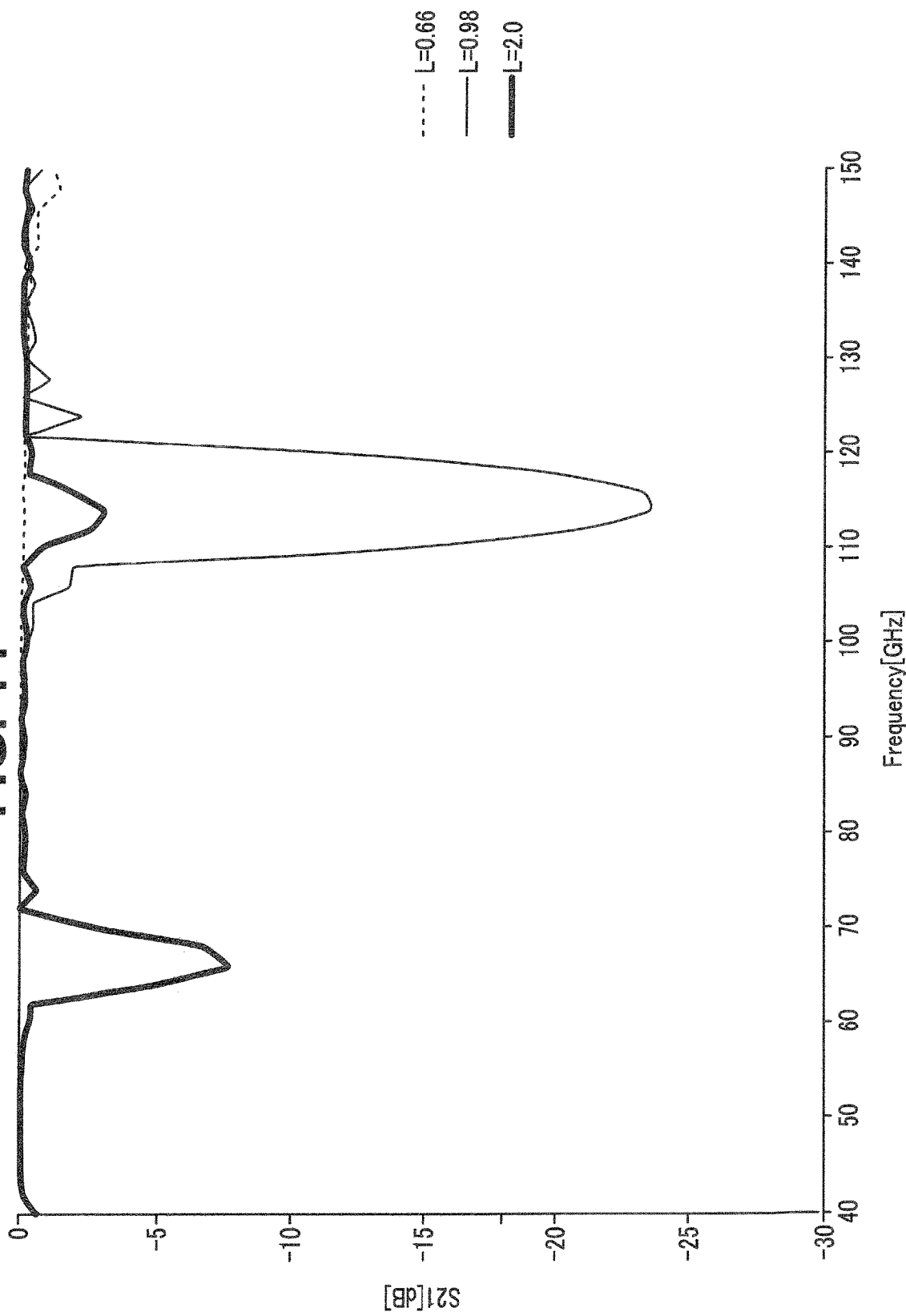
FIG. 14 is a diagram showing, concerning the present invention, a transmission characteristic of the simulation model relating to the waveguide in which the cyclic unevenness is formed.

12. FIG. 14 is a diagram showing, concerning the present invention, a transmission characteristic of a simulation model relating to the waveguide in which the cyclic unevenness is formed.

As indicated by a characteristic line indicated by "cyclic length L=0.98" in FIG. 14, it turns out that, in the simulation model, a reflection band is formed near a wavelength (generally centering on 115 GHz) predicted from Equation (1) described above.

This simulation result supports an inference that a reflection band (a main reflection band) is formed because of the cyclic unevenness MS formed on an inside of the waveguide 50S.

Incidentally, characteristic lines indicated by "cyclic length L=2.0" and "cyclic length L=0.66" in FIG. 14 are respectively results obtained by performing simulations when the cyclic length L of the cyclic unevenness inside the waveguide is 2.0 mm and 0.66 mm.

When the wavelength $\lambda r$ at which the reflection band is formed is calculated according to Equation (1) when the cyclic length L of the cyclic unevenness is 2.0 mm and 0.66 mm, the following results are obtained:

$\lambda r=2\times2.0\times\sqrt{(2.0)}=5.66$ mm (equivalent to 53.0 GHz)

$\lambda r=2\times0.66\times\varepsilon(2.0)=1.87$ mm (equivalent to 160.7 GHz)

According to the simulation result in FIG. 14, for example, in the case of L=2.0 mm, it turns out that, in calculation, a reflection band that should be formed at a center frequency 53 GHz according to Equation (1) is generally formed centering on a frequency 66 GHz according to the simulation result.

In this way, there is deviation of a wavelength of approximately 13 GHz in the center frequency between the reflection band in calculation and the simulation result. This can be explained by a phenomenon in which a wavelength of a radio wave deviates inside the waveguide (the deviating wavelength is referred to as an intra-tube wavelength $\lambda g$) in the waveguide theory. In other words, according to the waveguide theory, it is correct to treat the wavelength $\lambda r$ derived in the above equation as the wavelength $\lambda g$ on the inside of the waveguide.

When a cutoff wavelength in the waveguide (a wavelength uniquely determined by a shape and a configuration of the waveguide; an electromagnetic wave longer than the wavelength cannot be present inside the waveguide: hereinafter referred to as cutoff wavelength as well) is represented as $\lambda c$ and a wavelength in a free space is represented as $\lambda$, a relation between the cutoff wavelength $\lambda c$ and the wavelength $\lambda$ is given by the following equation:

$1/\lambda g^2 = 1/\lambda^2 - 1/\lambda c^2$  Equation (2)

where $\lambda g = \lambda r$.

The wavelength $\lambda$ in the free space is calculated as follows from the relational equation considering that the cutoff wavelength $\lambda c$ in the waveguide of the simulation model is 7.52 mm:

$\lambda = \lambda g/\sqrt{(1+(\lambda g/\lambda c)^2)} = 4.52$ mm (equivalent to 66.4 GHz), which coincides with the simulation result shown in FIG. 14.

Incidentally, it can be confirmed with a similar way of thinking that $\lambda r$ calculated with the cyclic length L of the cyclic unevenness 54S set to 0.98 and the simulation result shown in FIG. 14 more strictly coincide.

On the other hand, in the case of the cyclic length L=0.66 mm, it turns out that a reflection band is present in 160 GHz outside a range of the simulation. Therefore, it can be assumed that disorder of a waveform present near 150 GHz of the simulation result is a skirt of the reflection band that occurs in the 160 GHz band.

It turns out from these simulation results that the prediction of the reflection band formation by Equation (1) and the simulation results coincide. In other words, the inference "reflection of a very small wave occurs in cyclic unevenness or creases that occurs on an inner surface of the metal layer or cyclic gaps (braiding holes) and multiple reflection of the very small wave is a cause of transmission characteristic deterioration" explained above is correct. It can be said that behavior of the multiple reflection of the very small wave can be predicted by an analogy with the multilayer film interference including Equation (1) (at least approximately).

An electromagnetic wave that can be present inside the waveguide is supplemented according to the waveguide theory.

In general, a peculiar transmission mode is present in an electromagnetic wave inside the waveguide according to a form of an electromagnetic field that transmits the inside of the waveguide. In the transmission mode, there are a TE wave not having an electric field component in a traveling direction and a TM wave not having a magnetic field component in the traveling direction. Modes of the TE wave and the TM wave can be respectively defined by a mode number m defined in a waveguide short side direction and a mode number n defined in a waveguide long side direction. For example, in the square waveguide shown in FIG. 11 and FIG. 12, transmission modes shown in FIG. 15 can be present.

Figures 15, 16, 17:
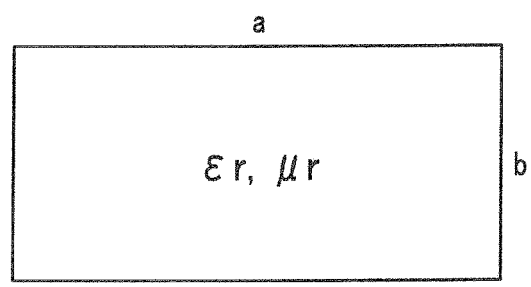
FIG. 15 is a table diagram showing, concerning the present invention, an example of a transmission mode of a square waveguide used for explaining a transmission mode relating to the waveguide in which the cyclic unevenness is formed.
FIG. 16 is a diagram showing, concerning the present invention, a long side-short side relation at the time when dimensions of the waveguide in which the cyclic unevenness is formed is calculated.
FIG. 17 is a table diagram showing, concerning the present invention, an example of a cutoff wavelength in a simulation model relating to the waveguide in which the cyclic unevenness is formed.

Cutoff wavelengths in these transmission modes are given by the following equation:

$$\lambda c = \frac{2\sqrt{\varepsilon r \mu r}}{\sqrt{\left(\frac{m}{a}\right)^2 + \left(\frac{n}{b}\right)^2}} [m] \quad \text{Equation (3)}$$

where "a" represents a long side of the waveguide, "b" represents a short side of the waveguide, $\varepsilon r$ represents a specific dielectric constant of the inner dielectric, $\mu s$ represents specific magnetic permeability of the inner dielectric, m represents a mode number in a waveguide short side direction, and n represents a mode number in a waveguide long side direction as shown in FIG. 16.

Among many transmission modes, a TE 10 mode, which is a mode having a longest cutoff wavelength, is called basic mode. It is known that a value of use of the basic mode is high because, for example, it is easy to reduce a transmission loss in a wavelength range until a mode having a shorter cutoff wavelength (a high-order mode) appears (that is, while only the basic mode can be present).

For example, when cutoff wavelengths of the respective transmission modes are calculated using the simulation model shown in FIG. 11 and FIG. 12 as an example, a result shown in a table of FIG. 17 is obtained. In other words, a wavelength band having a high value of use in the simulation model shown in FIG. 11 and FIG. 12 is a wavelength band of 3.8 to 7.5 mm (a band of 40 to 80 GHz in terms of a frequency).

The following two facts can be derived from the above explanation:

(a) A waveguide having a cyclic structure such as cyclic unevenness on an inner surface of a metal layer (an external conductor) has a "reflection band" due to the cyclic structure, and (b) The waveguide has a high value of use between the cutoff wavelength of the basic mode and the cutoff wavelength of the high-order mode.

Figure 18:
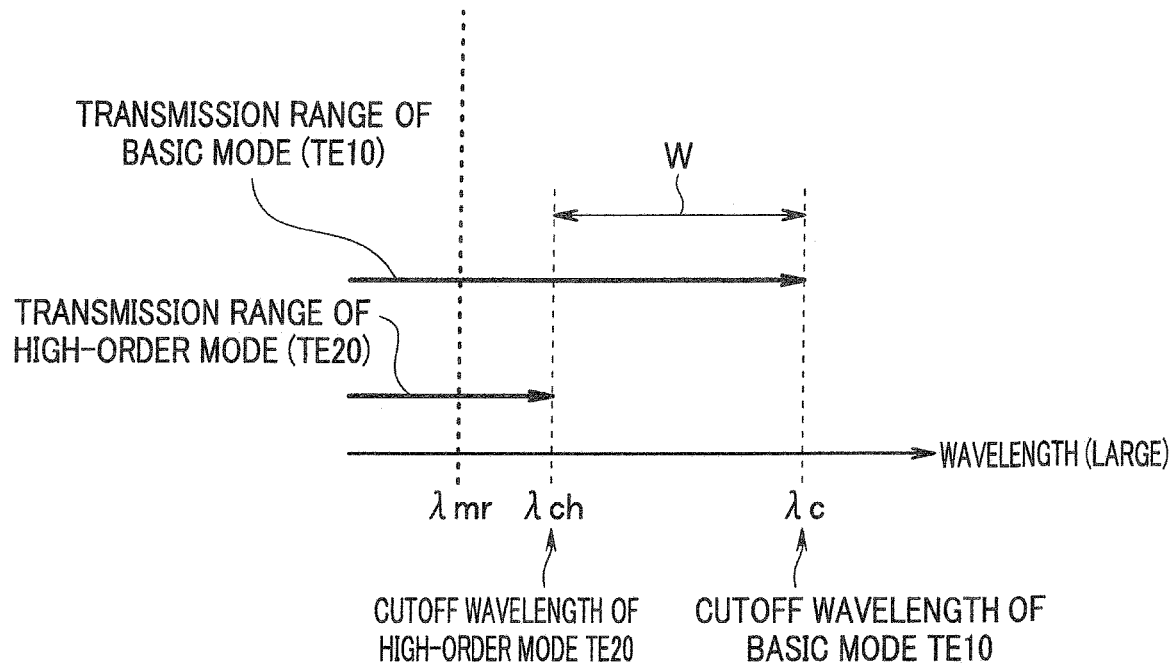
FIG. 18 is a diagram showing, concerning the present invention, a relation between cutoff wavelengths and reflection bands in a basic mode and a high-order mode in the simulation model relating to the waveguide in which the cyclic unevenness is formed.

When these two facts are taken into consideration together, as shown in FIG. 18, it is derived that a center wavelength $\lambda r$ of the reflection band due to the cyclic structure (in FIG. 18, a center wavelength $\lambda mr$ of the main reflection band) is desirably set not to be present in a wavelength band with a high value of use (a wavelength band W shown in FIG. 18; a wavelength band between a cutoff wavelength $\lambda c$ of the basic mode (TE10) and a cutoff wavelength $\lambda ch$ of the high-order mode (TE20)).

In other words, the inventor derived that, as a method of avoiding influence of the reflection band (the main reflection band) due to the cyclic structure, it is effective means for avoiding influence of the reflection band on a waveguide transmission characteristic to reduce the cyclic length L of the cyclic structure to set the wavelength band (main reflection band) center wavelength $\lambda r$ (the main reflection band center wavelength $\lambda mr$), in which the reflection band is formed, in a region smaller than the cutoff wavelength $\lambda ch$ of the high-order mode.

In this way, in particular, among the reflection bands due to the cyclic structure, the main reflection band has great influence on the transmission characteristic and needs to be avoided in particular. Therefore, it can be said that effectiveness of setting the following expression is high:

$$\lambda mr < \lambda ch \qquad \text{Expression (4)}$$

where $\lambda mr$ represents a center wavelength of the main reflection band and $\lambda ch$ represents a cutoff wavelength of the high-order mode.

"The effectiveness of avoiding influence of the reflection band in the waveguide in which the cyclic unevenness is formed" is examined from another perspective.

As explained above, in the simulation model shown in FIG. 11 and FIG. 12, the cyclic length L can be represented by $$L = s + p \qquad \text{Equation (5)}$$

where "s" ("A" in FIG. 12) represents "a surface on which the inner dielectric 51S and the external conductor 53S are directly connected" in the cyclic unevenness 54S in a waveguide longitudinal direction (a propagating direction) and "p" ("B" in FIG. 12) represents "a gap surface between the inner dielectric 51S and the external conductor 53S".

When a millimeter wave (or a submillimeter wave) is inputted to the waveguide 50S, as explained above, depending on a wavelength of the inputted millimeter wave, multiple reflection occurs in the waveguide because of a structure having cyclicity and, therefore, a transmission characteristic is markedly deteriorated.

More specifically, the multiple reflection occurs and the transmission characteristic is deteriorated when the following equation is satisfied:

$$L/2 = \lambda g/4 \qquad \text{Equation (6)}$$

where $\lambda g$ represents an intra-tube wavelength on an inside of the waveguide 50S as explained above.

The intra-tube wavelength $\lambda g$ has a relation of the following expression, although approximately, between the intra-tube wavelength $\lambda g$ and a wavelength on the outside of the waveguide, that is, the free space $\lambda$.

$$\lambda g \sim \lambda / \sqrt{(\varepsilon r)} \qquad \text{Expression (6A)}$$

where $\varepsilon r$ represents a specific dielectric constant of the inner dielectric 51S.

Therefore, the wavelength $\lambda mr$ of the reflection band (the main reflection band in the above explanation) formed by the cycle L is obtained by substituting Expression (6A) in Equation (6) described above.

$$\lambda mr = 2 \times L \times \sqrt{\varepsilon r} \qquad \text{Equation (6B)}$$

Note that a relation in Expression (6A) described above is generally known as a "wavelength reduction effect". A physical meaning of the "wavelength reduction effect" is equal to the influence of the refractive index indicated by the analogy with the multilayer film interference explained above. Therefore, in addition, a physical meaning of Equation (6B) described above is equal to Equation (1).

On the other hand, as explained above, the transmission characteristic of the waveguide 50S is the best if an inputted millimeter wave can be transmitted in a transmission range of the "basic mode (TE10)" (see FIG. 18). If a propagation mode of the inputted millimeter wave is within a range of a wavelength band W shown in FIG. 18, the inputted millimeter wave is transmitted only in the basic mode (TE10). Therefore, the transmission characteristic is considered to be good.

In other words, when the wavelength $\lambda mr$ of the main reflection band satisfying the condition of Equation (6B) described above satisfies the following expression:

$$\lambda ch < \lambda mr < \lambda c \qquad \text{Expression (7)}$$

since the wavelength $\lambda mr$ of the main reflection band satisfying Equation (6B) described above is present in the wavelength band W in FIG. 18, the transmission characteristic is markedly deteriorated.

In addition, when the wavelength $\lambda mr$ of the reflection band is present in a wavelength band larger than $\lambda c$, that is, when the following expression is satisfied:

$$\lambda mr > \lambda c \qquad \text{Expression (7B)}$$

it is known as a result of examination of the inventor that a characteristic of the wavelength band W in FIG. 18 is easily deteriorated by influence of a reflection band accompanying the main reflection band and the high-order reflection band.

Therefore, the wavelength $\lambda mr$ of the main reflection band satisfying Equation (6B) described above needs to avoid the relations of Expression (7) and Expression (7B). In other words, it can be said that satisfying the following expression has a high effect of improving the characteristic of the wavelength band W in FIG. 18:

$$\lambda mr < \lambda ch \qquad \text{Expression (8)}$$

From the waveguide theory, if a dimension ratio of the long side "a" and the short side "b" of the waveguide is set to 2:1, the wavelength band W in FIG. 18 can be secured wide. When this dimension ratio is satisfied, the cutoff wavelength of the TE20 mode and the cutoff wavelength of the TE10 mode satisfy the following relation.

$$\lambda ch = \lambda c/2 \qquad \text{Equation (9)}$$

Accordingly, from Expression (8) and Equation (9), the following expression only has to hold:

$$\lambda mr < \lambda c/2 \qquad \text{Expression (10)}$$

Accordingly, when $\lambda r$ is erased from Equation (6B) and Expression (10), if the cyclic length L satisfies the following expression:

$$L < \lambda c/(4 \times \sqrt{\varepsilon r}) \qquad \text{Expression (11)}$$

a satisfactory transmission characteristic is obtained even if cyclic unevenness is present in the waveguide.

<Specific Configuration of Flexible Waveguide in First Embodiment>

The inventor found that it is highly effective in the waveguide, in which the cyclic unevenness is formed, to set, based on a verification result in the simulation model of the waveguide in which the cyclic unevenness is formed as explained above, in a region smaller than the cutoff wavelength $\lambda c$ of the high-order mode, a wavelength band (the center wavelength $\lambda r$) in which a "reflection band", which occurs in the waveguide in which the cyclic unevenness is formed, is formed, in particular, set $\lambda mr < \lambda ch$ when the center wavelength of the main reflection band is represented as $\lambda mr$ and the cutoff wavelength of the high-order mode is represented as $\lambda ch$.

An embodiment of a specific flexible waveguide for realizing such a relation between the reflection band and the cutoff wavelength of the high-order mode is explained below.

Figure 19:
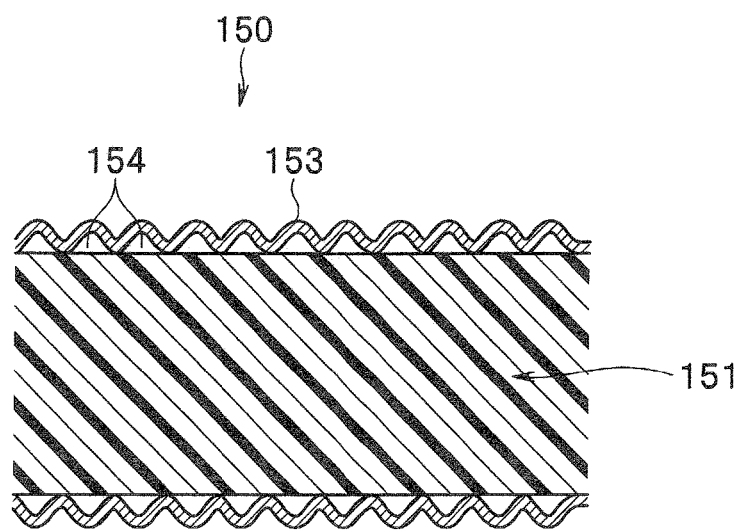
FIG. 19 is a main part sectional view showing the external conductor assuming a bellows shape and the inner dielectric in the flexible waveguide in the first embodiment of the present invention.

FIG. 19 is a main part sectional view showing an external conductor assuming a bellows shape and an inner dielectric in the flexible waveguide in the first embodiment of the present invention.

In the first embodiment, the flexible waveguide 150 includes, as shown in FIG. 3 to FIG. 6 described above, the linear inner dielectric 151, the dielectric constant of which is uniform in the longitudinal direction and the cross section of which assumes the same shape in the longitudinal direction, and the external conductor 153 disposed in the position covering the outer periphery of the inner dielectric 151.

In the first embodiment, the external conductor 153 is a tube disposed in a position covering the outer periphery of the inner dielectric 151 and, as shows in a sectional view of FIG. 19, is configured by a tubular member assuming a so-called bellows shape forming a cyclic shape displacement section, that is, cyclic unevenness 154 in the longitudinal direction.

The external conductor 153 includes a predetermined metal layer section. Electric conductivity of the metal layer section is set to $59 \times 10^6$ S/m equivalent to the electric conductivity of pure copper. Note that although the electric conductivity is uniquely determined here, in the present invention, the electric conductivity of the metal layer section is not limited to this. In the embodiment, it is desirable to use a metal layer having high electric conductivity.

Note that the external conductor 153 having the bellows shape in this embodiment is configured to include a metal layer arranged on a side in contact with the inner dielectric 151 and a ground layer on an outer side. However, in the following explanation, explanation about the ground layer is omitted.

<Simulation Model in First Embodiment>

A transmission loss of the flexible waveguide 150 according to the first embodiment including the external conductor 153 having the bellows shape explained above is explained using a simulation model.

Figure 20:
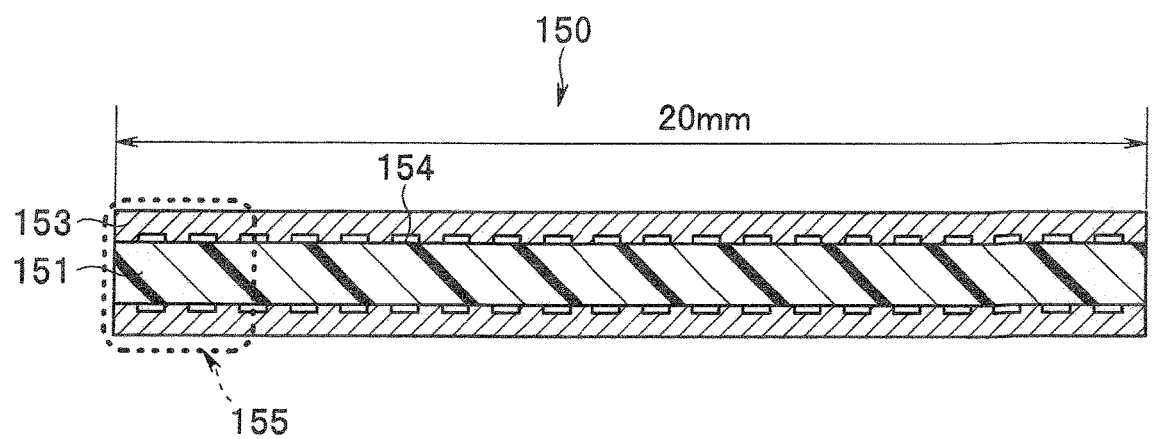
FIG. 20 is a main part sectional view showing a longitudinal cross section in the longitudinal direction of the simulation model relating to the flexible waveguide in the first embodiment.
Figure 21:
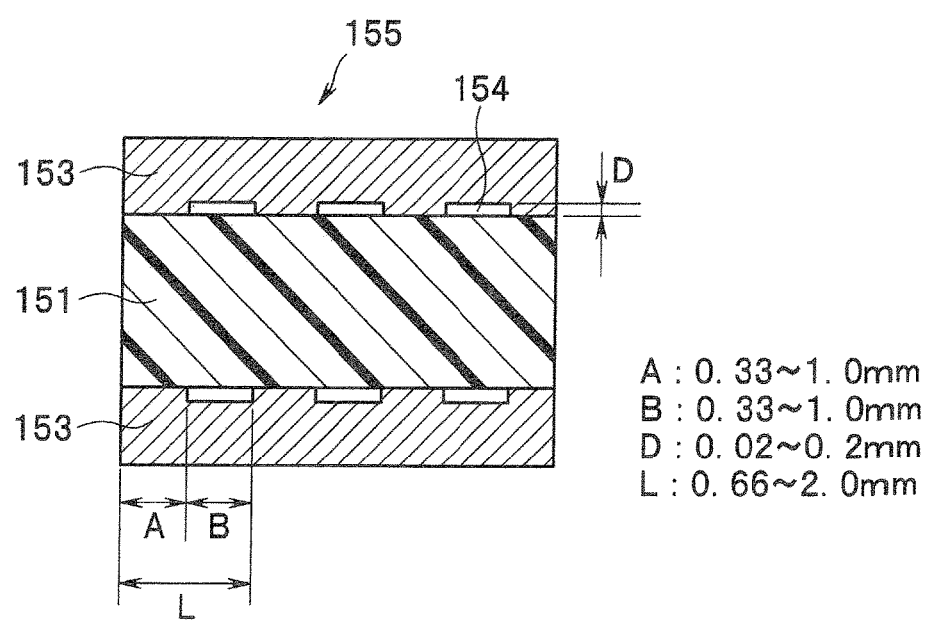
FIG. 21 is a main part enlarged sectional view enlarging and showing a position of the longitudinal cross section in the longitudinal direction of the simulation model relating to the flexible waveguide in the first embodiment and is a diagram showing a cyclic length L of the cyclic unevenness.

FIG. 20 is a main part sectional view showing a longitudinal cross section in the longitudinal direction of the simulation model relating to the flexible waveguide in the first embodiment. FIG. 21 is a main part enlarged sectional view enlarging and showing a position of the longitudinal cross section in the longitudinal direction of the simulation model relating to the flexible waveguide in the first embodiment and is a diagram showing the cyclic length L of the cyclic unevenness.

Figure 22:
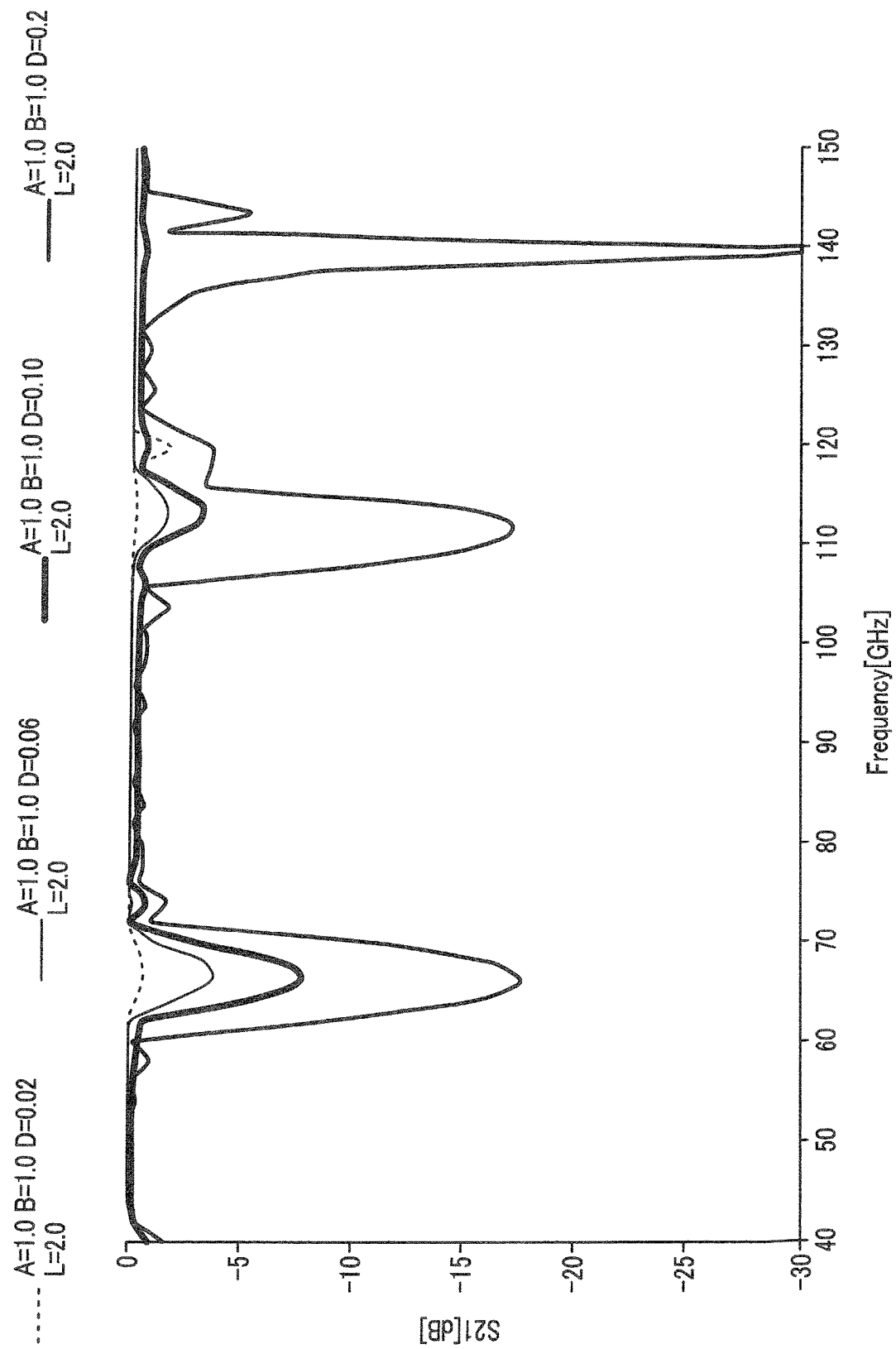
FIG. 22 is a diagram showing a transmission characteristic in a case of the cyclic length L=2.0 of the cyclic unevenness in the simulation model relating to the flexible waveguide in the first embodiment.
Figure 23:
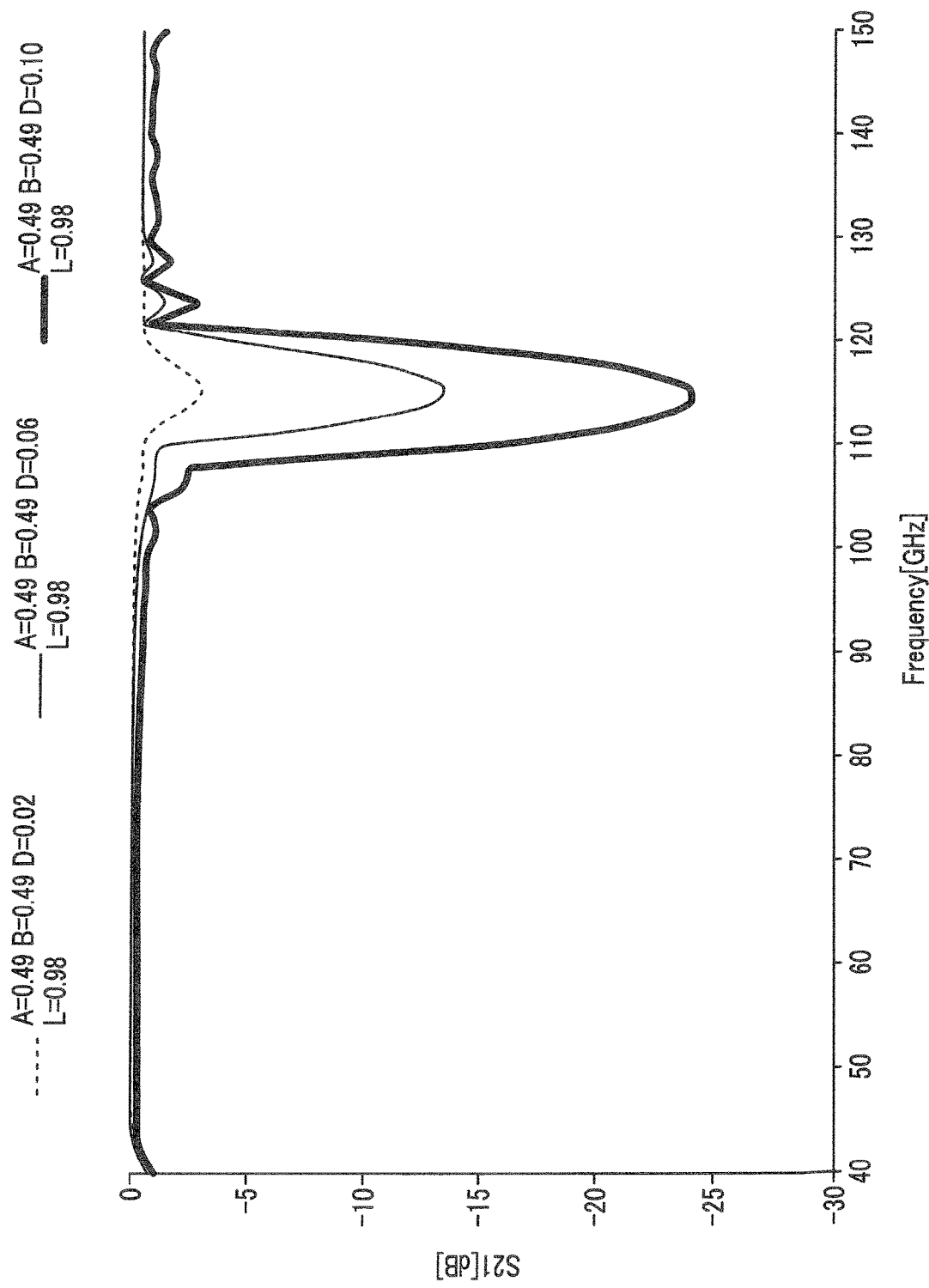
FIG. 23 is a diagram showing a transmission characteristic in a case of the cyclic length L=0.98 of the cyclic unevenness in the simulation model relating to the flexible waveguide in the first embodiment.
Figure 24:
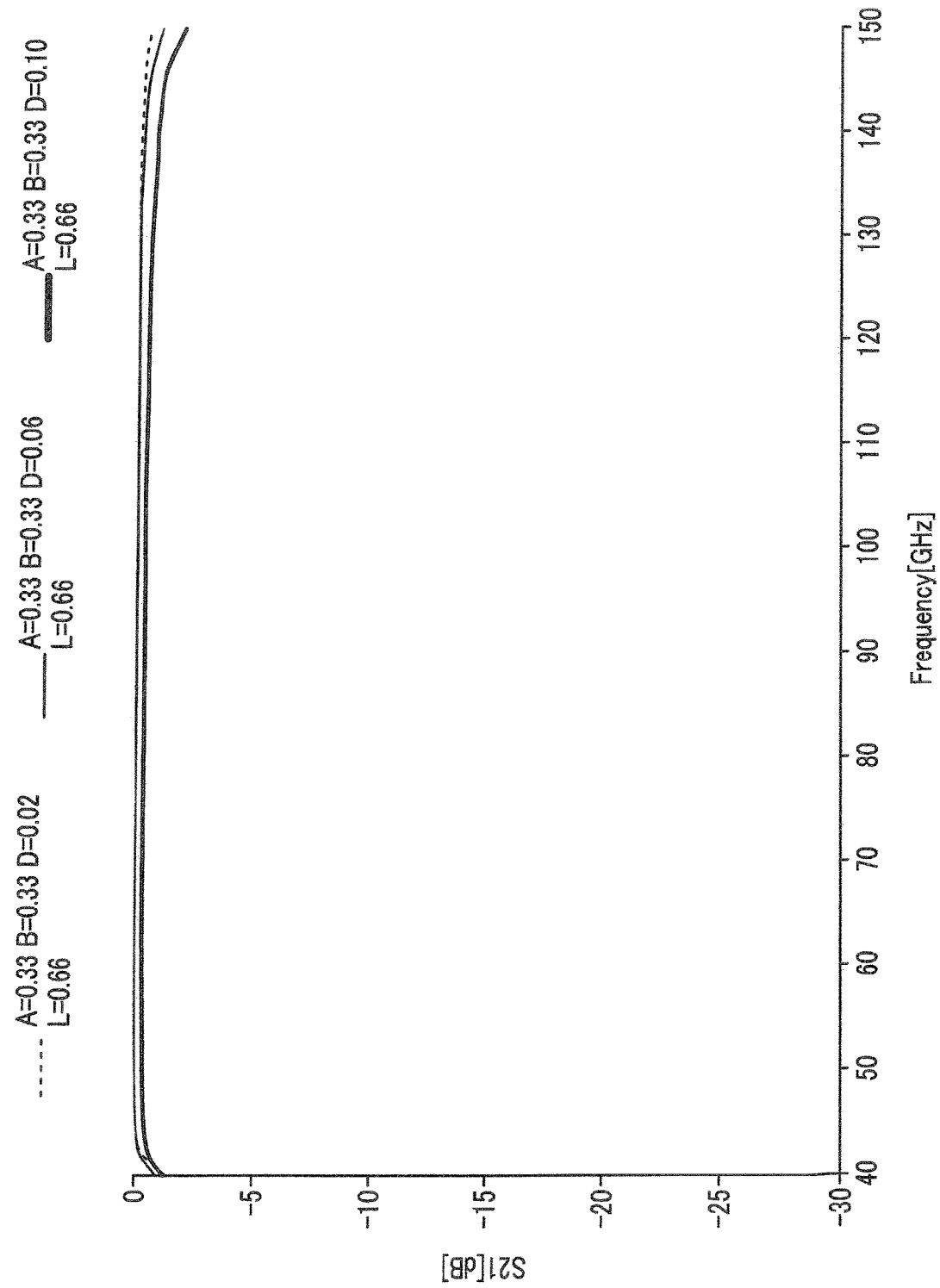
FIG. 24 is a diagram showing a transmission characteristic in a case of the cyclic length L=0.66 of the cyclic unevenness in the simulation model relating to the flexible waveguide in the first embodiment.

FIG. 22 is a diagram showing a transmission characteristic in a case of the cyclic length L=2.0 of the cyclic unevenness in the simulation model relating to the flexible waveguide in the first embodiment. FIG. 23 is a diagram showing a transmission characteristic in a case of the cyclic length L=0.98 of the cyclic unevenness in the simulation model relating to the flexible waveguide in the first embodiment. FIG. 24 is a diagram showing a transmission characteristic in a case of the cyclic length L=0.66 of the cyclic unevenness in the simulation model relating to the flexible waveguide in the first embodiment.

In calculating a transmission loss relating to the flexible waveguide 150 in the first embodiment, a simulation model of a square waveguide having length of 20 mm is assumed as shown in FIG. 20 and FIG. 21. Note that FIG. 21 is a diagram enlarging and showing a part (indicated by a reference numeral 155) in FIG. 20.

This simulation model (the simulation model according to the first embodiment is hereinafter referred to as a first simulation model) is the square waveguide having the length of 20 mm as explained above. A predetermined dielectric is disposed on an inside of the simulation model.

A material of the inner dielectric in the first simulation model is PFA (perfluoroalkoxy alkane). The inner dielectric has a specific dielectric constant $\varepsilon_r=2.0$ and dielectric loss tangent (tan $\delta$)=0.0003 and has a square cross section, respective sides of which in a rectangular shape of the cross section are a long side a=2.66 mm and a short side b=1.33 mm Note that, assuming transmission of a 60 GHz millimeter wave, dimensions of the sectional shape are set such that a satisfactory transmission characteristic is obtained at 50 to 75 GHz (this frequency band is hereinafter referred to as a V band).

A simulator used in the simulation is HFSS manufactured by ANSYS, Inc. An analysis error ($\Delta S$) is set to 0.01.

On the other hand, in the first simulation model, the external conductor 153 is disposed to cover an outer side of the inner dielectric 151. The cyclic unevenness 154 is formed on an inner peripheral surface of the external conductor 153 in the longitudinal direction. Air is filled in gaps (recesses) in the cyclic unevenness 154. Electric conductivity of the cyclic unevenness 154 is set to $59 \times 10^6$ S/m equivalent to the electric conductivity of pure copper.

Note that, in the cyclic unevenness 154, as shown in FIG. 21, a projection (a portion in contact with the inner dielectric 151) is represented as "A (or s)", a recess (a portion forming a gap between the portion and the inner dielectric 151) is represented as "B (or p)", and a minimum cyclic length L is set to L=A+B (or L=s+p) in the waveguide longitudinal direction (the propagating direction).

In the simulation model set in this way, the simulation is carried out in three patterns in which the cyclic length L is respectively, L=0.66 mm, L=0.98 mm, and L=2.0 mm A millimeter wave (or a submillimeter wave) is inputted to the respective patterns.

FIG. 22 is a diagram showing a transmission characteristic in the case of the cyclic length L=2.0 of the cyclic unevenness in the simulation model relating to the flexible waveguide in the first embodiment. FIG. 23 is a diagram showing a transmission characteristic in the case of the cyclic length L=0.98 of the cyclic unevenness in the simulation model relating to the flexible waveguide in the first embodiment. FIG. 24 is a diagram showing a transmission characteristic in the case of the cyclic length L=0.66 of the cyclic unevenness in the simulation model relating to the flexible waveguide in the first embodiment.

In all the figures, a horizontal axis represents a frequency. From a relation of light speed=wavelength×frequency, the wavelength and the frequency have a relation in which the frequency decreases when the wavelength increases and the frequency increases when the wavelength decreases. A vertical axis represents a transmission characteristic in a dB unit. The vertical axis indicates that the transmission characteristic is better as a numerical value is closer to 0.

As explained above, when the cyclic length L satisfies the following Expression (11):

$$L<\lambda c/(4\times\sqrt{\varepsilon r}) \quad \text{Expression (11)}$$

a satisfactory transmission characteristic is obtained even if cyclic unevenness is present in the waveguide.

From the waveguide dimensions and the specific dielectric constant of the inner dielectric, the cutoff wavelength $\lambda c$ in the basic mode of the simulation model is calculated as follows:

$$\lambda c = 7.518 \text{ mm}$$

This is represented as fc=39.9 GHz in a frequency unit.

Since the cutoff wavelength $\lambda ch$ in the high-order mode has a relation of $\lambda ch = \lambda c/2$, the cutoff wavelength $\lambda ch$ is calculated as follows:

$$\lambda ch = 3.758 \text{ mm}$$

This is represented as fc=79.8 GHz in a frequency unit.

Accordingly, a frequency band transmitted only in the basic mode is 39.9 GHz to 79.8 GHz. This covers the V band, which is a target frequency band.

When a value of the cutoff wavelength is substituted in Expression (11), the following is obtained:

$$L<1.329 \text{ mm} \quad \text{Expression (12)}$$

If this is satisfied, a main reflection band is absent in the frequency band transmitted only in the basic mode (TE10), that is, a stable transmission characteristic is obtained.

In simulation results shown in FIG. 22 to FIG. 24, when the cyclic length L is L=2.0 mm, as shown in FIG. 22, deterioration in the transmission characteristic due to the main reflection band is observed near 66 GHz (incidentally, deterioration in the transmission characteristic due to the high-order reflection band is observed near 110 to 114 GHz).

In this way, when the cyclic length L is L=2.0 mm, it turns out that the main reflection band is present in the frequency band transmitted only in the basic mode and the transmission characteristic is markedly deteriorated in the frequency band transmitted only in the basic mode.

On the other hand, when the cyclic length L is L=0.98 mm, as shown in FIG. 23, deterioration in the transmission characteristic due to the main reflection band is observed near 114 GHz. The deterioration of the transmission characteristic is sufficiently larger than a maximum (79.8 GHz) of the frequency band transmitted only in the basic mode. Since Expression (12) is satisfied, it turns out that stable transmission characteristic is obtained in the frequency band transmitted only in the basic mode.

Further, when the cyclic length L is L=0.66 mm, as shown in FIG. 24, deterioration in the transmission characteristic due to the main reflection band is not observed. This indicates that a simulation range is 40 to 150 GHz and the main reflection band does not appear in this range. Note that the main reflection band is considered to be present at a frequency higher than 150 GHz.

In the case of L=0.66 mm, since Expression (12) described above is satisfied, it turns out that a stable transmission characteristic is obtained in the frequency band transmitted only in the basic mode.

As explained above, with the flexible waveguide in the first embodiment, even in the waveguide in which the cyclic unevenness assuming the bellows shape is formed in the external conductor 153, by appropriately setting a cyclic length of the cyclic unevenness, it is possible to avoid presence of a main reflection band in a wavelength band transmitted only in a desired basic mode. It is possible to provide the waveguide that achieves both of appropriate flexibility and an excellent transmission characteristic in the waveguide that transmits a radio wave having a frequency equal to or higher than a frequency of a desired millimeter wave (including a submillimeter wave).

<Flexible Waveguide in Second Embodiment>

A second embodiment of the present invention is explained.

A configuration of an endoscope system according to the second embodiment is basically the same as the configuration in the first embodiment. Therefore, only differences from the first embodiment are explained. Explanation of the other details is omitted.

In other words, the endoscope system according to the second embodiment is the same as the endoscope system according to the first embodiment in an inner dielectric in a flexible waveguide but is different from the endoscope system according to the first embodiment in a configuration of an external conductor in the flexible waveguide. A configuration of the endoscope system is basically the same as the configuration in the first embodiment.

Figure 25:
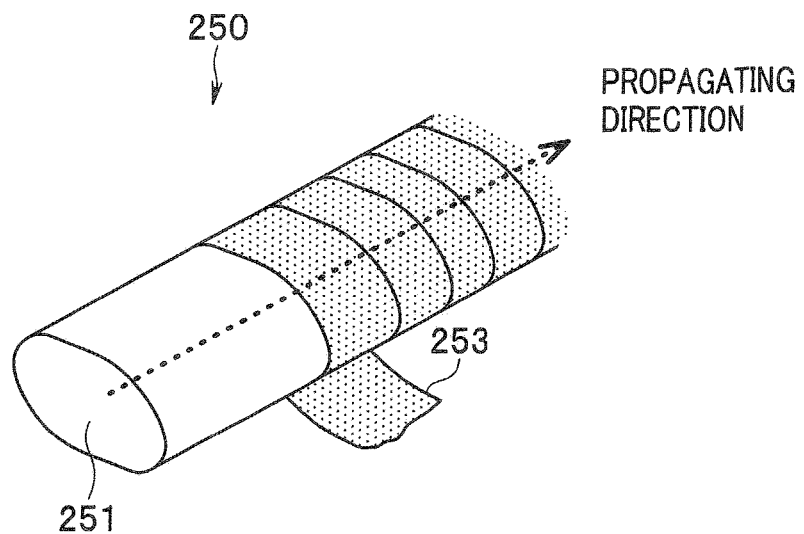
FIG. 25 is a main part sectional view showing an external conductor assuming a spiral shape and an inner dielectric in a flexible waveguide in a second embodiment of the present invention.
Figure 26:
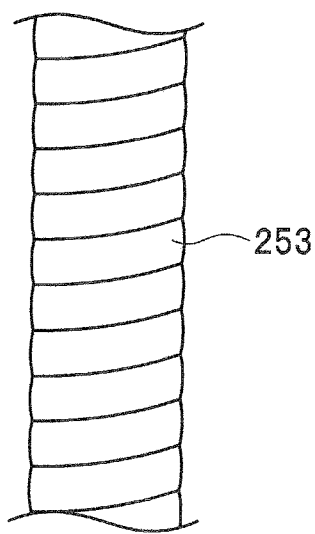
FIG. 26 is an exterior view showing an exterior of the external conductor assuming the spiral shape in the flexible waveguide in the second embodiment.

As the flexible waveguide according to the second embodiment, realistically, a flexible waveguide in which an external conductor assuming a shape considering flexibility is arranged shown in FIG. 25, FIG. 26, or the like is assumed.

Concerning the flexible waveguide according to the second embodiment, in order to more accurately grasp electromagnetic physical properties such as a transmission loss relating to the realistic flexible waveguide or mechanical physical properties such as flexibility, considering that a radio wave of a millimeter wave (including a submillimeter wave) is propagated, an approximate model is set concerning a material, a shape, and the like in the realistic flexible waveguide and set as the flexible waveguide according to the second embodiment.

The flexible waveguide according to the second embodiment is explained below. In addition, characteristics such as a material, a shape, and a transmission loss of the flexible waveguide conform to the characteristics of the assumed realistic flexible waveguide.

Figure 27:
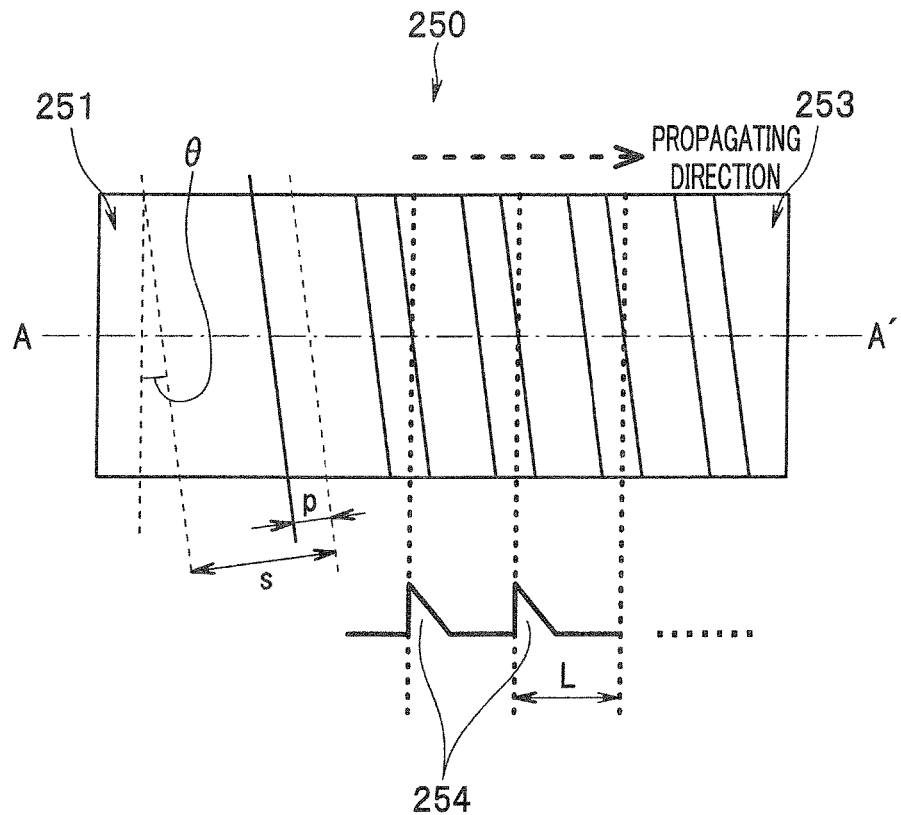
FIG. 27 is an explanatory diagram showing a positional relation between the external conductor assuming the spiral shape and the inner dielectric, and the cyclic unevenness in the flexible waveguide in the second embodiment.
Figure 28:
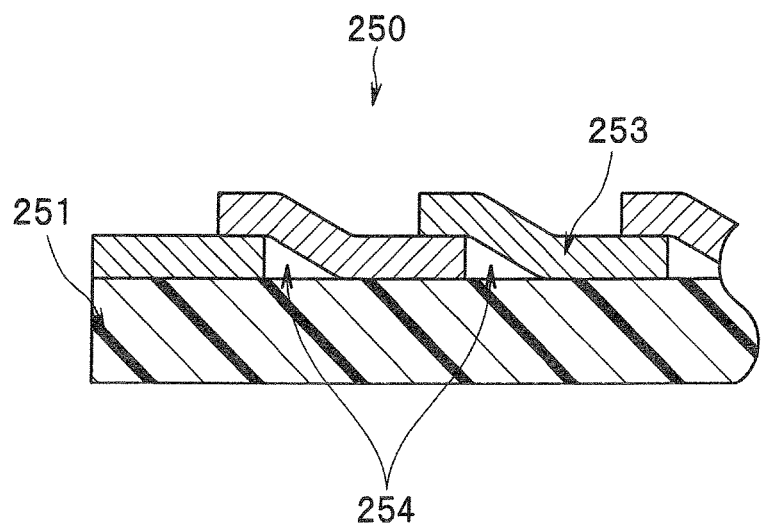
FIG. 28 is a main part sectional view showing the positional relation between the external conductor assuming the spiral shape and the inner dielectric, and the cyclic unevenness in the flexible waveguide in the second embodiment and showing a cross section A-A' of FIG. 27.

FIG. 25 is a main part sectional view showing an external conductor assuming a spiral shape and an inner dielectric in the flexible waveguide in the second embodiment of the present invention. FIG. 26 is an exterior view showing an exterior of the external conductor assuming the spiral shape in the flexible waveguide in the second embodiment. FIG. 27 is an explanatory diagram showing a positional relation between the external conductor assuming the spiral shape and the inner dielectric, and the cyclic unevenness in the flexible waveguide in the second embodiment. FIG. 28 is a main part sectional view showing the positional relation between the external conductor assuming the spiral shape and the inner dielectric, and the cyclic unevenness in the flexible waveguide in the second embodiment and showing a cross section A-A' of FIG. 27.

In the second embodiment, as in the first embodiment, a distal end portion of a flexible waveguide 250 according to the second embodiment that allows a millimeter wave or a submillimeter wave to pass is connected to the proximal end side of the driver IC 23 across the transmission and reception antenna 27 integrated with the package of the driver IC 23.

As in the first embodiment, the flexible waveguide 250 has flexibility. After a distal end side of the flexible waveguide 250 is connected to the driver IC 23 disposed at the distal end rigid portion 10, the flexible waveguide 250 is extended toward the proximal end side of the insertion section 6.

Further, as in the first embodiment, after being inserted through an inside of the insertion section 6 including the bending section 9 and the flexible tube section further on the proximal end side such as the further proximal end side relative to the driver IC 23 in the insertion section 6, that is, a further proximal end side portion relative to a disposition part of the driver IC 23 at the distal end rigid portion 10, the flexible waveguide 250 is inserted through the inside of the operation section 7 and the inside of the universal cord 8 and disposed in a position leading to the video processor 3.

As in the first embodiment, the flexible waveguide 250 according to the second embodiment is a signal transmission line connecting the image pickup unit 20 and the image processing section (the image processing circuit 31) in the video processor 3. At least a part of the flexible waveguide 250 is a waveguide for propagating a millimeter wave or a submillimeter wave.

<Inner Dielectric and External Conductor in Flexible Waveguide>

As shown in FIG. 25, in the second embodiment as well, the flexible waveguide 250 includes a linear inner dielectric 251 on an inside, a dielectric constant of which is uniform in the longitudinal direction and a cross section of which assumes the same shape in the longitudinal direction, and an external conductor 253 disposed in a position covering an outer periphery of the inner dielectric 251.

Note that, in the second embodiment as well, "a dielectric constant is uniform" means that the dielectric constant is uniform in terms of a dimension in a wavelength order of a radio wave (a millimeter wave or a submillimeter wave) propagating inside the waveguide.

In other words, a dielectric constant distribution by a structure having a dimension different from the wavelength order by one to two or more digits does not affect the radio wave propagating inside the waveguide. Therefore, in the second embodiment as well, this is included in the representation "a dielectric constant is uniform".

<Specific Dielectric Constant and Shape of Inner Dielectric in Second Embodiment>

A specific dielectric constant of the inner dielectric 251 is set to a specific dielectric constant $\varepsilon_{r1}=4.5$. On the other hand, the inner dielectric 251 assumes a substantially elliptical shape, which is a sectional shape, a ratio of a long diameter and a short diameter of which is constant in the longitudinal direction. The long diameter and the short diameter are respectively set to a long diameter $a=1.77$ mm and a short diameter $b=0.89$ mm.

<Shape of External Conductor in Second Embodiment>

On the other hand, the external conductor 253 in the second embodiment is configured by, for example, a tape including one belt-like section (belt-like member) including a metal layer (a metal substance), a cross section of the tape perpendicular to an extending axis assuming a rectangular cross section.

The tape, which is the belt-like section, extends such that a flat section of the tape is wound in a spiral shape on an outer peripheral surface of the inner dielectric 251 in a state in which a side edge portion of the tape forms a predetermined angle with respect to the longitudinal axis of the flexible waveguide 250. The tape is disposed such that, when the tape is wound in the spiral shape, side edge portions facing each other in adjacent winds of the tape keep a constant interval in the longitudinal direction of the waveguide 250, more specifically, to be wrapped in an overlapping manner (see FIG. 25 and FIG. 26).

Note that the external conductor 253 includes a predetermined metal layer section. Electric conductivity of the metal layer section is set to $59\times10^6$ S/m equivalent to the electric conductivity of pure copper. Note that although the electric conductivity is uniquely determined here, in the present invention, the electric conductivity of the metal layer section is not limited to this. In the embodiment, it is desirable to use a metal layer having high electric conductivity.

Note that the tape, which is the external conductor 253 in this embodiment, is configured to include the metal layer arranged on the side in contact with the inner dielectric 251 and the ground layer on the outer side. However, explanation of the ground layer is omitted.

In this embodiment, as explained above, the tape, which is the external conductor 253, is wound in the spiral shape on the outer periphery of the inner dielectric 251. At this time, the adjacent winds of the tape are wrapped and wound to keep a constant interval in the longitudinal direction of the waveguide 250. Therefore, as shown in FIG. 27 and FIG. 28, gaps (cyclic unevenness indicated by a reference numeral 254) are formed between the inner dielectric 251 and the metal layer of the external conductor 253.

The gaps 254 are formed with cyclicity in the propagating direction (the longitudinal direction). In other words, the cyclic unevenness (a cyclic structure) 254 is formed in the longitudinal direction.

In the cyclic unevenness 254, which is this cyclic structure in this embodiment, the cyclic length L is calculated as follows:

$$L=(s+(-p))/\cos\theta=(s-p)/\cos\theta \qquad \text{Equation (13)}$$

where s represents a width of the tape, p represents the constant interval (a wrapped portion in this embodiment), and θ represents a predetermined angle with respect to the waveguide longitudinal axis at the time when an angle orthogonal to the longitudinal axis of the waveguide 250 is set to 0 degrees (see FIG. 27).

Further, the cyclic unevenness 254 is a structure satisfying the following expression:

$$(s+(-p))/\cos\theta<\lambda c/(4\times\sqrt{\varepsilon r}) \qquad \text{Expression (14)}$$

where λc represents a cutoff wavelength in the basic mode of the waveguide 250 and a represents a specific dielectric constant of the inner dielectric 251.

Note that, since the adjacent winds of the tape are wrapped in this embodiment as explained above, the "constant interval" is a dimension in a minus direction in the propagating direction.

In the second embodiment, it is possible to verify, using the same simulation model as the simulation model adopted in the first embodiment, a transmission loss of the simulation model.

In other words, in the flexible waveguide 250 in the second embodiment as well, when the cyclic length L satisfies the following expression:

$$L<\lambda c/(4\times\varepsilon r) \qquad \text{Expression (11)}$$

a satisfactory transmission characteristic is obtained even if cyclic unevenness (the cyclic unevenness 254 explained above) is present in the waveguide.

In the second embodiment as well, if the tape having the width s is wound on the inner dielectric 251 at the constant interval p such that the cyclic length L satisfies the following expression:

$$L<0.886 \text{ mm} \qquad \text{Expression (12A)}$$

a main reflection band is absent in the frequency band transmitted only in the basic mode (TE10), that is, a stable transmission characteristic is obtained.

As explained above, in the flexible waveguide in the second embodiment as well, even in the waveguide in which the cyclic unevenness 254 is formed by the belt-like tape, such as the external conductor 253, wound in the spiral shape on the inner dielectric 251, by appropriately setting a cyclic length of the cyclic unevenness, it is possible to avoid presence of a main reflection band in a wavelength band transmitted only in a desired basic mode. It is possible to provide the waveguide that achieves both of appropriate flexibility and an excellent transmission characteristic in the waveguide that transmits a radio wave having a frequency equal to or higher than a frequency of a desired millimeter wave (including a submillimeter wave).

<First Modification According to Second Embodiment>

A first modification according to the second embodiment is explained.

Figure 29:
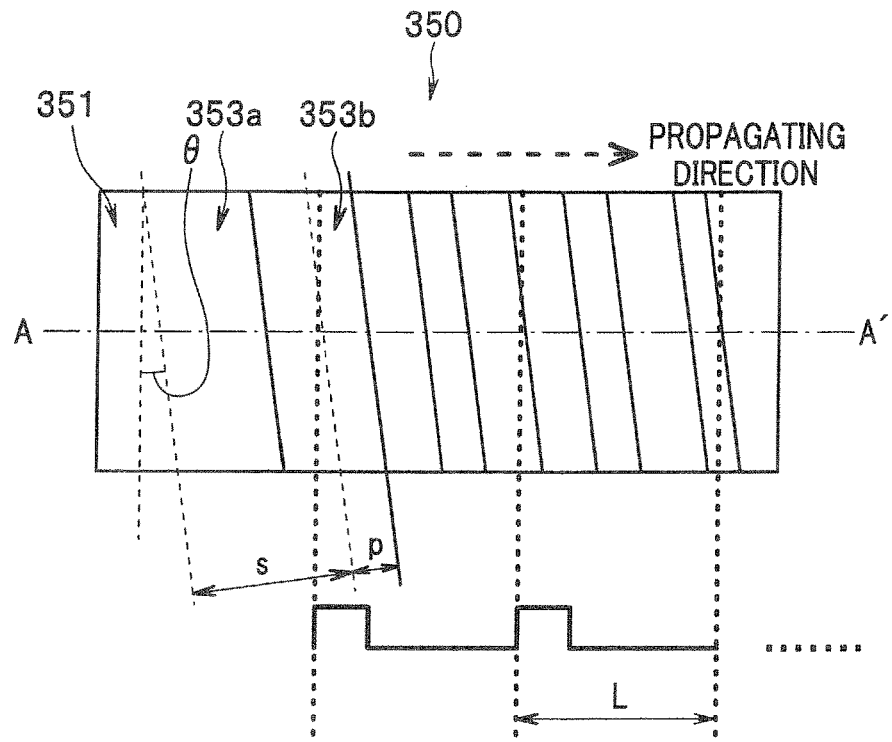
FIG. 29 is an explanatory diagram showing a positional relation between an external conductor assuming a spiral shape and an inner dielectric, and cyclic unevenness in a first modification of the flexible waveguide in the second embodiment.
Figure 30:
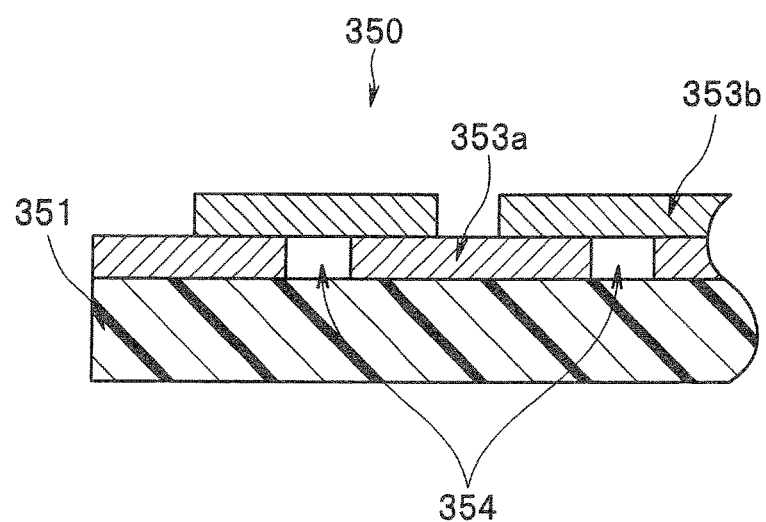
FIG. 30 is a main part sectional view showing the positional relation between the external conductor assuming the spiral shape and the inner dielectric, and the cyclic unevenness in the first modification of the flexible waveguide in the second embodiment and showing a cross section A-A' of FIG. 29.

FIG. 29 is an explanatory diagram showing a positional relation between an external conductor assuming a spiral shape and an inner dielectric, and cyclic unevenness in the first modification of the flexible waveguide in the second embodiment. FIG. 30 is a main part sectional view showing the positional relation between the external conductor assuming the spiral shape and the inner dielectric, and the cyclic unevenness in the first modification of the flexible waveguide in the second embodiment and showing a cross section A-A' of FIG. 29.

As explained above, in the flexible waveguide 250 in the second embodiment, one belt-like section (tape) is wound on the outer periphery of the inner dielectric 251. However, a flexible waveguide 350 in this modification is configured by winding a plurality of belt-like tapes (external conductors 353a and 353b), which are external conductors, on an outer periphery of an inner dielectric 351. Since the other components are the same as the components in the second embodiment, detailed explanation of the components is omitted.

As shown in FIG. 29 and FIG. 30, in the first modification of the second embodiment as well, the inner dielectric 351 in the flexible waveguide 350 is a linear dielectric, a dielectric constant of which is uniform in the longitudinal direction and a cross section of which assumes the same shape in the longitudinal direction.

On the other hand, external conductors 353a and 353b in the first modification according to the second embodiment are configured by, for example, tapes (hereinafter referred to as tapes 353a and 353b as well) including a plurality of belt-like sections including a metal layer (a metal substance), a cross section of which perpendicular to the extending axis assumes a rectangular cross section. In FIG. 29 and FIG. 30, two tapes are shown.

In this modification as well, both the tapes 353a and 353b, which are the belt-like sections, extend such that flat sections of the tapes are alternately wound in a spiral shape on an outer peripheral surface of the inner dielectric 351 in a state in which side edge portions of the tapes form a predetermined angle with respect to the longitudinal axis of the flexible waveguide 350

The tape 353a and the tape 353b adjacent to each other are disposed such that, when being wound in the spiral shape, the side edge portions facing each other keep a constant interval in the longitudinal direction of the waveguide 350 (see FIG. 29 and FIG. 30).

In this modification, the tapes 353a and 353b, which are the external conductors, disposed to keep the constant interval are alternately wound in the spiral shape on the outer periphery of the inner dielectric 351 as explained above. At this time, the tape 353a is wound to be directly in contact with the inner dielectric 351 and the tape 353b is wound to be suspended on an upper surface between adjacent winds of the tape 353a.

Consequently, as shown in FIG. 30, cyclic gaps (cyclic unevenness indicated by a reference numeral 354) are formed in spaces covered by adjacent winds of the tape 353a disposed on the outer peripheral surface of the inner dielectric 351 and bottom surfaces of adjacent winds of the tape 353b.

The gaps 354 are formed with cyclicity in the propagating direction (the longitudinal direction), that is, forms the cyclic unevenness (a cyclic structure) 354 in the longitudinal direction.

In this modification, in the cyclic unevenness 354, which is this cyclic structure, the cyclic length L is calculated as follows:

$$L = (s+p)/\cos\theta$$

where s represents widths of the tapes, p represents the constant interval, and $\theta$ represents a predetermined angle in the waveguide longitudinal direction at the time when an angle orthogonal to the longitudinal axis of the waveguide 350 is set to 0 degrees (see FIG. 29).

Further, the cyclic unevenness 354 is a structure satisfying the following expression:

$$(s+p)/\cos\theta < \lambda c/(4 \times \sqrt{\varepsilon r})$$

where $\lambda c$ represents a cutoff wavelength in the basic mode of the waveguide 350 and a represents a specific dielectric constant of the inner dielectric 351.

In the first modification according to the second embodiment, it is possible to verify, using the same simulation model as the simulation model adopted in the first embodiment, a transmission loss of the simulation model.

In other words, in the flexible waveguide 350 in this modification as well, when the cyclic length L satisfies the following expression:

$$L < \lambda c/(4 \times \varepsilon r) \qquad \text{Expression (11)}$$

a satisfactory transmission characteristic is obtained even if cyclic unevenness (the cyclic unevenness 354 explained above) is present in the waveguide.

In this modification as well, if the cyclic length L satisfies the following expression:

$$L < 0.886 \text{ mm} \qquad \text{Expression (12B)}$$

a main reflection band is absent in the frequency band transmitted only in the basic mode (TE10), that is, a stable transmission characteristic is obtained.

As explained above, in the flexible waveguide in the modification according to the second embodiment as well, even in the waveguide in which the cyclic unevenness 354 is formed by the plurality of belt-like tapes 353a and 353b wound in the spiral shape on the inner dielectric 351, by appropriately setting a cyclic length of the cyclic unevenness, it is possible to avoid presence of a main reflection band in a wavelength band transmitted only in a desired basic mode. It is possible to provide the waveguide that achieves both of appropriate flexibility and an excellent transmission characteristic in the waveguide that transmits a radio wave having a frequency equal to or higher than a frequency of a desired millimeter wave (including a submillimeter wave).

<Second Modification According to Second Embodiment>

A second modification according to the second embodiment is explained.

Figure 31:
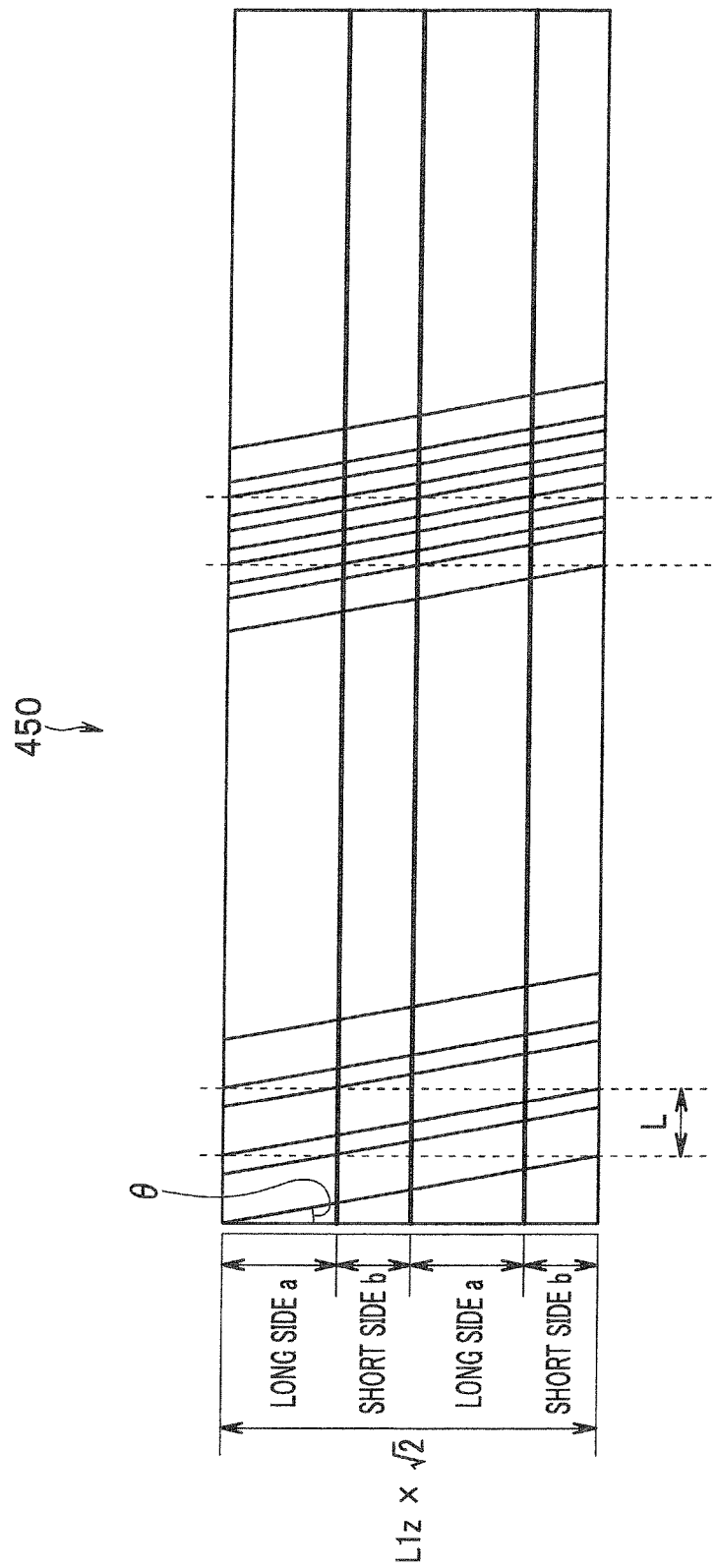
FIG. 31 is a development view in which an external conductor assuming a spiral shape in a second modification of the flexible waveguide in the second embodiment is exploded in an entire peripheral direction of the waveguide.

FIG. 31 is a development view in which an external conductor assuming a spiral shape in the second modification of the flexible waveguide in the second embodiment is exploded in an entire peripheral direction of the waveguide Note that when the plurality of belt-like external conductors 353a and 353b are wound on the inner dielectric 351 as in the first modification according to the second embodiment, a relation explained below holds. A flexible waveguide 450 in the second modification according to the second embodiment is explained below.

As shown in FIG. 31, when a plurality of external conductors (for example, the tapes explained above) are wound in a spiral shape on the inner dielectric, there is a relation indicated by the following equations:

$$L1z=2\times(a+b) \text{ and}$$

$$(L/L1z)=\tan \theta \quad \text{Equation (15)}$$

where θ represents a winding angle of the "tape" with respect to the waveguide longitudinal axis, L1z represents an entire periphery of the waveguide, "a" represents a waveguide long side, and "b" represents a waveguide short side.

Equation (15) is modified as follows:

$$L=L1z\times\tan \theta \quad \text{Equation (16)}$$

From this relation, if the winding angle θ of the external conductors, that is, the tapes is set small, the cyclic length L of the cyclic unevenness formed in the external conductor decreases.

As explained above, the entire periphery L1z is calculated as follows:

$$L1z=2\times(a+b) \quad \text{Equation (17)}$$

From the waveguide theory, in the second embodiment as well, a wavelength band can be secured wide if a ratio of the waveguide long side "a" and the waveguide short side "b" is set to 2:1 as in the first embodiment as follows:

$$b=a/2 \quad \text{Equation (18)}$$

According to Equations (17) and (18), $$L1z=2\times(a+a/2), L1z=3\times a \quad \text{Equation (19)}$$

When L1z is erased from Equations (15) and (19), the following equation is obtained:

$$L=3\times a\times\tan \theta \quad \text{Equation (20)}$$

The cutoff wavelength λc can be represented as follows using the waveguide long side "a":

$$\lambda c=2\times a\times\sqrt{\varepsilon r} \quad \text{Equation (21)}$$

Accordingly, from Expression (11) and Equations (20) and (21), $$3\times a\times\tan \theta<(2\times a\times\sqrt{\varepsilon r})/(4\times\sqrt{\varepsilon r})$$

When "a" is erased, the following expression is obtained:

$$\tan \theta<1/6 \quad \text{Expression (22)}$$

θ is calculated from Expression (22) as follows:

$$\theta<9.46[°]$$

In other word, if the winding angle θ is smaller than 9.46°, a main reflection band is absent in the frequency band transmitted only in the basic mode (TE10), that is, a stable transmission characteristic is obtained.

<Flexible Waveguide in Third Embodiment>

A third embodiment of the present invention is explained.

A configuration of an endoscope system according to the third embodiment is basically the same as the configuration in the first embodiment. Therefore, only differences from the first embodiment are explained. Explanation of the other details is omitted.

In other words, the endoscope system according to the third embodiment is the same as the endoscope system according to the first embodiment in an inner dielectric in a flexible waveguide but is different from the endoscope system according to the first embodiment in a configuration of an external conductor in the flexible waveguide. A configuration of the endoscope system is basically the same as the configuration in the first embodiment.

<Low-Order Reflection Band>

Prior to the explanation of the third embodiment, the low-order reflection band described above is explained.

In the explanation of the multiple reflection concerning the "multilayer reflection film" shown in FIG. 10 described above, the dielectric films having the different refractive indexes overlap at the two-layer period.

In this case, a "reflection band" does not occur in a band having a wavelength longer than a main reflection band. This is an event well-known in the multilayer reflection film. However, it is known that, if disturbance in a longer period than two layers is added to this, occurrence of the reflection band is more complicated and, in addition to the reflection wavelength (λ/4), reflection can occur on a wavelength long side as well. Such a point is clearly described in Japanese Patent Application Laid-Open Publication No. 2011-242437.

In other words, in the multilayer reflection film, when a certain kind of disturbance (disturbance in a longer period than the two layers) is added to the two-layer period, a reflection band can be formed in a wavelength band longer than the main reflection band.

Therefore, the inventor inferred that, in a cyclic structure relating to the flexible waveguide of the present invention as well, reflection could occur in the wavelength band (the low-order reflection band) longer than the "main reflection band" when a certain kind of disturbance (disturbance in a longer period than the two layers) with respect to the two-layer period.

In particular, in the external conductor in this embodiment, since it is assumed that the multilayer reflection film sometimes does not have a clear structure for clearly dividing layers, it can be estimated that disturbance in a long period is easily obtained.

In other words, considering a case in which the "low-order reflection band" is easily formed in a band having a wavelength longer than the "main reflection band", the inventor further developed the present invention concerning a case in which influence by these reflection bands easily occurs as in this embodiment.

This is explained more in detail with reference to FIG. 32 to FIG. 36.

Figure 32:
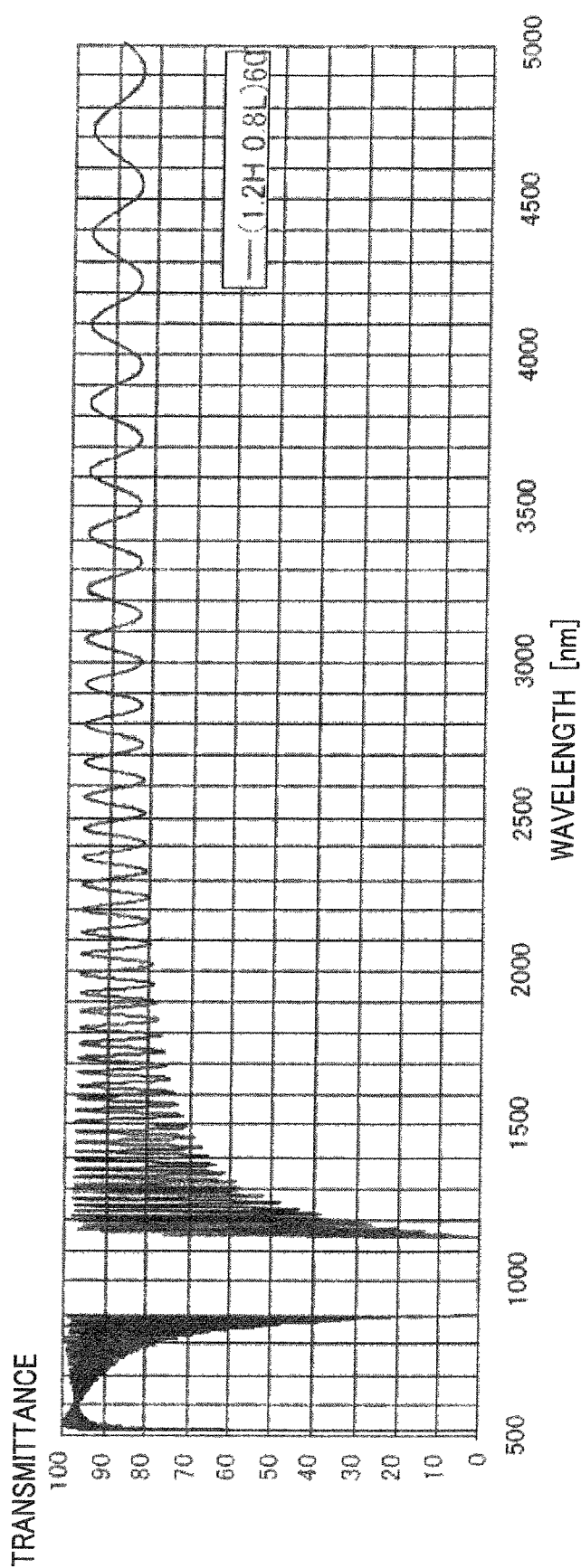
FIG. 32 is an explanatory diagram for explaining, concerning the present invention, a principle of occurrence of a low-order reflection band with respect to a main reflection band in a waveguide in which cyclic unevenness is formed and is a diagram showing a state of a reflection band at the time when predetermined incident light is made incident on a multilayer reflection film in which dielectric films having different refractive indexes overlap by two layers per period.

FIG. 32 is an explanatory diagram for explaining, concerning the present invention, a principle of occurrence of a low-order reflection band with respect to a main reflection band in a waveguide in which cyclic unevenness is formed and is a diagram showing a state of a reflection band at the time when predetermined incident light is made incident on a multilayer reflection film in which dielectric films having different refractive indexes overlap by two layers per period. FIG. 33 to FIG. 36 are the same explanatory diagrams and are diagrams respectively showing states of the reflection band at the time when predetermined incident light is made incident on multilayer reflection films in which dielectric films having different refractive indexes overlap by three layers to six layers per period.

In FIG. 32, there is description "(1.2H 0.8L)60)". This indicates a configuration of the multilayer reflection film having characteristics shown in the figure. The meaning of the description is the same in FIG. 33 to FIG. 36. FIG. 33 to FIG. 36 respectively show configurations of the multilayer reflection films.

Numerical values in parentheses indicate thickness of a thin film layer. This is film thickness representation for describing $\lambda s/4$ as 1.0, where $\lambda s$ represents a reference wavelength of film thickness description (in examples in FIG. 32 to FIG. 36, $\lambda s$=1000 nm). H and L in the parentheses are signs indicating characteristics of a thin film (H indicates a high refractive index layer and L indicates a low refractive index layer). A numerical value outside the parentheses indicates that a film configuration in the parentheses is repeatedly laminated numbered times indicated by the numerical value.

In the configurations of the multilayer reflection films shown in FIG. 32 to FIG. 36, when the lamination cycle L1 of the thin film explained above (see Equation (1), equivalent to the cyclic length L of the cyclic unevenness in the waveguide) is calculated, for example, a lamination cycle equation of the thin film in FIG. 32 is as follows:

$$L1=(1.2+0.8)\times\lambda s/4=\lambda s/2(\lambda s=1000 \text{ nm})$$

It turns out that a main reflection band occurs in a position satisfying Equation (1):

$$\lambda c=2\times L1=2\times(\lambda s/2)=\lambda s(\lambda s=1000 \text{ nm})$$

Figure 36:
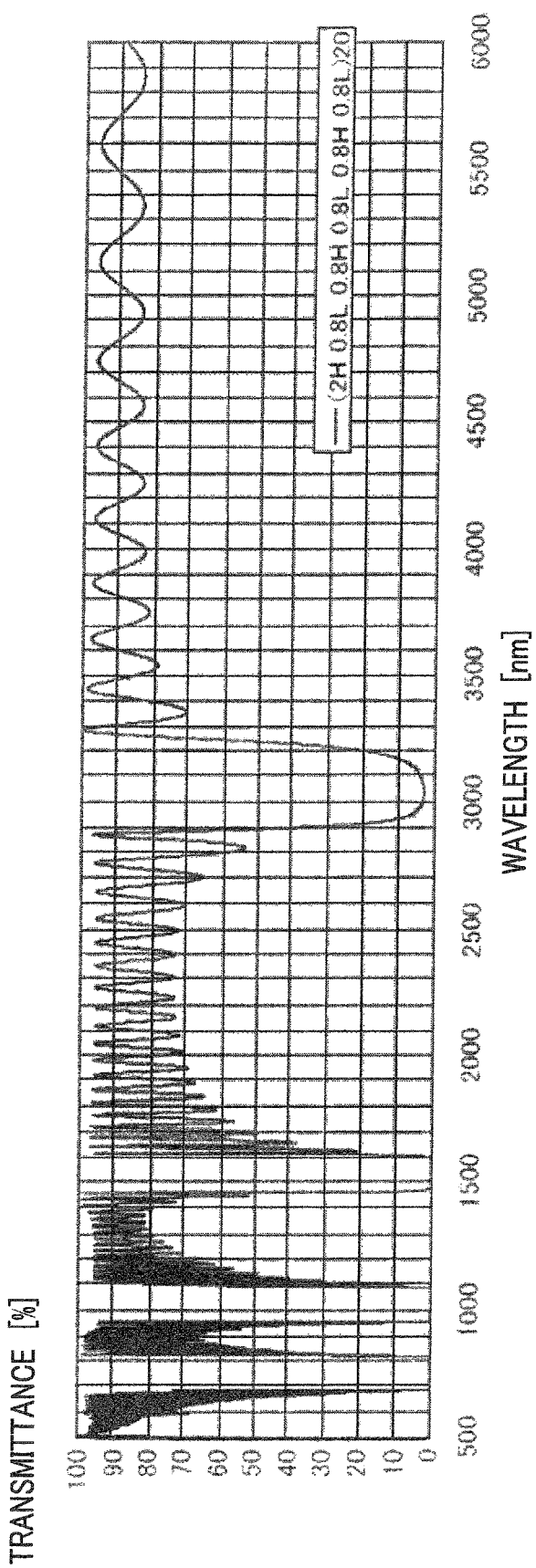
FIG. 36 is an explanatory diagram for explaining, concerning the present invention, the principle of occurrence of the low-order reflection band with respect to the main reflection band in the waveguide in which the cyclic unevenness is formed and is a diagram showing a state of the reflection band at the time when predetermined incident light is made incident on a multilayer reflection film in which dielectric films having different refractive indexes overlap by six layers per period.

Similarly, the lamination cycle L1 of the thin film in the configuration "(2.0H 0.8L 0.8H 0.8L 0.8H 0.8L) 20" in FIG. 36 is calculated as follows:

$$L1=(2.0+0.8+0.8+0.8+0.8+0.8)/3\times\lambda s/4=\lambda s/2$$
$$(\lambda p=1000 \text{ nm})$$

As in the example shown in FIG. 32, a main reflection band occurs in a position satisfying Equation (1).

The numerical values in the parentheses are averaged by "3" of HL lamination times in the parentheses. An argument concerning validity of the averaging of the numerical values is omitted here.

Figure 33:
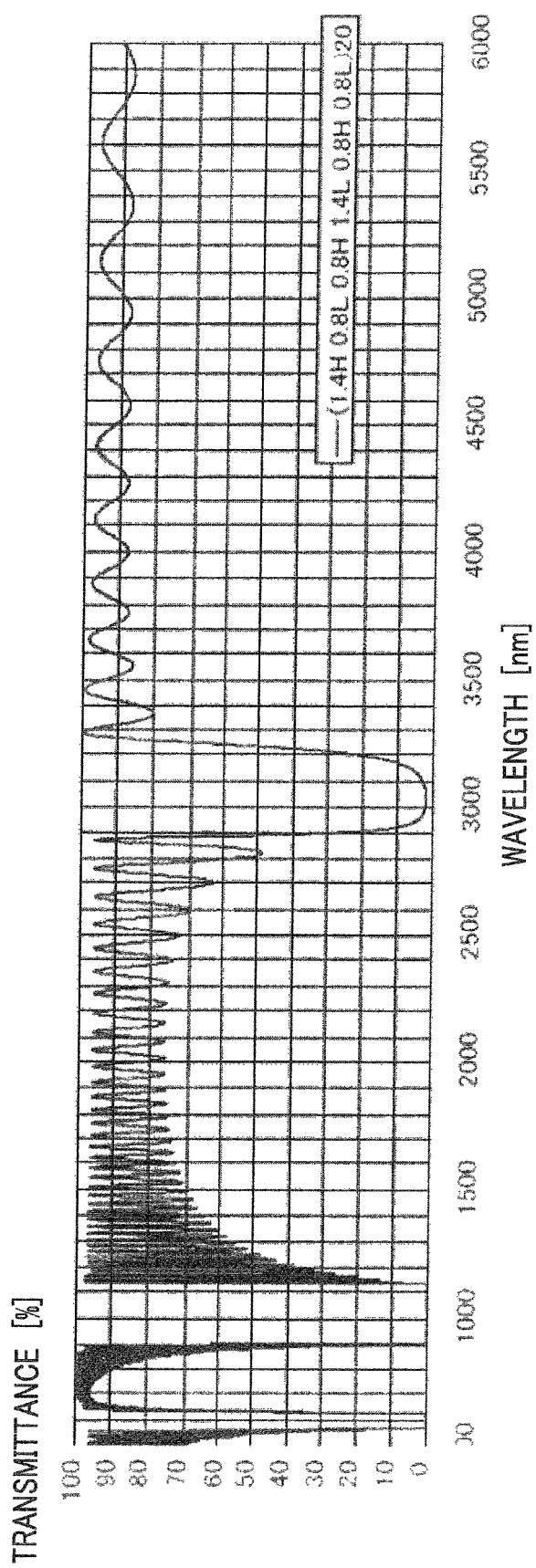
FIG. 33 is an explanatory diagram for explaining, concerning the present invention, the principle of occurrence of the low-order reflection band with respect to the main reflection band in the waveguide in which the cyclic unevenness is formed and is a diagram showing a state of the reflection band at the time when predetermined incident light is made incident on a multilayer reflection film in which dielectric films having different refractive indexes overlap by three layers per period.
Figure 34:
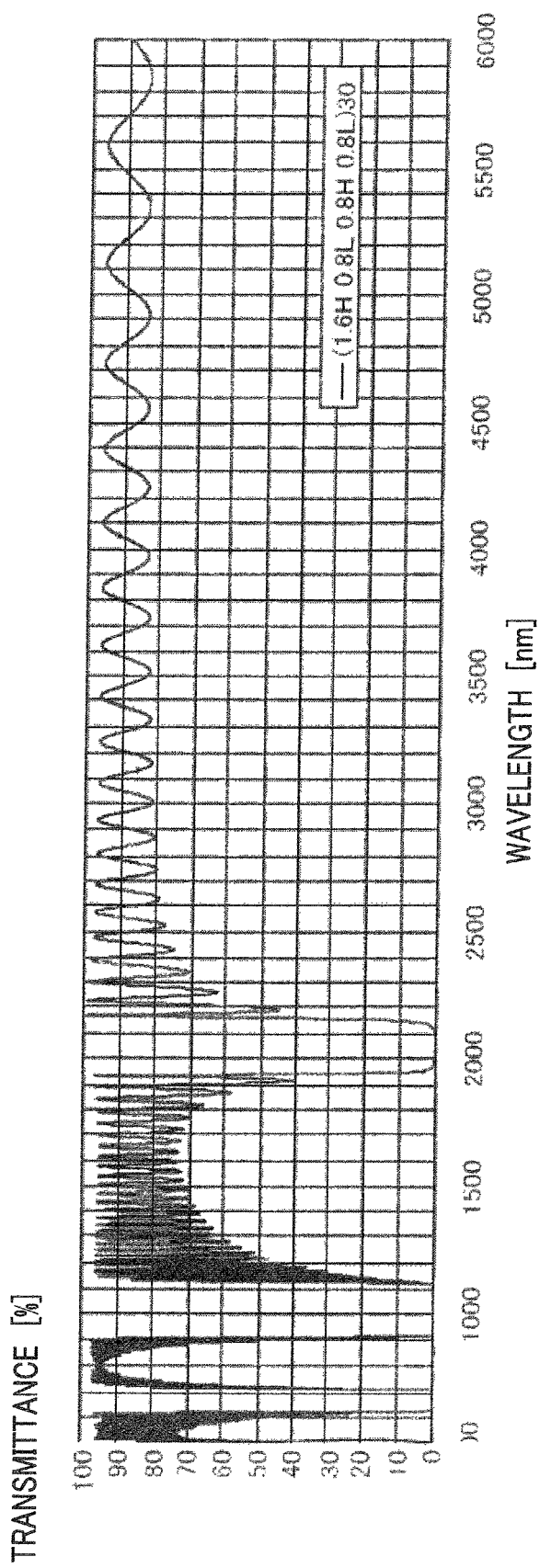
FIG. 34 is an explanatory diagram for explaining, concerning the present invention, the principle of occurrence of the low-order reflection band with respect to the main reflection band in the waveguide in which the cyclic unevenness is formed and is a diagram showing a state of the reflection band at the time when predetermined incident light is made incident on a multilayer reflection film in which dielectric films having different refractive indexes overlap by four layers per period.
Figure 35:
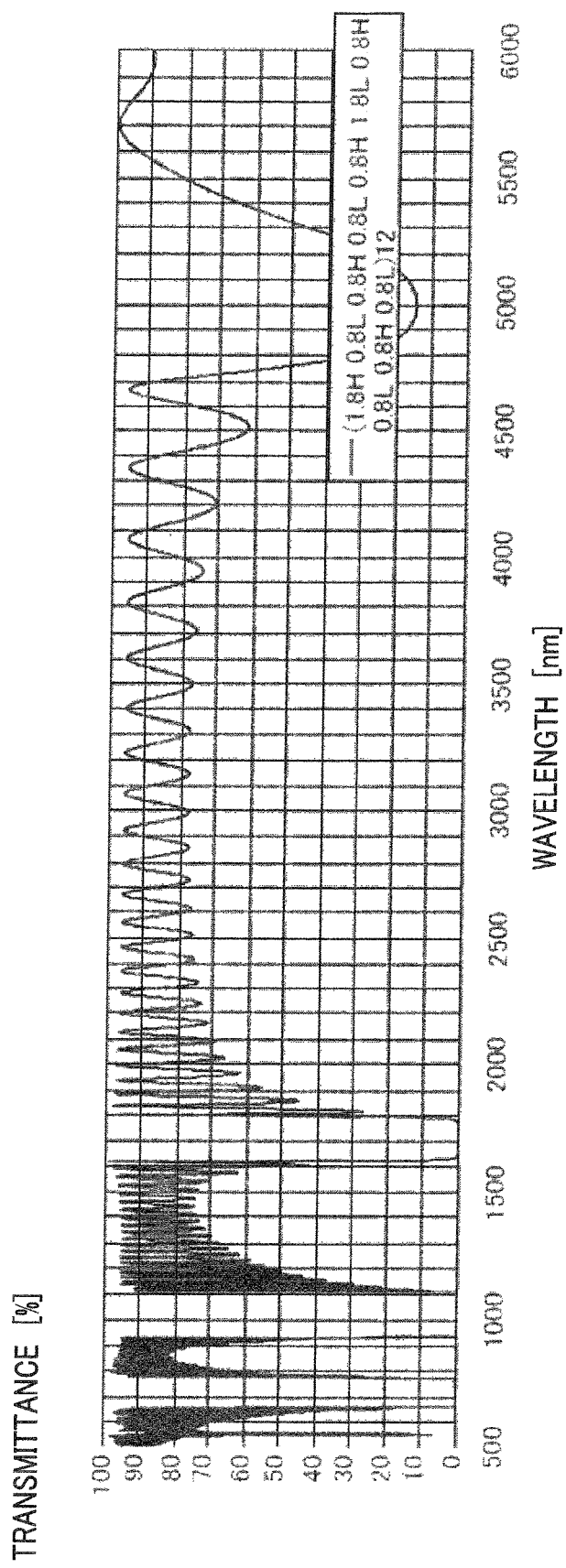
FIG. 35 is an explanatory diagram for explaining, concerning the present invention, the principle of occurrence of the low-order reflection band with respect to the main reflection band in the waveguide in which the cyclic unevenness is formed and is a diagram showing a state of the reflection band at the time when predetermined incident light is made incident on a multilayer reflection film in which dielectric films having different refractive indexes overlap by five layers per period.

This behavior is the same concerning the examples shown in FIG. 33 and FIG. 34. A main reflection band occurs in a position satisfying Equation (1). This is a phenomenon similar to the phenomenon in which the main reflection band occurs when the following relational equation in the waveguide explained above is satisfied:

$$L/2=\lambda g/4 \qquad \text{Equation (6)}$$

In other words, in a case of two layers per period as shown in FIG. 32, a reflection band does not occur in a band having a wavelength longer than the main reflection band.

On the other hand, in the examples including disturbance in a long cycle shown in FIG. 33 to FIG. 36, a reflection band (a low-order reflection band) is present in a wavelength band different from the main reflection band.

For example, in the example shown in FIG. 36, repeated lamination of six layers "(2.0H 0.8L 0.8H 0.8L 0.8H 0.8L) 20" is present as disturbance in a longer cycle than two layers. Consequently, a low-order reflection band occurs in wavelengths ($\lambda$=1500 nm and $\lambda$=3000 nm) longer than a main reflection band ($\lambda$=1000 nm) at L1=$\lambda s/2$.

This behavior is the same in the examples shown in FIG. 33 and FIG. 34. A reflection band (a low-order reflection band) also occurs in a band having a wavelength longer than the main reflection band. In other words, from the behavior shown in FIGS. 33 to 36, the inventor inferred that a low-order reflection band could occur in the waveguide in the same manner as in the multilayer reflection film.

As explained above, in the flexible waveguide as in the present invention, considering that a "cyclic structure" formed inside the waveguide can take a complicated form, the inventor found that, in the flexible waveguide of the present invention, a plurality of different reflection bands (low-order reflection bands) could occur in, in particular, a longer wavelength band different from the main reflection band and developed the invention concerning a form of a flexible waveguide that can avoid influence of these low-order reflection bands.

Note that, as the low-order reflection band, in a range of examination performed by the inventor so far, a low-order reflection band that occurs in a range of a three times wavelength with respect to a wavelength region where a main reflection band occur relatively easily occurs. Low-order reflection bands up to a low-order reflection band that occurs in a range of a five times wavelength sometime occur, although the low-order reflection bands are weak. It is known that the low-order reflection bands easily affect a transmission characteristic of the waveguide. In other words, as a result of earnest researches, the inventor found that it is necessary to avoid the low-order reflection bands in order to stabilize characteristics of the flexible waveguide.

When a result obtained here is formulated and applied to a deriving process of the relational Expression (11) described above, even if cyclic unevenness is present in the waveguide, it is possible to calculate the cyclic length L that can obtain a satisfactory transmission characteristic.

In other words, when the result obtained here is formulated, the result can be represented as follows.

For example, when a center wavelength of a low-order reflection band that occurs in a five times wavelength is represented as $\lambda 1r$, "avoiding the center wavelength $\lambda 1r$ being included in a transmission band (a range of the wavelength band W in FIG. 18)" can be represented by the following Expression (10A) according to Expression (10) described above.

$$\lambda 1r<\lambda c/2 \qquad \text{Expression (10A)}$$

Since the center wavelength of the low-order reflection band that easily affects the transmission characteristic of the waveguide has a wavelength five times as large as the wavelength of the main reflection band, the center wavelength $\lambda 1r$ is represented as follows:

$$\lambda 1r=5\times\lambda mr \qquad \text{Equation (10B)}$$

When $\lambda 1r$ and $\lambda mr$ are erased from Expression (10A), Equation (10B), and Equation (6B) described above, in the cyclic length L represented by the following expression:

$$L<\lambda c/(20\times\sqrt{\varepsilon r}) \qquad \text{Expression (11B)}$$

possibility of being affected by the low-order reflection band is extremely low even if a "cyclic structure" formed inside the waveguide has a complicated form including a structure of a longer cycle that cannot be represented by the cyclic length L of simple unevenness. A satisfactory transmission characteristic is obtained.

Note that, in the above explanation, the expression is developed considering that it is desirable to avoid the wavelengths up to the five times wavelength in which the main reflection band occurs. However, the low-order reflection band that relatively easily occurs is up to a range of a three times wavelength with respect to the wavelength region where the main reflection band occurs. Therefore, a certain effect is recognized in improvement of the transmission characteristic even when wavelengths up to the three times wavelength of the main reflection band are avoided.

In other words, even in the cyclic length L represented by the following expression:

$$L < \lambda c/(12 \times \sqrt{\varepsilon r})\qquad\text{Expression (11C)}$$

a satisfactory transmission characteristic in a form including the structure of the long cycle can be expected.

<Specific Explanation of Third Embodiment>

The flexible waveguide according to the third embodiment is more specifically explained in view of the presence of the "low-order reflection band" explained above.

Figure 37:
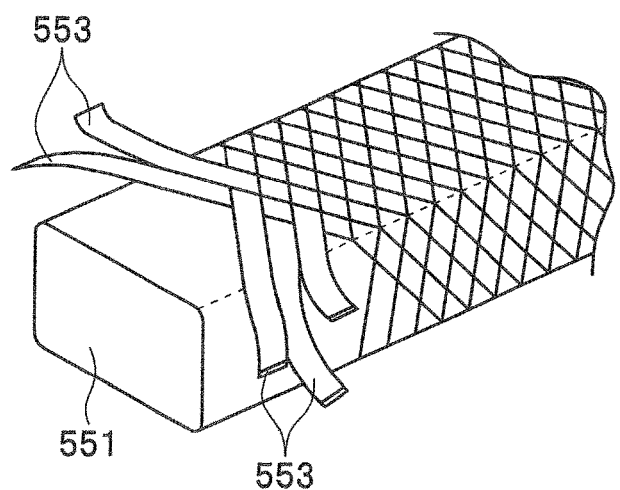
FIG. 37 is a main part sectional view showing an external conductor assuming a braid shape and an inner dielectric in a flexible waveguide in a third embodiment of the present invention.
Figure 38:
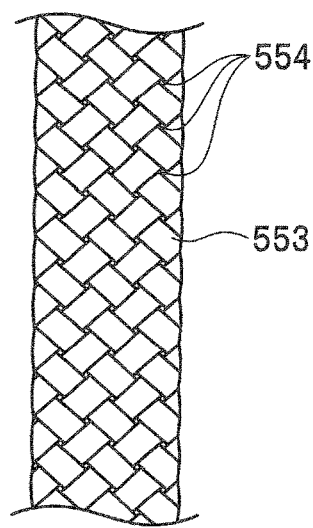
FIG. 38 is an exterior view showing an exterior of the external conductor assuming the braid shape in the flexible waveguide in the third embodiment.

As the flexible waveguide according to the third embodiment, as in the second embodiment, realistically, a flexible waveguide in which an external conductor assuming a shape considering flexibility is arranged shown in FIG. 37, FIG. 38, or the like is assumed.

Concerning the flexible waveguide according to the third embodiment, in order to more accurately grasp electromagnetic physical properties such as a transmission loss relating to the realistic flexible waveguide or mechanical physical properties such as flexibility, considering that a radio wave of a millimeter wave (including a submillimeter wave) is propagated, an approximate simulation model is set concerning a material, a shape, and the like in the realistic flexible waveguide and set as the flexible waveguide according to the third embodiment.

The flexible waveguide according to the third embodiment is explained below. In addition, characteristics such as a material, a shape, and a transmission loss of the flexible waveguide conform to the characteristics of the assumed realistic flexible waveguide.

Figure 39:
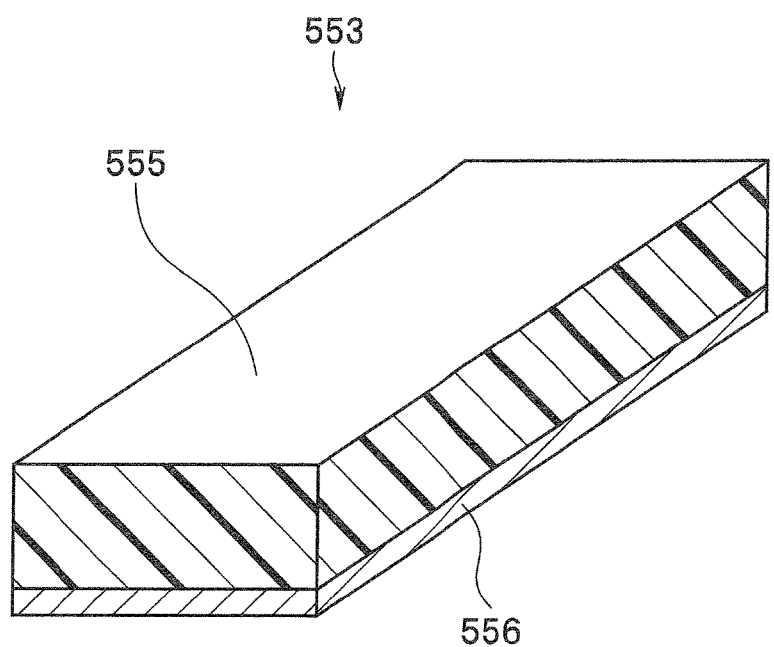
FIG. 39 is a main part enlarged sectional view showing a configuration of an external conductor formed by braiding flat foil yarns in a braid shape in the flexible waveguide in the third embodiment.

FIG. 37 is a main part sectional view showing an external conductor formed by braiding flat foil yarns in a braid shape and an inner dielectric in the flexible waveguide in the third embodiment of the present invention. FIG. 38 is an exterior view showing an exterior of the external conductor formed by braiding the flat foil yarns in the braid shape in the flexible waveguide in the third embodiment. FIG. 39 is a main part enlarged sectional view showing a configuration of an external conductor formed by braiding the flat foil yarns in the braid shape in the flexible waveguide in the third embodiment.

Figure 40:
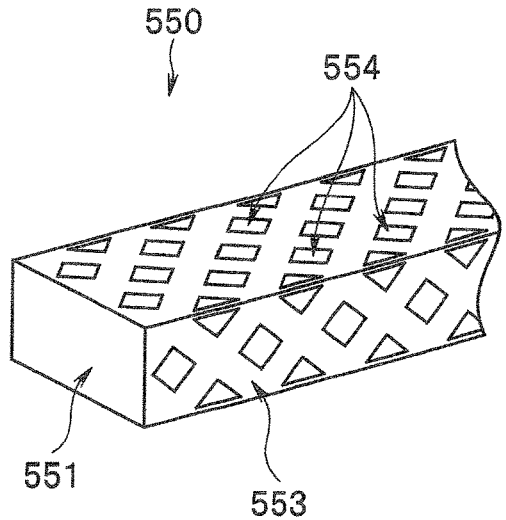
FIG. 40 is a main part perspective view showing flat foil yarns and braiding holes configuring an external conductor assuming a braid shape and an inner dielectric in a simulation model relating to the flexible waveguide in the third embodiment.
Figure 41:
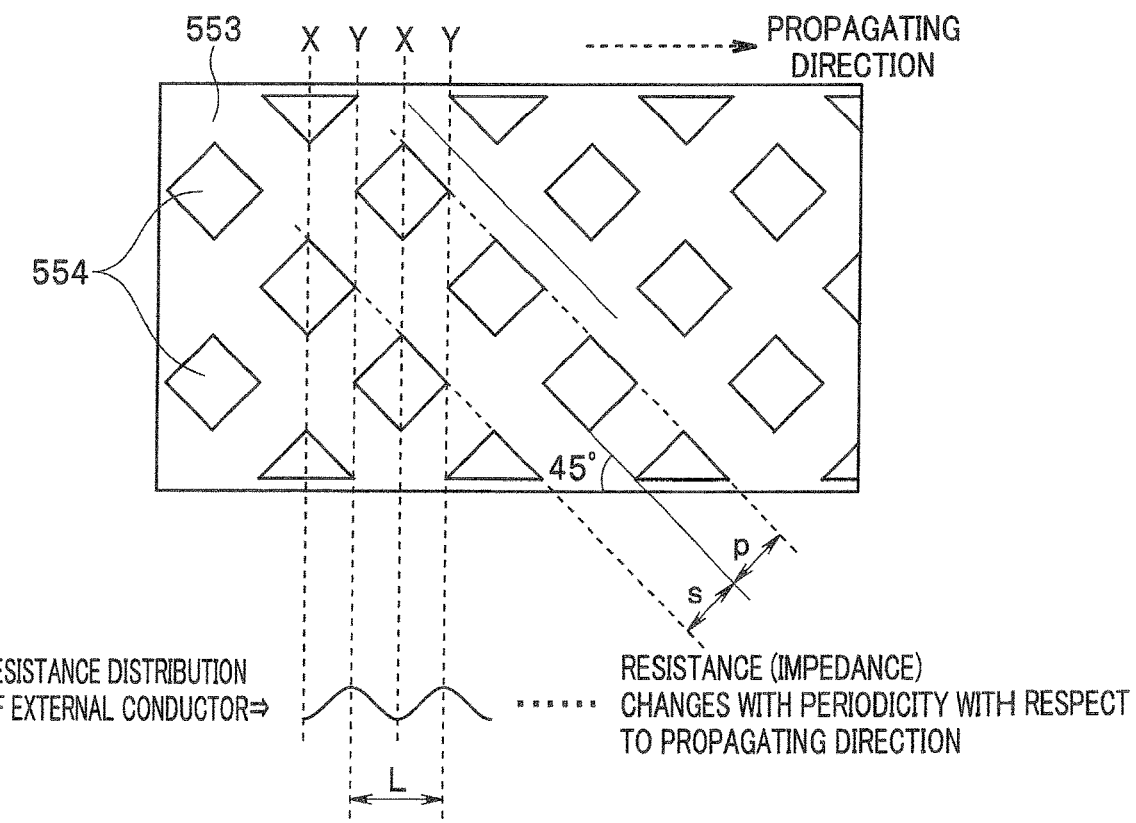
FIG. 41 is an explanatory diagram showing a positional relation between the flat foil yarns and the braiding holes having cyclicity configuring the external conductor assuming the braid shape in the simulation model relating to the flexible waveguide in the third embodiment.
Figure 42:
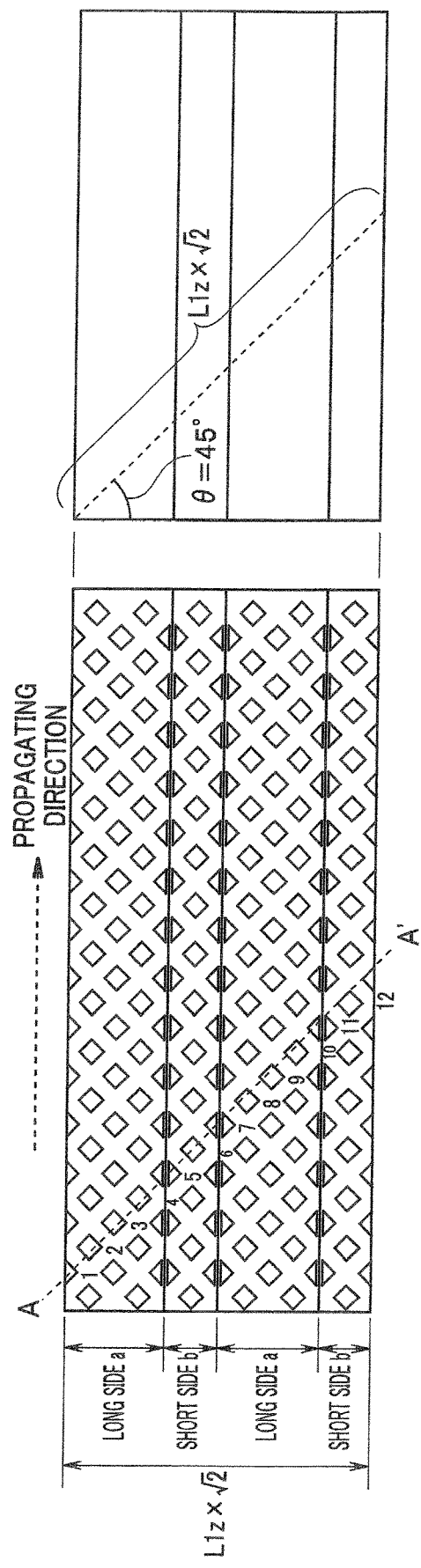
FIG. 42 is an exploded view in which the external conductor assuming the braid shape is exploded in an entire peripheral direction of the waveguide in the simulation model relating to the flexible waveguide in the third embodiment.
Figure 43:
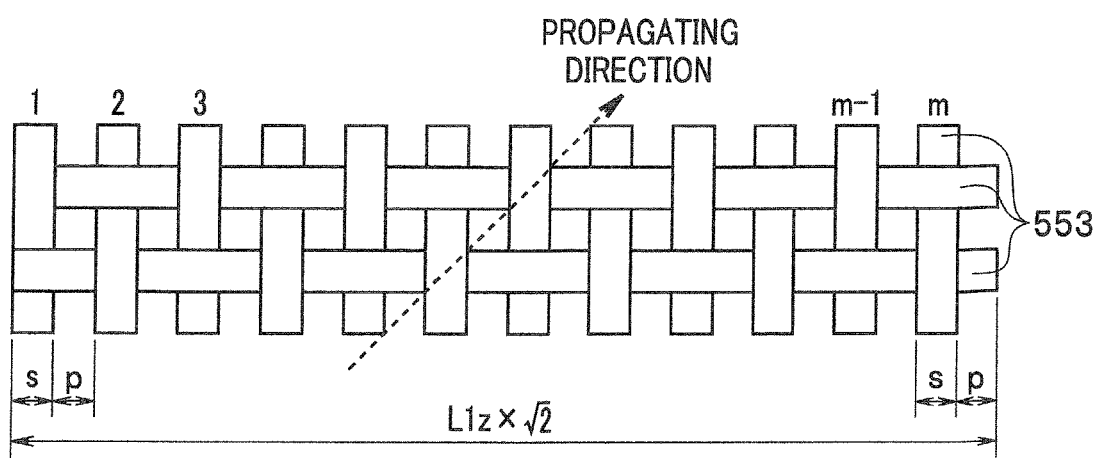
FIG. 43 is a main part enlarged view showing a surface along A-A' in FIG. 42 concerning the flat foil yarns and the braiding holes having cyclicity configuring the external conductor assuming the braid shape in the simulation model relating to the flexible waveguide in the third embodiment.
Figure 44:
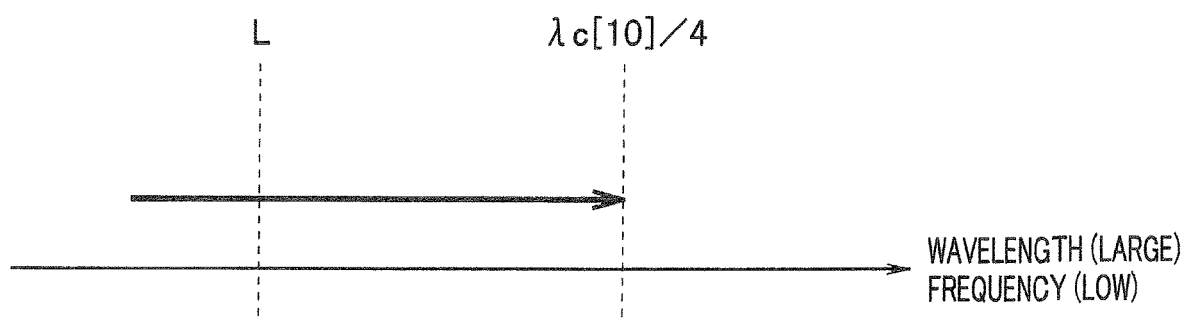
FIG. 44 is diagram showing a relation between a period L of the braiding holes and a cutoff wavelength in the simulation model relating to the flexible waveguide in the third embodiment.

FIG. 40 is a main part perspective view showing flat foil yarns and braiding holes configuring an external conductor assuming a braid shape and an inner dielectric in a simulation model relating to the flexible waveguide in the third embodiment. FIG. 41 is an explanatory diagram showing a positional relation between the flat foil yarns and the braiding holes having cyclicity configuring the external conductor in the simulation model. FIG. 42 is an exploded view in which the external conductor is exploded in an entire peripheral direction of the waveguide in the simulation model. FIG. 43 is a main part enlarged view showing a surface along A-A' in FIG. 42 concerning the flat foil yarns and the braiding holes having cyclicity configuring the external conductor in the simulation model. FIG. 44 is a diagram showing a relation between a cycle L of the braiding holes and a cutoff wavelength in the simulation model relating to the flexible waveguide in the third embodiment.

In the third embodiment, as in the first embodiment, a distal end portion of a flexible waveguide 550 according to the third embodiment that allows a millimeter wave or a submillimeter wave to pass is connected to the proximal end side of the driver IC 23 across the transmission and reception antenna 27 integrated with the package of the driver IC 23.

As in the first embodiment, the flexible waveguide 550 has flexibility. After a distal end side of the flexible waveguide 550 is connected to the driver IC 23 disposed at the distal end rigid portion 10, the flexible waveguide 550 is extended toward the proximal end side of the insertion section 6.

Further, as in the first embodiment, after being inserted through an inside of the insertion section 6 including the bending section 9 and the flexible tube section further on the proximal end side such as the further proximal end side relative to the driver IC 23 in the insertion section 6, that is, a further proximal end side portion relative to a disposition part of the driver IC 23 at the distal end rigid portion 10, the flexible waveguide 550 is inserted through the inside of the operation section 7 and the inside of the universal cord 8 and disposed in a position leading to the video processor 3.

As in the first embodiment, the flexible waveguide 550 according to the third embodiment is a signal transmission line connecting the image pickup unit 20 and the image processing section (the image processing circuit 31) in the video processor 3. At least a part of the flexible waveguide 550 is a waveguide for propagating a millimeter wave or a submillimeter wave.

<Inner Dielectric and External Conductor in Flexible Waveguide According to Third Embodiment>

As shown in FIG. 37, in the third embodiment as well, the flexible waveguide 550 includes a linear inner dielectric 551 on an inside, a dielectric constant of which is uniform in the longitudinal direction and a cross section of which assumes the same shape in the longitudinal direction, and an external conductor 553 disposed in a position covering an outer periphery of the inner dielectric 551.

Note that, in the third embodiment as well, "a dielectric constant is uniform" means that the dielectric constant is uniform in terms of a dimension in a wavelength order of a radio wave (a millimeter wave or a submillimeter wave) propagating inside the waveguide.

In other words, a dielectric constant distribution by a structure having a dimension different from the wavelength order by one to two or more digits does not affect the radio wave propagating inside the waveguide. Therefore, in the third embodiment as well, this is included in the representation "a dielectric constant is uniform".

<Specific Dielectric Constant and Shape of Inner Dielectric in Third Embodiment>

A specific dielectric constant of the inner dielectric 551 is set to a specific dielectric constant $\varepsilon_r=2.0$ in the flexible waveguide 550 (which is the simulation model) in the third embodiment. On the other hand, the inner dielectric 551 assumes a sectional shape, a ratio of a long side and a short side of which is constant in the longitudinal direction. The long side and the short side are respectively set to a long side a=2.66 mm and a short side b=1.33 mm.

<Shape of External Conductor in Third Embodiment>

On the other hand, the external conductor 553 in the third embodiment is configured by, for example, a flat foil yarn including a plurality of belt-like sections including a metal layer (a metal substance), a cross section of the flat foil yarn perpendicular to an extending axis assuming a rectangular cross section.

FIG. 39 is a main part enlarged sectional view showing a configuration of an external conductor formed by braiding flat foil yarns in a braid shape in the flexible waveguide in the third embodiment. As shown in FIG. 39, a cross section of the flat foil yarn, which is a belt-like section in the third embodiment, perpendicular to the extending axis assumes a rectangular cross section. The flat foil yarn includes a ground layer 555 including a nonmetal substance such as resin and a metal layer 556 including a metal substance.

The plurality of flat foil yarns extend to be wound, in a state in which side edge portions of all the flat foil yarns form a predetermined angle with respect to the waveguide longitudinal axis, such that flat sections of the flat foil yarns are wound on an outer peripheral surface of the inner dielectric 551 with the metal layers 556 disposed on a side in contact with the inner dielectric 551 and, the plurality of flat foil yarns are braided to form a braid shape with one another (see FIG. 37 and FIG. 38).

The cyclic structure in the third embodiment is a structure satisfying the following expression:

$$(L1z/M) < \lambda c/(4 \times \sqrt{\varepsilon r})$$

where $\lambda c$ represents a cutoff wavelength in the basic mode of the waveguide, $\varepsilon r$ represents a specific dielectric constant of the inner dielectric 551, L1z represents an entire peripheral dimension of the waveguide cross section, and M represents the number of belt-like sections used to form the braid shape form.

Note that the external conductor 553 includes the predetermined metal layer section (the metal layer 556) as explained above. Electric conductivity of the metal layer section is set to 59×10$^6$ S/m equivalent to the electric conductivity of pure copper. Note that although the electric conductivity is uniquely determined here, in the present invention, the electric conductivity of the metal layer section is not limited to this. In the embodiment, it is desirable to use a metal layer having high electric conductivity.

Note that, as explained above, the flat foil yarn, which is the external conductor 553 in the third embodiment, is configured to include the metal layer 556 arranged on the side in contact with the inner dielectric 551 and the ground layer 555 on the outer side. However, the flat foil yarn is not limited to this and may be configured by only the metal layer.

In the third embodiment, as explained above, when the plurality of flat foil yarns, which form the external conductor 553, are wound on the outer periphery of the inner dielectric 551 at a winding angle of 45 degrees and braided in a braid shape, holes called "braiding holes" are formed among the yarns. Note that, in FIG. 40 and FIG. 41, the braiding holes are indicated by a reference numeral 554.

In the braiding holes 554, a surface of the inner dielectric 551 on a lower side is exposed in portions of "holes".

As shown in FIG. 41, when the braiding holes 554 relating to the flat foil yarns braided in the braid shape are viewed from a side of the waveguide, in a very small section concerning a region perpendicular to the longitudinal axis (the propagating direction) of the waveguide, there are regions where ratios of the portions of the "holes" (that is, portions where the inner dielectric 551 is exposed) and metal portions of the flat foil yarns themselves are substantially the same (lines indicated by a sign X in FIG. 41) and regions that are entirely metal portions (lines indicated by a sign Y in FIG. 41).

In this way, in the flexible waveguide 550 in the third embodiment, the external conductor 553 is formed such that the ratio of the metal portions cyclically changes in the longitudinal direction (the propagating direction) of the waveguide. In other words, in the flexible waveguide 550 in the third embodiment, a cyclic shape change occurs in the longitudinal direction in the external conductor 553 and a resistance (impedance) distribution of the external conductor changes with predetermined cyclicity in the propagating direction.

On the other hand, in the third embodiment as well, it can be said that the cyclic unevenness 554 is formed between the inner dielectric 551 and the metal layer of the external conductor 553.

In other words, the cyclic unevenness 554, which is the cyclic structure, in the third embodiment can be represented by the cyclic length L as follows:

$$L = (s+p)/\sqrt{2} \qquad \text{Equation (23)}$$

where s represents a width of the flat foil yarn and p represents length of one side of the braiding hole 554.

When only a "main reflection band" is considered in the flexible waveguide 550 in the third embodiment, the main reflection band is absent in a frequency band transmitted only in the basic mode (TE10) when the cyclic length L explained above (the cyclic unevenness 554 explained above) satisfies the following expression:

$$L < \lambda c/(4 \times \sqrt{\varepsilon r}) \qquad \text{Expression (11)}$$

<Relation Between Waveguide Dimensions According to Third Embodiment and Number of Braided Strings (Only Main Reflection Band is Considered)>

First, a relation between dimensions of the waveguide according to third embodiment and the number of braided strings is verified concerning a case in which only the "main reflection band" explained above is considered.

As explained above, FIG. 42 is an exploded view in which the external conductor is exploded in an entire peripheral direction of the waveguide in the simulation model according to the third embodiment. FIG. 43 is a main part enlarged view showing a surface along A-A' in FIG. 42 concerning the flat foil yarns and the braiding holes having cyclicity configuring the external conductor. FIG. 44 is diagram showing a relation between a cycle L of the braiding holes and a cutoff wavelength in the simulation model relating to the flexible waveguide in the third embodiment.

In FIG. 42, a line indicated by A-A' indicates the number of braidings (the number of wound yarns). In a case of FIG. 42, the line indicates that the number of yarns is twelve (twelve braidings). In FIG. 42, there is a relation of the following equation:

$$L1z = 2 \times (a+b) \qquad \text{Equation (24)}$$

where L1z represents an entire peripheral dimension of a waveguide cross section, "a" represents a waveguide long side, and "b" represents a waveguide short side.

As shown in FIG. 43, the flowing relation holds on a surface indicated by A-A':

$$(s+p) \times M = L1z \times \sqrt{2} \qquad \text{Equation (25)}$$

where L1z represents the entire peripheral dimension of the waveguide cross section, s represents the width of the yarn, p represents the length of one side of the braiding hole, and M represents the number of braidings.

Note that Equation (25) always holds when the external conductor 553 is configured by braid (braid cord) as in the third embodiment.

According to Equations (23) and (25), when (s+p) is erased, the following equations are obtained:

$$((s+p))/\sqrt{2} \times M = L1z$$

$$L = L1z/M \qquad \text{Equation (26)}$$

As it is seen from Equation (26), in the flexible waveguide 550 in the third embodiment, the cyclic length L of the external conductor changes when the "number of braidings M" of braid changes.

As shown in FIG. 44, when a value of the cyclic length L satisfies the following expression:

$$L < \lambda c/(4 \times \sqrt{\varepsilon r}) \qquad \text{Expression (11)}$$

within a range in the basic mode, a reflection band is absent in a wavelength band in the basic mode (TE10). A satisfactory transmission characteristic is obtained even if cyclic unevenness (the cyclic unevenness 554 explained above) is present in the waveguide.

From this relation, if the "number of braidings M" is set large, a denominator of Equation (26) increases and magnitude of the cyclic length L relating to the external conductor 553 decreases.

On the other hand, as explained above, the entire periphery L1z of the flexible waveguide 550 is as follows:

$$L1z = 2 \times (a+b) \qquad \text{Equation (27)}$$

From the waveguide theory, in the third embodiment as well, as in the first and second embodiments, if a ratio of the long side "a" and the short side "b" of the waveguide is set to 2:1 as follows, the wavelength band can be secured wide:

$$b = a/2 \qquad \text{Equation (28)}$$

According to Equations (27) and (28), the following equations are obtained:

$$L1z = 2 \times (a + a/2)$$

$$L1z = 3 \times a \qquad \text{Equation (29)}$$

When L1z is erased from Equations (26) and (29), the following equation is obtained:

$$L = 3 \times a/M \qquad \text{Equation (30)}$$

The cutoff wavelength λc can be represented as follows using the waveguide long side "a":

$$\lambda c = 2 \times a \times \sqrt{\varepsilon r} \qquad \text{Equation (31)}$$

Accordingly, from Expression (11) and Equations (30) and (31), $$3 \times a/M < (2 \times a \times \sqrt{\varepsilon r})/(4 \times \sqrt{\varepsilon r})$$

"a" and εr can be erased. In other words, the following expression is obtained:

$$M > 6 \qquad \text{Expression (32)}$$

In this way, in the external conductor 553 by braid like the flexible waveguide 550 in the third embodiment, only in a case in which only the main reflection band is considered, when Expression (32) holds, that is, if the number of braided strings exceeds six, the main reflection band is absent in the frequency band transmitted only in the basic mode (TE10).

<Transmission Characteristic (Simulation Model) of Flexible Waveguide in Third Embodiment>

A transmission characteristic of the flexible waveguide in the third embodiment is verified using a simulation model, in which the number of braided strings M is set as a parameter, concerning a case in which not only the "main reflection band" but also the "low-order reflection band" explained above is considered.

Figures 45, 46:
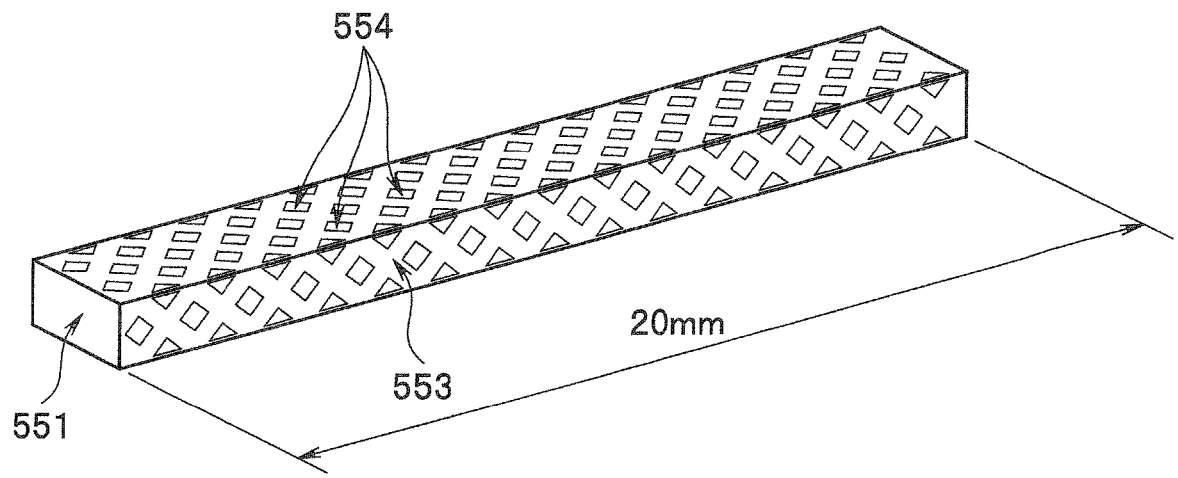
FIG. 45 is an exterior perspective view showing the simulation model relating to the flexible waveguide in the third embodiment.
FIG. 46 is a table diagram showing a relation among the number of braided strings, a yarn width, and a hole diameter of the braiding hole set in the simulation model relating to the flexible waveguide in the third embodiment.
Figure 47:
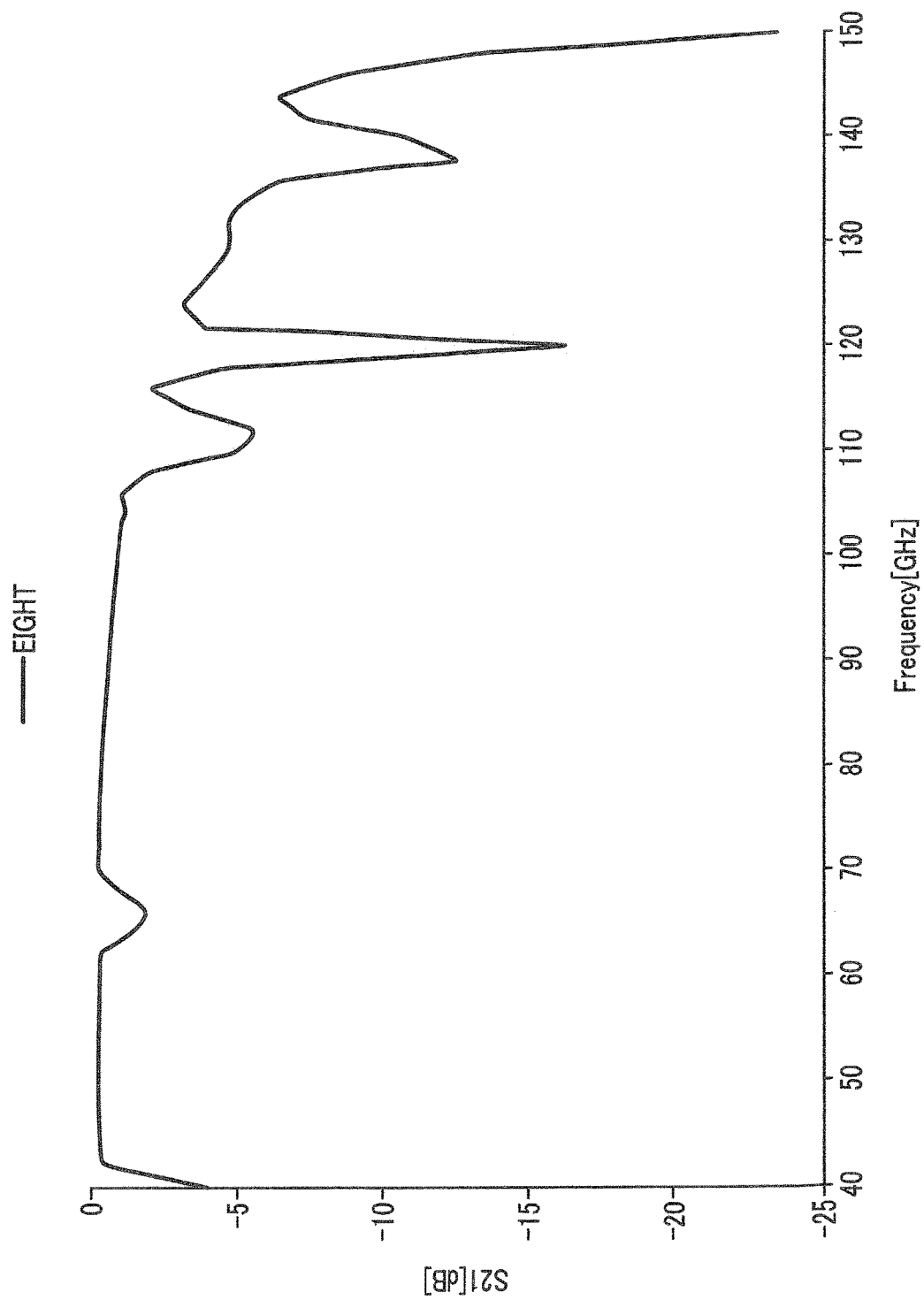
FIG. 47 is a diagram showing a transmission characteristic relating to a low-order reflection band in a case of the number of braided strings=8 in the simulation model relating to the flexible waveguide in the third embodiment.
Figure 48:
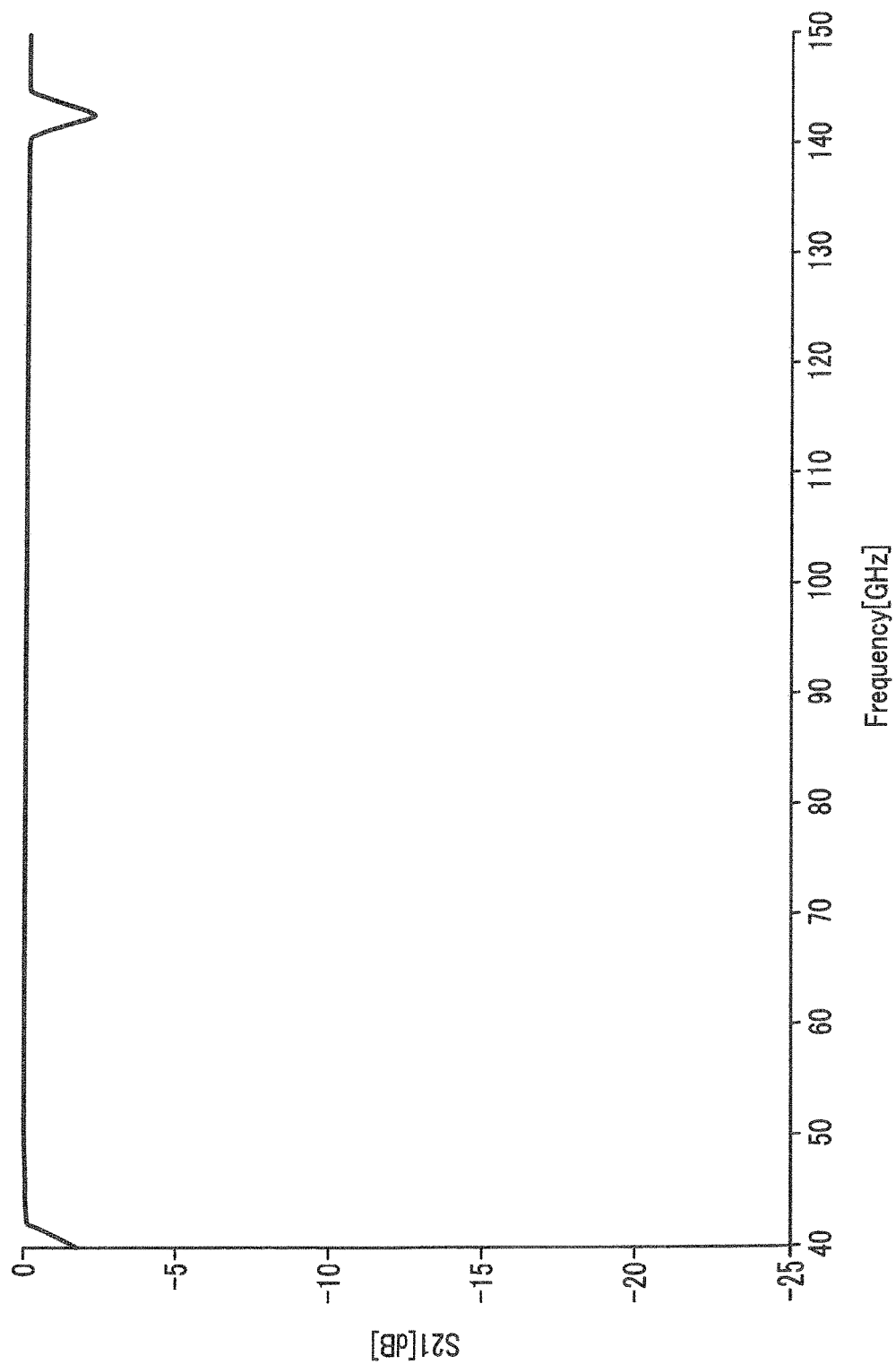
FIG. 48 is a diagram showing a transmission characteristic relating to the low-order reflection band in a case of the number of braided strings=16 in the simulation model relating to the flexible waveguide in the third embodiment.
Figure 49:
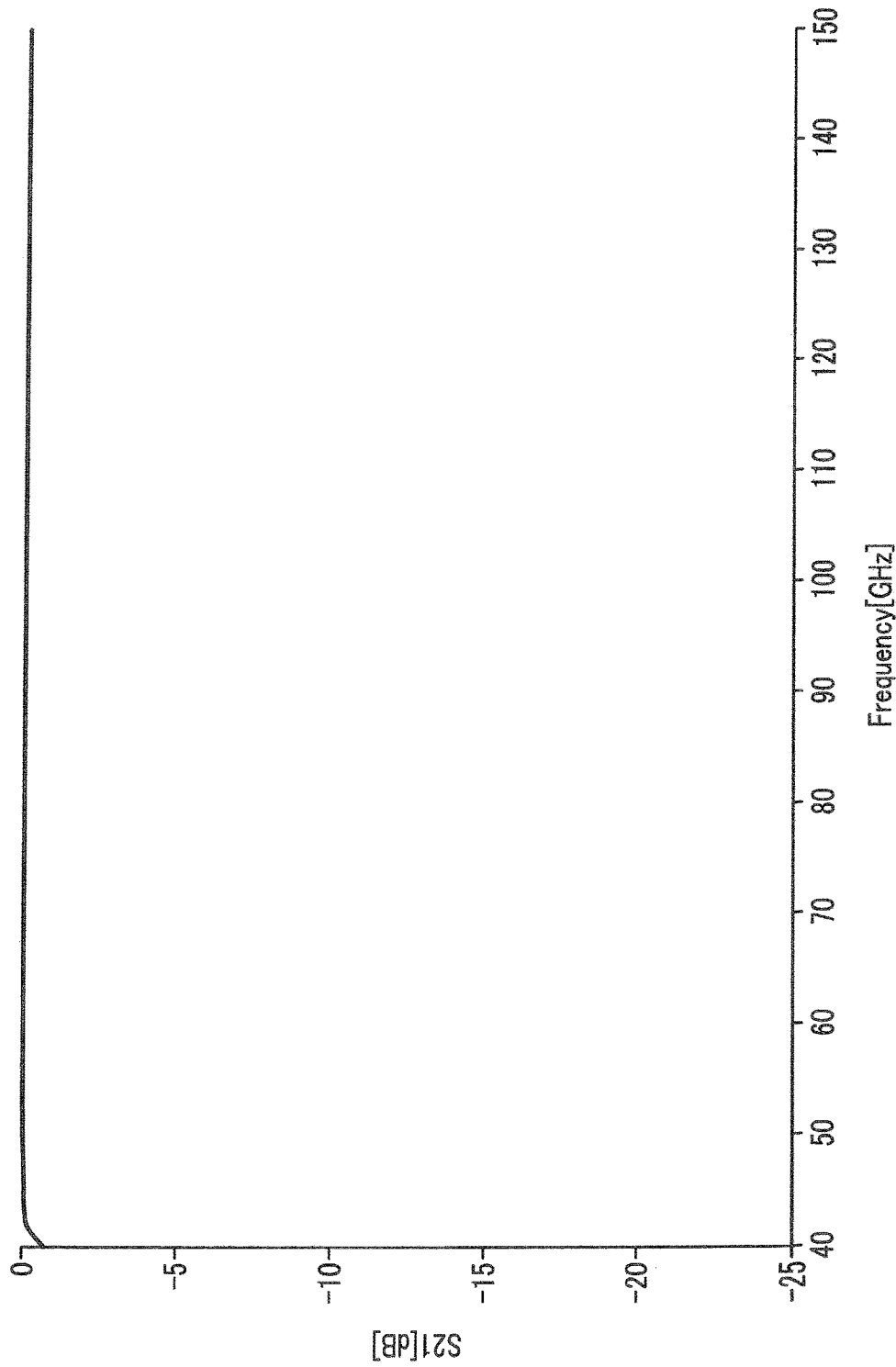
FIG. 49 is a diagram showing a transmission characteristic relating to the low-order reflection band in a case of the number of braided strings=32 in the simulation model relating to the flexible waveguide in the third embodiment.

FIG. 45 is an exterior perspective view showing the simulation model relating to the flexible waveguide in the third embodiment. FIG. 46 is a table diagram showing a relation among the number of braided strings, a yarn width, and a hole diameter of the braiding hole set in the simulation model relating to the flexible waveguide in the third embodiment. FIG. 47 is a diagram showing a transmission characteristic relating to the low-order reflection band in a case of the number of braided strings=8 in the simulation model relating to the flexible waveguide in the third embodiment. FIG. 48 is a diagram showing a transmission characteristic relating to the low-order reflection band in a case of the number of braided strings=16 in the simulation model. FIG. 49 is a diagram showing a transmission characteristic relating to the low-order reflection band in a case of the number of braided strings=32 in the simulation model.

In calculating a transmission loss relating to the flexible waveguide 550 in the third embodiment, as shown in FIG. 45, a simulation model of a square waveguide having a length of 20 mm is assumed.

This simulation model (the simulation model according to the third embodiment is hereinafter referred to as a third simulation model) is the square waveguide having the length of 20 mm as explained above. A predetermined dielectric is disposed on an inside of the simulation model.

As in the first simulation model explained above, a material of the inner dielectric in the third simulation model is PFA (perfluoroalkoxy alkane). The inner dielectric has a specific dielectric constant $\varepsilon_r = 2.0$ and dielectric loss tangent (tan δ)=0.0003 and has a square cross section, respective sides of which in a rectangular shape of the cross section are a long side a=2.66 mm and a short side b=1.33 mm.

Note that, assuming transmission of a 60 GHz millimeter wave, dimensions of the sectional shape are set such that a satisfactory transmission characteristic is obtained at 50 to 75 GHz (a V band). A simulator used in the simulation is HFSS manufactured by ANSYS, Inc. An analysis error (ΔS) is set to 0.01.

In the third simulation model, the external conductor 553 is disposed to cover an outer side of the inner dielectric 551. The cyclic unevenness 554 equivalent to the braiding holes is formed on an inner peripheral surface of the external conductor 553 in the longitudinal direction. Air is filled in gaps (recesses equivalent to the braiding holes explained above) in the cyclic unevenness 554. Electric conductivity of the cyclic unevenness 554 is set to $59 \times 10^6$ S/m equivalent to the electric conductivity of pure copper.

In the third simulation model, the number of braided strings (M) is set as a parameter. As shown in FIG. 46, transmission characteristics at the time of the number of braided strings (M)=8, 16, and 32 are simulated.

Note that, in the third simulation model, when the number of braided strings (M) are eight, sixteen, and thirty-two described above, the yarn width (s) and the diameter (p) of the braiding hole are respectively set to values shown in a table of FIG. 46.

The number of braided strings (M), the yarn width (s), and the diameter (p) of the braiding hole respectively correspond to the number of braidings (M), the width (s) of the flat foil yarn, and the length (p) of one side of the braiding hole. A ratio of the yarn width and the diameter of the braiding hole is set close to approximately 50%. The third simulation model has a cyclic structure at an interval of the cyclic length L in the propagating direction relating to the braiding hole represented by the following equation:

$$L = (s+p)/\sqrt{2} \qquad \text{Equation (33)}$$

As explained above, in the third simulation model set in this way, the simulation is carried out in three patterns in which the number of braided strings is respectively M=8, M=16, and M=32. A millimeter wave (or a submillimeter wave) is inputted to the respective patterns.

FIG. 47 is a diagram showing a transmission characteristic relating to a low-order reflection band in the case of the number of braided strings=8 in the simulation model relating to the flexible waveguide in the third embodiment. FIG. 48 is a diagram showing a transmission characteristic relating to the low-order reflection band in the case of the number of braided strings=16 in the simulation model relating to the flexible waveguide in the third embodiment. FIG. 49 is a diagram showing a transmission characteristic relating to the low-order reflection band in the case of the number of braided strings=32 in the simulation model relating to the flexible waveguide in the third embodiment.

In all the figures showing the transmission characteristics, a horizontal axis represents a frequency. From the relation of light speed=wavelength×frequency, it turns out that the wavelength and the frequency have a relation in which the frequency decreases when the wavelength increases and the frequency increases when the wavelength decreases. A vertical axis represents a transmission characteristic in a dB unit. The vertical axis indicates that the transmission characteristic is better as a numerical value is closer to 0.

The cutoff wavelength λc in the basic mode of the third simulation model is represented as follows from the waveguide dimensions and the specific dielectric constant of the inner dielectric:

$\lambda c = 7.518$ mm

This is represented in a frequency unit as follows:

$fc = 39.9$ GHz

Since a ratio of the waveguide long side "a" and the waveguide short side "b" in the third simulation model is 2:1, the following relation holds concerning the cutoff wavelength λch in the high-order mode:

$\lambda ch = \lambda c/2$

Therefore, the cutoff wavelength λch is represented as follows:

$\lambda ch = 3.758$ mm

This is represented in a frequency unit as follows:

$fch = 79.8$ GHz

Accordingly, the frequency band transmitted only in the basic mode is 39.9 GHz to 79.8 GHz (which covers the V band, which is a target frequency band).

In the third simulation model, M>6 is satisfied in all the cases. A main reflection band is absent in the frequency band transmitted only in the basic mode.

However, in simulation results shown in FIG. 47 to FIG. 49, even in the case of the number of braided stings M=8 in which a main reflection band should be absent in the frequency band transmitted only in the basic mode, as shown in FIG. 47, deterioration in the transmission characteristic due to a reflection band is observed near 66 GHz. It can be inferred that this is caused by influence of the "low-order reflection band" explained above.

Further, as shown in FIG. 47, in the case of the number of braided strings M=8, deterioration in the transmission characteristics due to the low-order reflection band is observed in a plurality of parts on a high frequency side.

In this way, in the case of the number of braided strings M=8, the low-order reflection band is present in the frequency band transmitted only in the basic mode. It turns out that the transmission characteristic is deteriorated in the frequency band transmitted only in the basic mode.

On the other hand, in the case of the number of braided strings M=16, as shown in FIG. 48, deterioration in the transmission characteristic due to the low-order reflection band is observed near 142 GHz. The deterioration in the transmission characteristic near 142 GHz is caused by the low-order reflection band explained above and is sufficiently larger than the maximum (79.8 GHz) of the frequency band transmitted only in the basic mode.

Further, in the case of the number of braided strings M=16, Expression (32) described above is satisfied. It turns out that a stable transmission characteristic is obtained in the frequency band transmitted only in the basic mode.

Further, in the case of the number of braided strings M=32, as shown in FIG. 49, deterioration in the transmission characteristic due to a reflection band is not observed in a range up to 150 GHz. This indicates that a simulation range is 40 to 150 GHz and even the low-order reflection band does not appear besides the main reflection band in this range. Note that it is likely that a reflection band is present at a frequency higher than 150 GHz.

In the case of the number of braided strings M=32, Expression (32) described above is satisfied. It turns out that a stable transmission characteristic is obtained in the frequency band transmitted only in the basic mode.

From a result of the simulation explained above, it is inferred that a boundary where the transmission characteristic stabilizes is present between eight and sixteen of the number of braided strings M. In the boundary, the number of braided strings is larger than the condition of the number of braided strings considering only the case in which only the main reflection band is considered, that is, Expression (32). From this, it can be determined that the third simulation model explained above has "a form including a longer cyclic structure with respect to a wavelength region where the main reflection band occurs" and influence of not only the main reflection band but also the low-order reflection band generated by the main reflection band is avoided.

<Measurement of Transmission Characteristic Relating to Flexible Waveguide in Third Embodiment>

Figure 50:
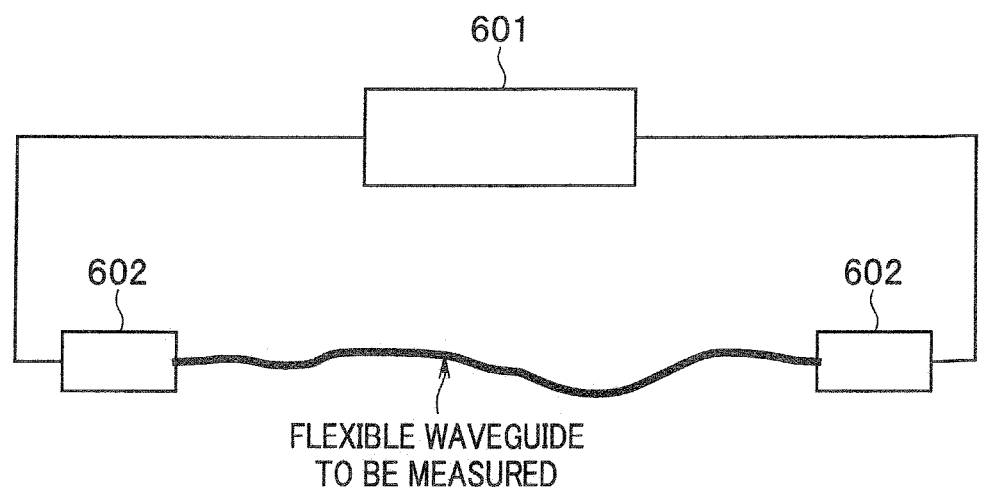
FIG. 50 is a block diagram showing a measurement system of a transmission characteristic relating to the flexible waveguide in the third embodiment.

FIG. 50 is a block diagram showing a measurement system of the transmission characteristic relating to the flexible waveguide in the third embodiment. FIG. 51 is a diagram showing a measurement result of a transmission characteristic in a 50 to 75 GHz band in the cases of the number of braided strings=16 and 32 in the flexible waveguide in the third embodiment. FIG. 52 is a diagram showing a measurement result of a transmission characteristic in a 75 to 110 GHz band in the case of the number of braided strings=32 in the flexible waveguide in the third embodiment.

Note that, in the flexible waveguide in the third embodiment, in addition to the holes called "braiding holes" explained above, complicated unevenness due to crossed braiding of the flat foil yarns shown in FIG. 43, nonuniformity of stitches that occurs in a long cycle because of characteristics and fluctuation of a braiding machine, and the like can occur. In other words, the external conductor of the flexible waveguide in the third embodiment has "the complicated form including the longer cyclic structure" explained above.

The inventor performed verification by measurement based on the inner dielectric and the external conductor specifications indicated by the third simulation explained above.

FIG. 50 is a block diagram showing a measurement system of a transmission characteristic relating to the flexible waveguide in the third embodiment. A so-called vector network analyzer 601 is used as a measurement device. Coaxial waveguide converters 602 adapted to measurement of the V band (50 to 75 GHz) are connected to both ends of the vector network analyzer 601.

FIG. 51 is a diagram showing a measurement result of the transmission characteristic in the cases of the number of braided strings=16 and 32 in the flexible waveguide in the third embodiment.

In FIG. 51, a horizontal axis represents a frequency. From the relation of light speed=wavelength×frequency, the wavelength and the frequency have a relation in which the frequency decreases when the wavelength increases and the frequency increases when the wavelength decreases. A vertical axis represents a transmission characteristic in a dB unit. The vertical axis indicates that the transmission characteristic is better as a numerical value is closer to 0.

As shown in FIG. 51, in the measurement result, in the case of the number of braided strings=16, deterioration in the transmission characteristic is observed near 60 to 65 GHz and 70 to 75 GHz. It turns out that the transmission characteristic is deteriorated. This is considered to be deterioration in the transmission characteristic due to a reflection band.

On the other hand, in the case of the number of braided strings=32, great deterioration in the transmission characteristic is not observed. A satisfactory transmission characteristic is obtained near 60 GHz or more.

Further, the inventor performed verification by measurement in a W band (75 to 110 GHz; this frequency band is hereinafter referred to as a W band), which is a frequency band further on the high frequency side relative to the V band.

The measurement was carried out with the coaxial waveguide converters 602 replaced with coaxial waveguide converters adapted to the measurement of the W band in the measurement system shown in FIG. 50.

FIG. 52 is a diagram enlarging and showing a measurement result of a transmission characteristic in a 75 to 110 GHz band in the case of the number of braided strings=32. As shown in FIG. 52, it turns out that a satisfactory transmission characteristic is obtained in a range of the W band, which is a band further on the high frequency side, besides the V band.

Note that, as shown in FIG. 51 and FIG. 52, the transmission characteristic is deteriorated at 50 to 55 GHz in both the figures. However, this is due to influence of design and assembly precision of the flexible waveguide. The deterioration in the transmission characteristic occurs because a cutoff frequency shifts from a design value (39.8 GHz) to the high frequency side.

Therefore, from the measurement results, it is inferred that a threshold where the transmission characteristic stabilizes is present between sixteen and thirty-two of the number of braided strings. When "a low-order reflection band that occurs in a range of five times wavelength with respect to a wavelength region where a main reflection band occurs relatively easily occurs and easily affects the transmission characteristic of the waveguide" explained above is considered, it can be determined that a stable transmission characteristic is obtained if a value of the boundary satisfies M>30, which is a value five times as large as the relational expression M>6 considering only the influence of the main reflection band, is satisfied.

Note that, to avoid the influence of the low-order reflection band, it is desirable to set the number of braided strings five times or more as large as the relational expression considering only the influence of the main reflection band. However, yarns (flat foil yarns) used for external conductor formation become thinner and manufacturing becomes more difficult as the number of braided strings increases. Therefore, in actual external conductor manufacturing, it can be said that it is desirable to select as small a number of braided strings as possible in a range in which the number of braided strings exceeds thirty.

A frequency band in a millimeter band increases, the waveguide itself becomes thinner. The yarns (the flat foil yarns) used for the external conductor formation also become thinner because of influence of the thinning of the waveguide. In other words, it is sometimes considered to be difficult to set the number of braided yarns to thirty or more. In this case, if eighteen or more, which is the number of braided strings three times or more as large as the relational expression considering only the main reflection band, is selected, a certain effect can be expected for improvement of the transmission characteristic. It is possible to balance the improvement of the transmission characteristic and manufacturability.

As explained above, with the flexible waveguide in the third embodiment, even in the waveguide in which the cyclic unevenness like the braiding holes that can generate a complicated reflection band is formed as in the external conductor 553 assuming the braid shape, by appropriately setting a cyclic length of the cyclic unevenness, it is possible to avoid presence of a main reflection band and a low-order reflection band in a wavelength band transmitted only in a desired basic mode. It is possible to provide the waveguide that achieves both of appropriate flexibility and an excellent transmission characteristic in the waveguide that transmits a radio wave having a frequency equal to or higher than a frequency of a desired millimeter wave (including a submillimeter wave).

Fourth Embodiment

A fourth embodiment of the present invention is explained.

In the first to third embodiments, the flexible waveguide explained above is applied to the endoscope. However, in the fourth embodiment, the flexible waveguide explained above is applied to an image transmission apparatus that transmits a predetermined image signal.

The image transmission apparatus according to the fourth embodiment is not limited to the endoscope system indicated in the first to third embodiments and is a transmission apparatus capable of transmitting a high definition/large capacity image signal represented by a 4 K/8 K image exceeding so-called FHD (full high definition). In other words, the image transmission apparatus is a transmission apparatus including a transmission line for a high-speed signal, a basic frequency of which exceeds 10 GHz.

Further, it is assumed that the transmission line according to the fourth embodiment is used in a millimeter wave (including a submillimeter wave) region that can realize communication speed equal to or higher than 5 Gbps with length equal to or smaller than approximately several centimeters to five meters. The transmission line is required to have flexibility.

The flexible waveguide including the dielectric material explained above in the first embodiment can also be appropriately applied to the image transmission apparatus in the fourth embodiment that requires such conditions.

The present invention is not limited to the embodiments explained above. Various changes, alternations, and the like of the present invention are possible in a range in which the gist of the present invention is not changed.

What is claimed is:

1. A waveguide comprising:
a linear dielectric, a dielectric constant of which is uniform in a longitudinal direction and a cross section of which assumes a same shape in the longitudinal direction; and
an external conductor disposed in a position covering an outer periphery of the dielectric and comprising a tube having flexibility,
wherein:
the waveguide conducts a radio wave in a frequency band equal to or higher than a frequency band of a millimeter wave or a submillimeter wave near 60 GHz or higher,
the external conductor includes a metal layer,
the metal layer has a cyclic structure, a shape of an inner periphery side section of the metal layer facing the dielectric and forming a cyclic shape displacement member in the waveguide longitudinal direction,
the cyclic structure is a structure satisfying $\lambda mr < \lambda ch$, where $\lambda mr$ represents a center wavelength of a main reflection band due to the cyclic structure and $\lambda ch$ represents a cutoff wavelength in a high-order mode of the waveguide, and
the cyclic structure is a structure in which a cycle L in the waveguide longitudinal direction of the shape displacement member in the cyclic structure satisfies $L < \lambda c/(4 \times \sqrt{\varepsilon r})$, where $\lambda c$ represents a cutoff wavelength in a basic mode of the waveguide and $\varepsilon r$ represents a specific dielectric constant of the dielectric.

2. The waveguide according to claim 1, wherein:
the metal layer has a bellows shape in which a cyclic unevenness section is formed in the waveguide longitudinal direction, and
the cyclic structure is a structure in which a minimum cycle L relating to the cyclic unevenness section in the bellows shape in the cyclic structure satisfies $L < \lambda c/(4 \times \sqrt{\varepsilon r})$, where $\lambda c$ represents the cutoff wavelength in the basic mode of the waveguide and $\varepsilon r$ represents the specific dielectric constant of the dielectric.

3. An image transmission apparatus comprising the waveguide according to claim 1, wherein the waveguide transmits a predetermined image signal.

4. An endoscope comprising the waveguide according to claim 1, wherein the waveguide transmits a predetermined image signal.

5. An endoscope system comprising:
the endoscope according to claim 4; and
an image-signal processing circuit configured to apply predetermined image processing to the predetermined image signal transmitted by the waveguide.

6. A waveguide comprising:
a linear dielectric, a dielectric constant of which is uniform in a longitudinal direction and a cross section of which assumes a same shape in the longitudinal direction; and
an external conductor disposed in a position covering an outer periphery of the dielectric and comprising a tube having flexibility,
wherein:
the waveguide conducts a radio wave in a frequency band equal to or higher than a frequency band of a millimeter wave or a submillimeter wave near 60 GHz or higher,
the external conductor includes a metal layer,
the metal layer has a cyclic structure, a shape of an inner periphery side section of the metal layer facing the dielectric and forming a cyclic shape displacement member in the waveguide longitudinal direction,
the cyclic structure is a structure satisfying $\lambda mr < \lambda ch$, where $\lambda mr$ represents a center wavelength of a main reflection band due to the cyclic structure and $\lambda ch$ represents a cutoff wavelength in a high-order mode of the waveguide,
the metal layer comprises at least one belt-like member including a metal substance, a cross section of the belt-like member perpendicular to an extending axis assuming a rectangular cross section,
the belt-like member extends such that, in a state in which a side edge portion of the belt-like member forms a predetermined angle with respect to the waveguide longitudinal axis, a flat section of the belt-like member is wound on an outer peripheral surface of the dielectric, and the belt-like member is disposed such that side edge portions facing each other in adjacent winds of the belt-like member keep a constant interval in the waveguide longitudinal direction, and
the cyclic structure is a structure satisfying $(s+p)/\cos\theta < \lambda c/(4 \times \sqrt{\varepsilon r})$, where $\lambda c$ represents the cutoff wavelength in the basic mode of the waveguide, $\varepsilon r$ represents the specific dielectric constant of the dielectric, s represents a width of the belt-like member, p represents the constant interval, and $\theta$ represents the predetermined angle with respect to the waveguide longitudinal axis at a time when an angle orthogonal to the waveguide longitudinal axis is set to 0 degrees.

7. A waveguide comprising:
a linear dielectric, a dielectric constant of which is uniform in a longitudinal direction and a cross section of which assumes a same shape in the longitudinal direction; and
an external conductor disposed in a position covering an outer periphery of the dielectric and comprising a tube having flexibility,
wherein:
the waveguide conducts a radio wave in a frequency band equal to or higher than a frequency band of a millimeter wave or a submillimeter wave near 60 GHz or higher,
the external conductor includes a metal layer,
the metal layer has a cyclic structure, a shape of an inner periphery side section of the metal layer facing the dielectric and forming a cyclic shape displacement member in the waveguide longitudinal direction,
the cyclic structure is a structure satisfying $\lambda mr < \lambda ch$, where $\lambda mr$ represents a center wavelength of a main reflection band due to the cyclic structure and $\lambda ch$ represents a cutoff wavelength in a high-order mode of the waveguide,
the metal layer comprises a plurality of belt-like members including a metal substance, a cross section of each of the belt-like members perpendicular to an extending axis assuming a rectangular cross section,
the plurality of belt-like members extend, in a state in which side edge portions of all the belt-like members form a predetermined angle with respect to the waveguide longitudinal axis, such that flat sections of the belt-like members are wound on an outer peripheral surface of the dielectric and the plurality of belt-like members are composed arranged to form a braid-like form with one another, and
the cyclic structure is a structure satisfying $(L1z/M) < \lambda c/(4 \times \sqrt{\varepsilon r})$, where $\lambda c$ represents the cutoff wavelength in the basic mode of the waveguide, $\varepsilon r$ represents the specific dielectric constant of the dielectric, L1z represents an entire peripheral dimension of the waveguide cross section, and M represents a number of the belt-like members used to form the braid-like form.

8. The waveguide according to claim 7, wherein the belt-like member comprises one of (i) a film comprising a resin film and metal, and (ii) a yarn including a foil.

9. A waveguide comprising:

a linear dielectric, a dielectric constant of which is uniform in a longitudinal direction and a cross section of which assumes a same shape in the longitudinal direction; and an external conductor disposed in a position covering an outer periphery of the dielectric and comprising a tube having flexibility, wherein:

the waveguide conducts a radio wave in a frequency band equal to or higher than a frequency band of a millimeter wave or a submillimeter wave near 60 GHz or higher, the external conductor includes a metal layer, the metal layer has a cyclic structure, a shape of an inner periphery side section of the metal layer facing the dielectric and forming a cyclic shape displacement member in the waveguide longitudinal direction, the cyclic structure is a structure satisfying $\lambda mr<\lambda ch$, where $\lambda mr$ represents a center wavelength of a main reflection band due to the cyclic structure and $\lambda ch$ represents a cutoff wavelength in a high-order mode of the waveguide, and the cyclic structure is a structure satisfying $\lambda sr>\lambda c$ or $\lambda sr<\lambda ch$, where $\lambda sr$ represents a center wavelength of a low-order reflection band appearing in a wavelength band different from a main reflection band due to the cyclic structure, $\lambda c$ represents the cutoff wavelength in the basic mode of the waveguide, and $\lambda ch$ represents a cutoff wavelength in a high-order mode.

10. The waveguide according to claim 9, wherein the cyclic structure is a structure in which a cycle L in the waveguide longitudinal direction of the shape displacement member in the cyclic structure satisfies $L<\lambda c/(20\times\sqrt{\varepsilon r})$, where $\lambda c$ represents the cutoff wavelength in the basic mode of the waveguide and $\varepsilon r$ represents the specific dielectric constant of the dielectric.

11. The waveguide according to claim 9, wherein:

the metal layer comprises a plurality of belt-like members including a metal substance, a cross section of each of the belt-like members perpendicular to an extending axis assuming a rectangular cross section, the plurality of belt-like members extend, in a state in which side edge portions of all the belt-like members form a predetermined angle with respect to the waveguide longitudinal axis, such that flat sections of the belt-like members are wound on an outer peripheral surface of the dielectric and the plurality of belt-like members are arranged to form a braid-like form with one another, and the cyclic structure is a structure satisfying $(L1z/M)<\lambda c/(20\times\sqrt{\varepsilon r})$, where $\lambda c$ represents the cutoff wavelength in the basic mode of the waveguide, $\varepsilon r$ represents the specific dielectric constant of the dielectric, L1z represents an entire peripheral dimension of the waveguide cross section, and M represents a number of the belt-like members used to form the braid-like form.

* * * * *